(12) United States Patent
Messerly et al.

(10) Patent No.: US 10,058,346 B2
(45) Date of Patent: Aug. 28, 2018

(54) ULTRASONIC SURGICAL INSTRUMENT WITH REMOVABLE CLAMP ARM

(71) Applicant: Ethicon Endo-Surgery, Inc., Cincinnati, OH (US)

(72) Inventors: Jeffrey D. Messerly, Cincinnati, OH (US); Daniel W. Price, Loveland, OH (US); Foster B. Stulen, Mason, OH (US); Matthew C. Miller, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 267 days.

(21) Appl. No.: 14/488,330

(22) Filed: Sep. 17, 2014

(65) Prior Publication Data
US 2016/0074060 A1 Mar. 17, 2016

(51) Int. Cl.
*A61B 17/32* (2006.01)
*A61B 17/00* (2006.01)

(52) U.S. Cl.
CPC ........ *A61B 17/320092* (2013.01); *A61B 2017/0042* (2013.01); *A61B 2017/0046* (2013.01); *A61B 2017/320078* (2017.08)

(58) Field of Classification Search
CPC .... A61B 17/320068; A61B 17/320092; A61B 2017/0042; A61B 2017/0046; A61B 2017/320076
See application file for complete search history.

(56) References Cited

U.S. PATENT DOCUMENTS

| | | |
|---|---|---|
| 5,322,055 A | 6/1994 | Davison et al. |
| 5,324,299 A | 6/1994 | Davison et al. |
| 5,873,873 A | 2/1999 | Smith et al. |
| 5,980,510 A | 11/1999 | Tsonton et al. |
| 6,139,561 A * | 10/2000 | Shibata .......... A61B 17/320068 606/169 |

(Continued)

FOREIGN PATENT DOCUMENTS

| | | |
|---|---|---|
| WO | WO 00/78237 A1 | 12/2000 |
| WO | WO 2005/084250 A2 | 9/2005 |
| WO | WO 2016/044277 A1 | 3/2016 |

OTHER PUBLICATIONS

U.S. Appl. No. 14/028,717, filed Sep. 17, 2013.

(Continued)

*Primary Examiner* — Shaun L David
(74) *Attorney, Agent, or Firm* — Frost Brown Todd LLC

(57) ABSTRACT

An ultrasonic instrument comprises a handle assembly or other kind of body configured to receive an ultrasonic transducer, a shaft assembly having an acoustic waveguide and an ultrasonic blade, and a removable clamp arm. The ultrasonic blade is in acoustic communication with the acoustic waveguide such that the ultrasonic transducer is operable to drive the ultrasonic blade to vibrate ultrasonically via the acoustic waveguide. The clamp arm is configured to selectively couple with and decouple from the shaft assembly and/or handle assembly of the ultrasonic instrument. The clamp arm may include a coupler or other coupling feature configured to selectively couple the clamp arm with the shaft assembly and/or the handle assembly. The ultrasonic instrument may further comprise a guidance system configured to position and/or orient the clamp arm relative to the ultrasonic instrument.

14 Claims, 59 Drawing Sheets

(56) References Cited

U.S. PATENT DOCUMENTS

| | | |
|---|---|---|
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,773,444 B2 | 8/2004 | Messerly |
| 6,783,524 B2 | 8/2004 | Anderson et al. |
| 8,057,498 B2 | 11/2011 | Robertson |
| 8,152,825 B2 | 4/2012 | Madan et al. |
| 8,226,675 B2 | 7/2012 | Houser et al. |
| 8,461,744 B2 | 6/2013 | Wiener et al. |
| 8,591,536 B2 | 11/2013 | Robertson |
| 8,623,027 B2 | 1/2014 | Price et al. |
| 8,911,460 B2 | 12/2014 | Neurohr et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0163807 A1* | 6/2009 | Sliwa ............ A61N 7/02 600/439 |
| 2010/0069940 A1 | 3/2010 | Miller et al. |
| 2010/0331873 A1* | 12/2010 | Dannaher ...... A61B 17/320092 606/169 |
| 2011/0087212 A1 | 4/2011 | Aldridge et al. |
| 2012/0112687 A1 | 5/2012 | Houser et al. |
| 2012/0116265 A1 | 5/2012 | Houser et al. |
| 2014/0005701 A1 | 1/2014 | Olson et al. |
| 2014/0114334 A1 | 4/2014 | Olson et al. |

OTHER PUBLICATIONS

U.S. Appl. No. 14/031,665, filed Sep. 19, 2013.
U.S. Appl. No. 14/488,454, filed Sep. 17, 2014.
U.S. Appl. No. 61/410,603, filed Nov. 5, 2010.
International Search Report and Written Opinion dated Jan. 5, 2016 for Application No. PCT/US2015/050191, 11 pgs.

* cited by examiner

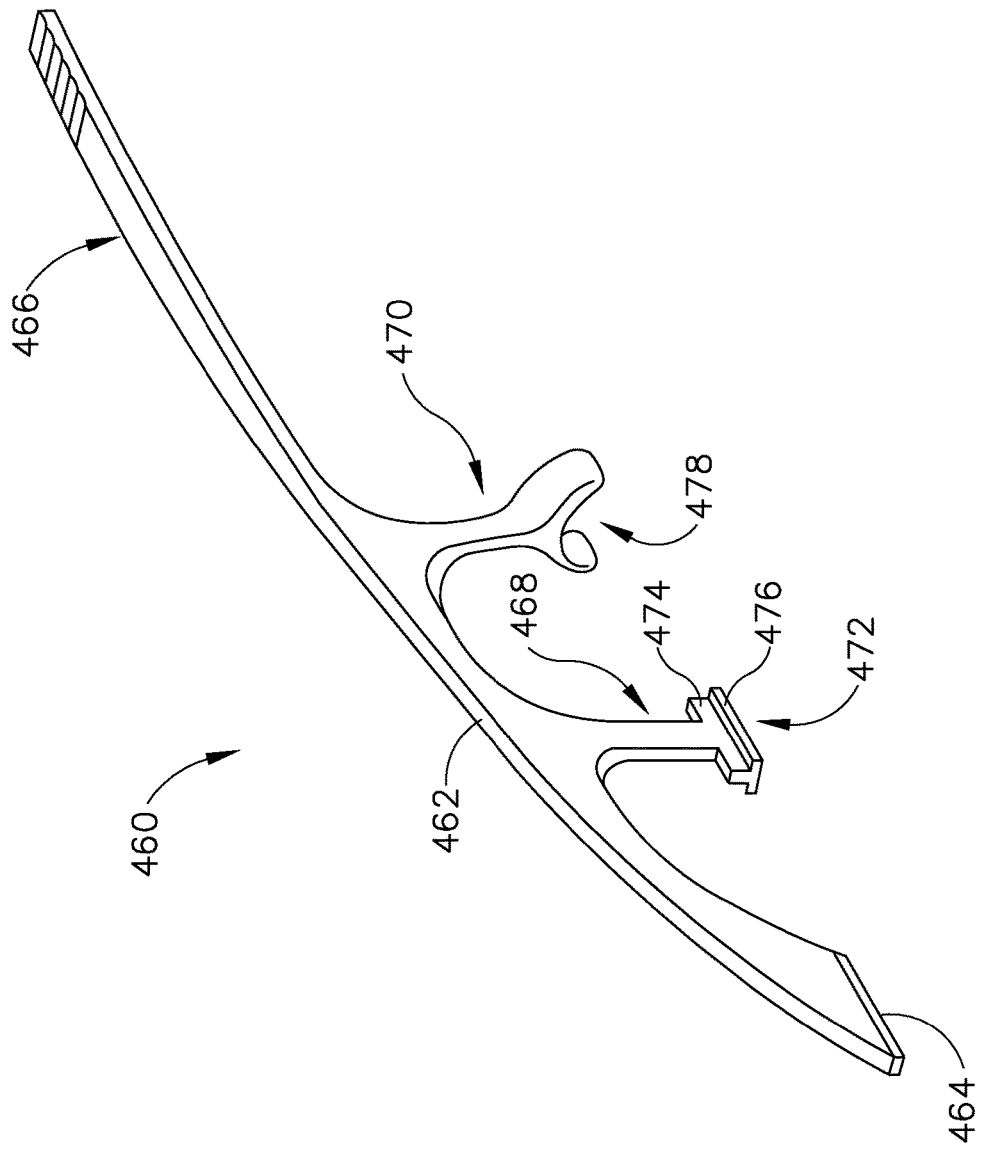

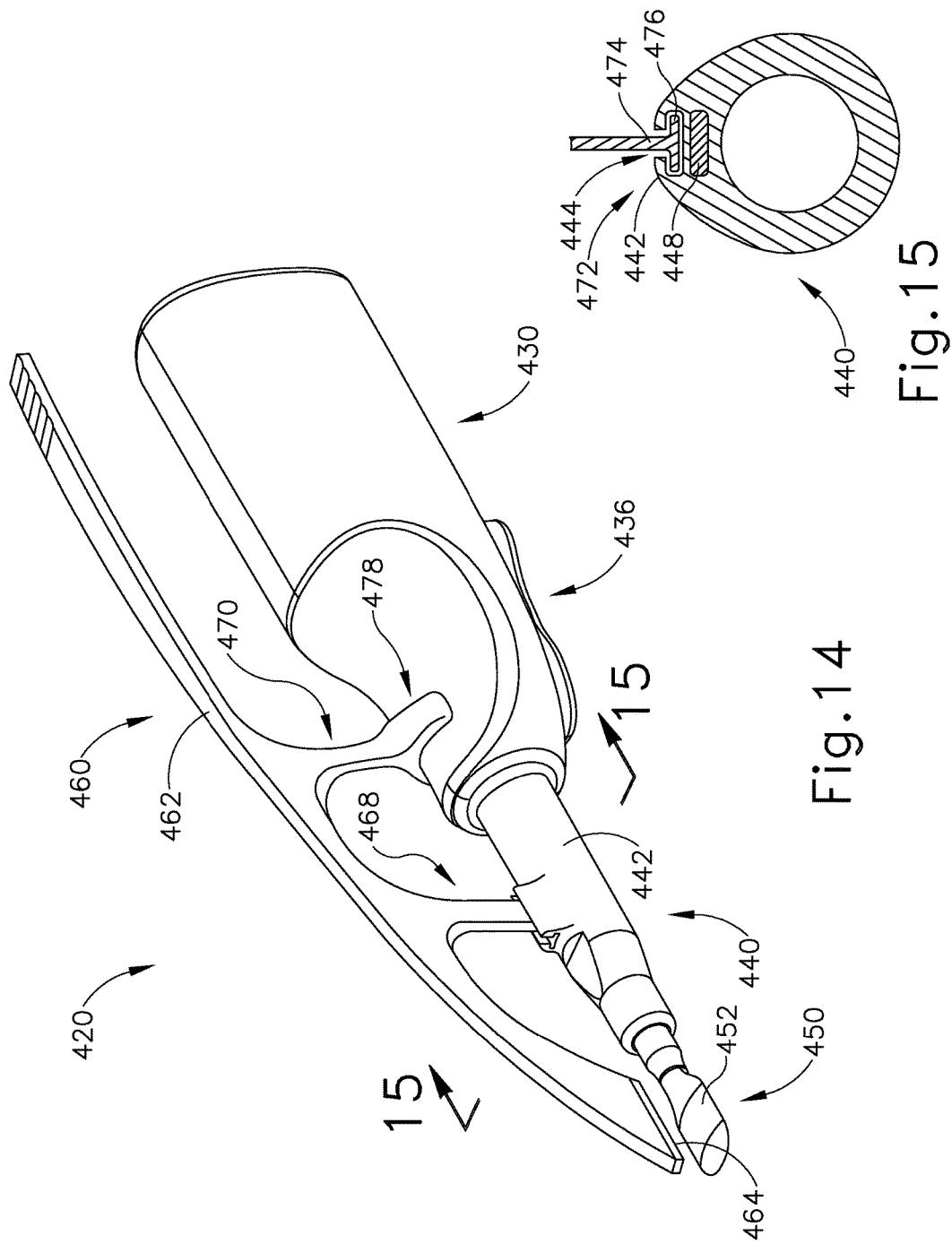

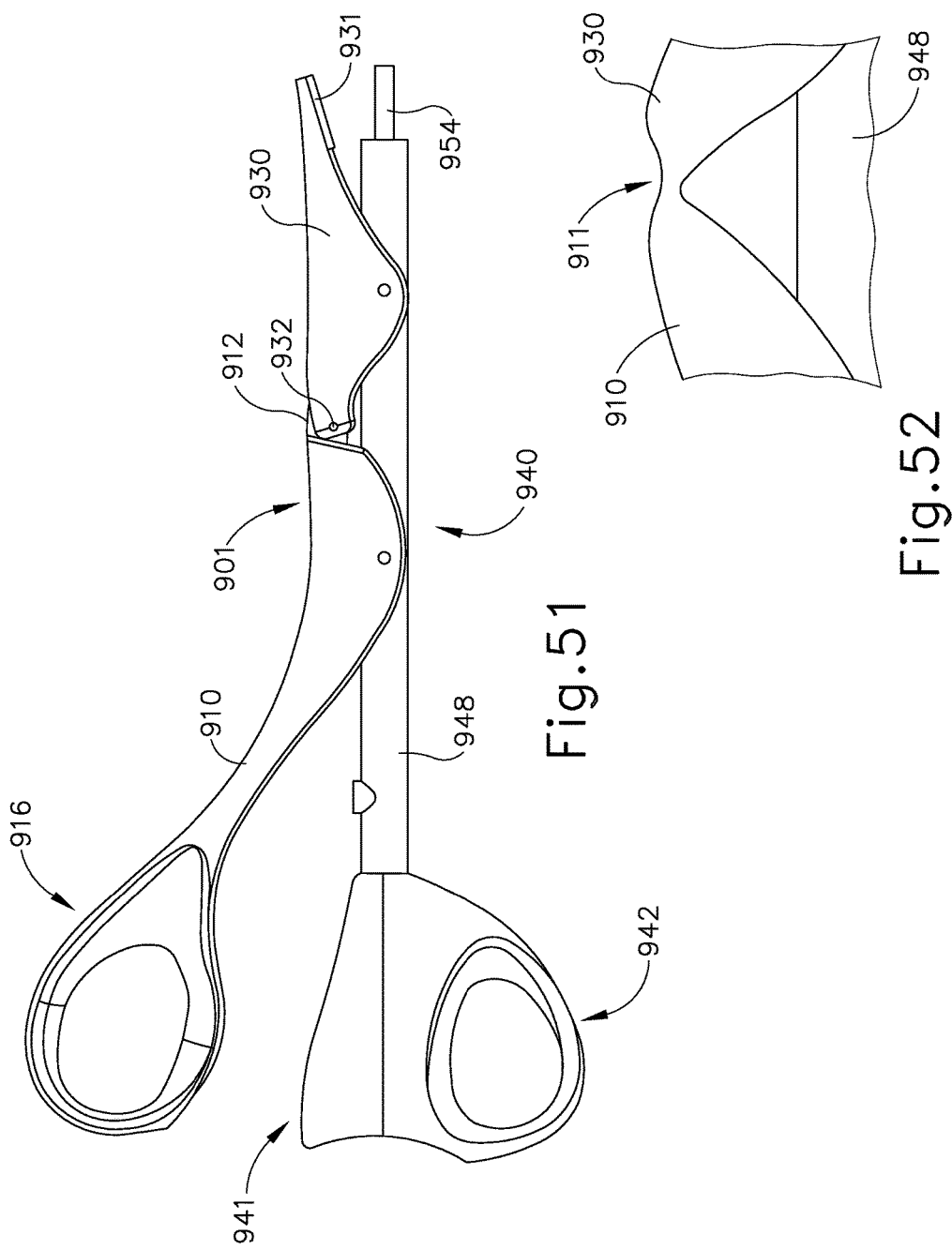

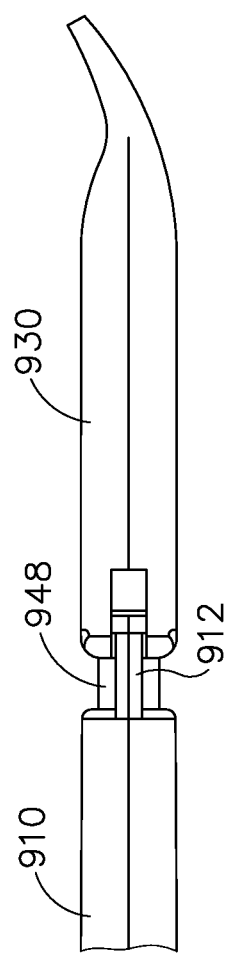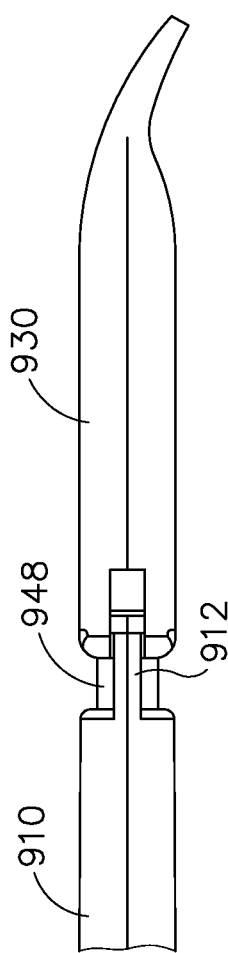

ULTRASONIC SURGICAL INSTRUMENT WITH REMOVABLE CLAMP ARM

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2008/0234710, entitled "Ultrasonic Surgical Instruments," published Sep. 25, 2008, now U.S. Pat. No. 8,911,460, issued on Dec. 16, 2014, the disclosure of which is incorporated by reference herein; and U.S. Pub. No. 2010/0069940, entitled "Ultrasonic Device for Fingertip Control," published Mar. 18, 2010, now U.S. Pat. No. 9,023,071, issued on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued on Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, entitled "Surgical Instruments with Articulating Shafts," now U.S. Pat. No. 9,393,037, issued on Jul. 19, 2016, the disclosure of which is incorporated by reference herein; and U.S. Pub. No. 2014/0114334, published Apr. 24, 2014, entitled "Flexible Harmonic Waveguides/Blades for Surgical Instruments," now U.S. Pat. No. 9,095,367, issued on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 13 depicts a perspective view of yet another exemplary removable clamp arm;

FIG. 14 depicts a perspective view of the clamp arm of FIG. 13 attached to yet another exemplary alternative surgical instrument;

FIG. 15 depicts a cross-sectional front view of the clamp arm of FIG. 13 and the instrument of FIG. 14 taken along line 15-15 of FIG. 14;

FIG. 51 depicts a side elevational view of the shaft assembly and clamp arm of FIG. 47, with the clamp arm moved into an open position;

FIG. 52 depicts a detailed side elevational view of an exemplary alternative joint of the clamp arm of FIG. 47;

FIG. 53 depicts a top view of an exemplary end effector of the clamp arm of FIG. 47; and FIG. 54 depicts a top view of an exemplary alternative end effector of the clamp arm of FIG. 47.

Figure 1:
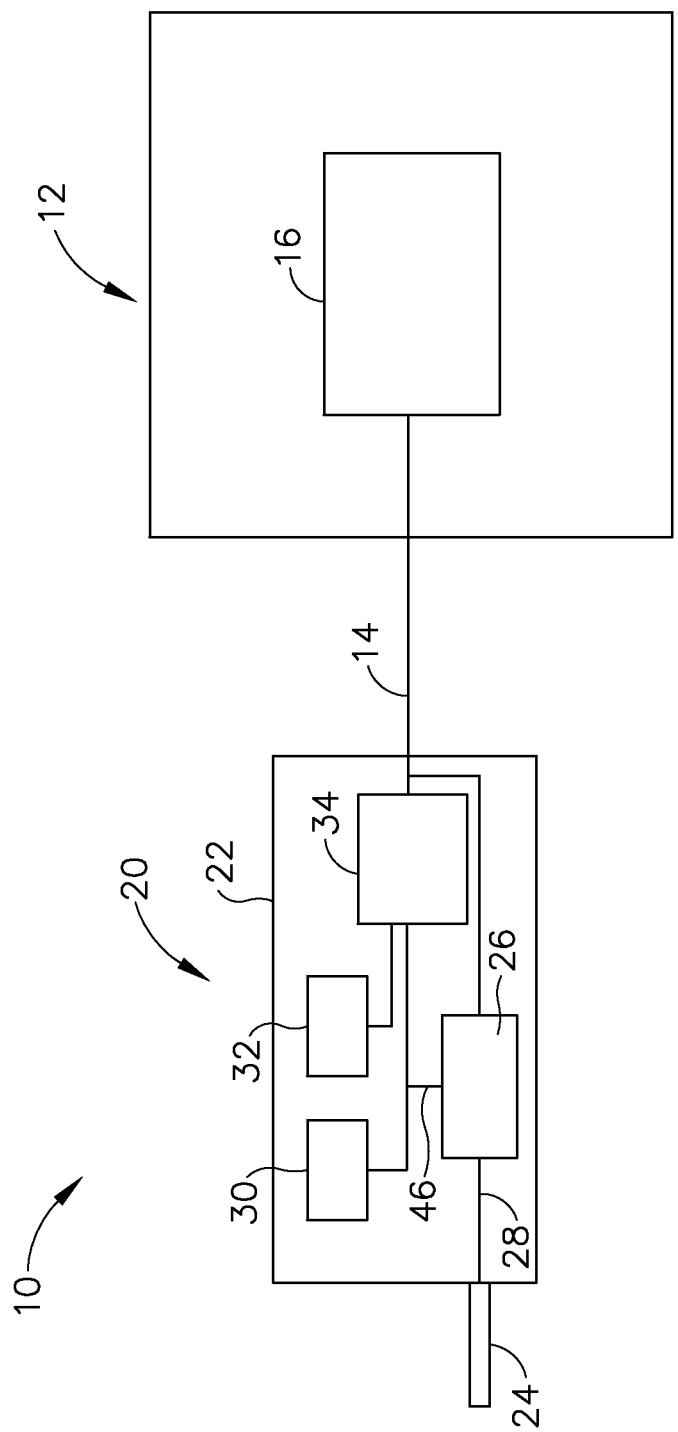
FIG. 1 depicts a block schematic view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (nλ/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instruments

The following discussion relates to various exemplary components and configurations for instrument (20) and components thereof. It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 1-54 illustrate exemplary ultrasonic surgical instruments (120, 220, 320, 420, 520, 620, 720, 800, 850, 900). At least part of each instrument (120, 220, 320, 420, 520, 620, 720, 800, 850, 900) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pat. No. 8,461,744; U.S. Pub. No. 2009/0105750, now U.S Pat. No. 8,623,027, issued on Jan. 7, 2014, U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071, issued on May 5, 2015; U.S. Pub. No. 2012/0112687, now U.S. Pat. No. 9,381,058, issued on Jul. 5, 2016; U.S. Pub. No. 2012/0116265; U.S. Pub. No. 2014/0005701, now U.S. Pat. No. 9,393,037, issued on Jul. 19, 2016; U.S. Pat. Pub. No. 2014/0114334, now U.S. Pat. No. 9,095,367, issued on Aug. 4, 2015; U.S. patent application Ser. No. 14/028,717, published as U.S. Pub. No. 2015/0080924 on Mar. 19, 2015; and/or U.S. Pat. App. No. 61/410,603. The disclosures of each of the foregoing patents, publications, and applications are incorporated by reference herein. As described therein and as will be described in greater detail below, each instrument (120, 220, 320, 420, 520, 620, 720, 800, 850, 900) is operable to cut tissue and seal or weld tissue (e.g., a blood vessel, etc.) substantially simultaneously. It should also be understood that instruments (120, 220, 320, 420, 520, 620, 720, 800, 850, 900) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instruments (120, 220, 320, 420, 520, 620, 720, 800, 850, 900) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instruments (120, 220, 320, 420, 520, 620, 720, 800, 850, 900), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
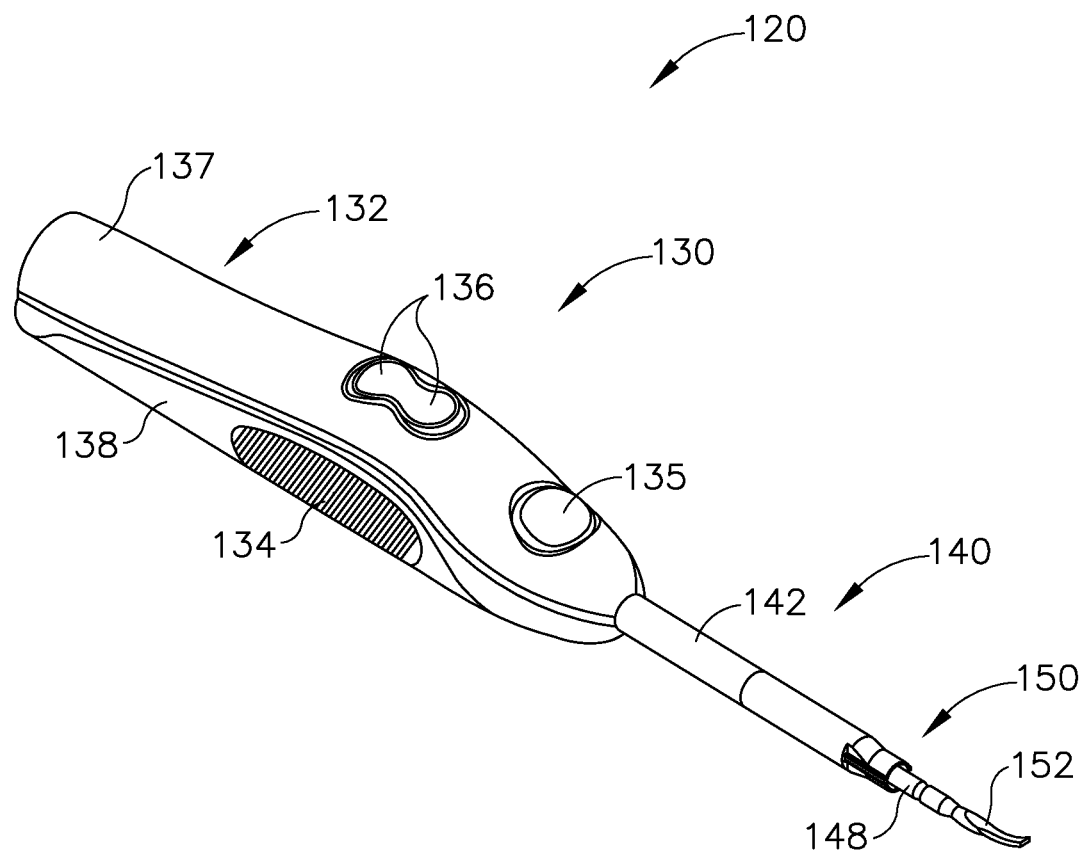
FIG. 2 depicts a perspective view of another exemplary surgical instrument.
Figure 3:
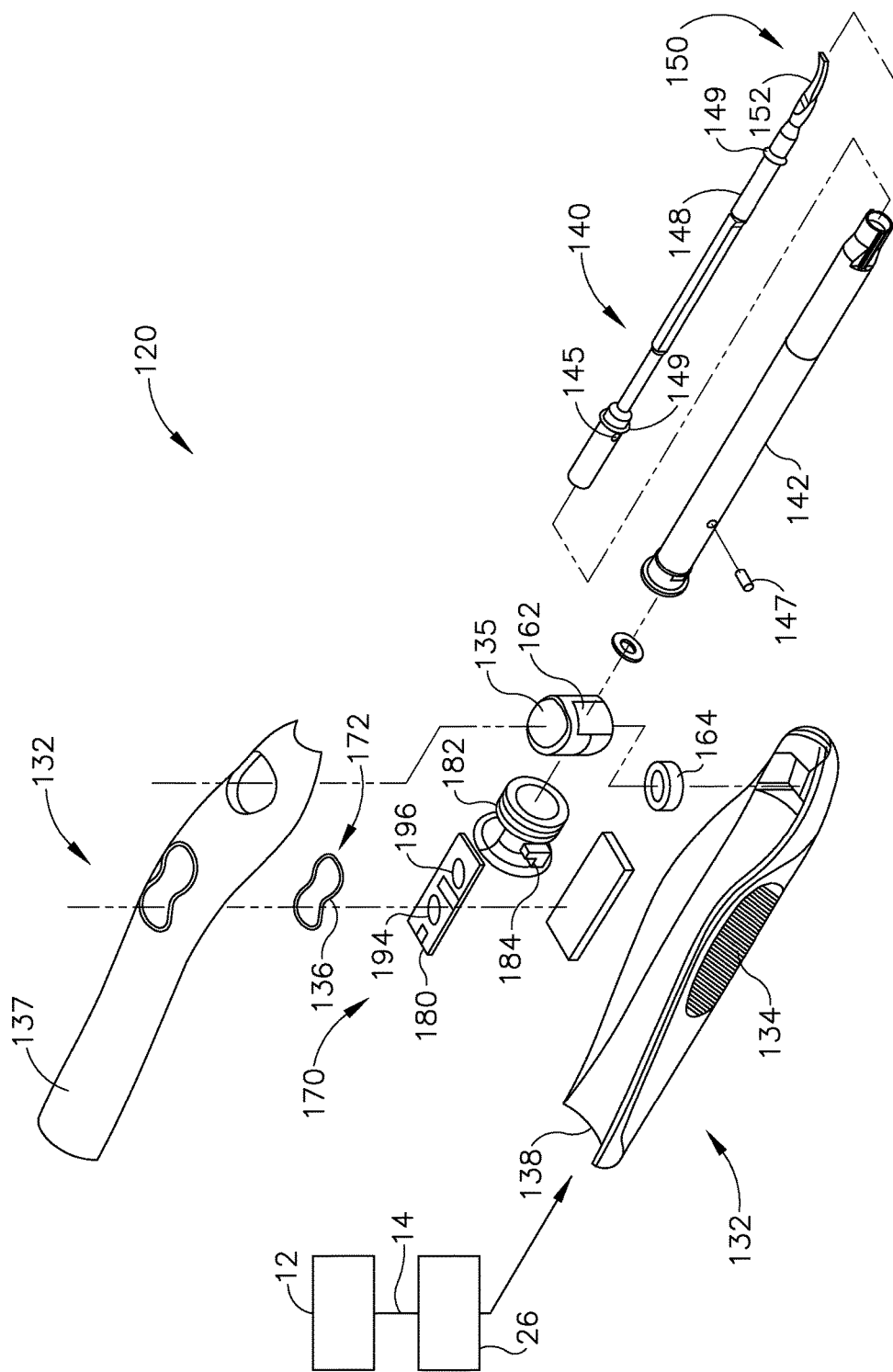
FIG. 3 depicts an exploded perspective view of the instrument of FIG. 2.

FIGS. 2 and 3 illustrate an exemplary ultrasonic surgical instrument (120) that is configured to be used as a scalpel (e.g., in facial plastic surgery, etc.). Instrument (120) may be used in conjunction with ultrasonic surgical system (10), which includes ultrasonic transducer (26) coupled with ultrasonic generator (12) via cable (14). Instrument (120) of this example comprises a handle assembly (130), a shaft assembly (140), and an end effector (150). In some versions, handle assembly (130) may receive ultrasonic transducer (26) which may couple to a waveguide (148) in shaft assembly (140) by a threaded connection, though any other suitable type of coupling may be used. Handle assembly (130) comprises a tubular elongate body (132) including a grip portion (134) and a plurality of buttons (135, 136). Handle assembly (130) omits any clamp arm, and instrument (120) is merely used as an ultrasonic scalpel for simultaneously slicing and cauterizing tissue. Thus, handle assembly (130) includes grip portion (134) which is configured to permit a user to grip handle assembly (130) from a variety of positions. By way of example only, handle assembly (130) may be shaped to be grasped and manipulated in a pencil-like arrangement. Handle assembly (130) of the present example comprises mating housing portions (137) and (138). While a multi-piece handle assembly (130) is illustrated, handle assembly (130) may alternatively comprise a single or unitary component. Handle assembly (130) may be constructed from a durable plastic, such as polycarbonate or a liquid crystal polymer. It is also contemplated that handle assembly (130) may alternatively be made from a variety of materials or combinations of materials, including but not limited to other plastics, ceramics, and/or metals, etc. In some versions, the proximal end of instrument (120) receives and is fitted with ultrasonic transducer (26) by insertion of ultrasonic transducer (26) into handle assembly (130). Instrument (120) may be attached to and removed from ultrasonic transducer (26) as a unit.

As shown in FIG. 3, shaft assembly (140) comprises an outer sheath (142), and a waveguide (148) disposed within outer sheath (142). Waveguide (148), which is configured to transmit ultrasonic energy from transducer (26) to an ultrasonic blade (152), may be flexible, semi-flexible or rigid. Waveguide (148) may also be configured to amplify the mechanical vibrations transmitted through waveguide (148) to blade (152). Waveguide (148) may further include at least one bore (145) extending therethrough, substantially perpendicular to the longitudinal axis of waveguide (148). Bore (145) is located at a longitudinal position corresponding to a node associated with ultrasonic vibrations communicated along waveguide (148). Bore (145) is configured to receive a connector pin (147), which connects ultrasonic waveguide (148) to outer sheath (142).

As mentioned above, end effector (150) omits any clamp arm. Instead, end effector (150) merely consists of ultrasonic blade (152) which may be used for simultaneously slicing and cauterizing tissue. In some alternative versions, including but not limited to those described below, end effector (150) may include a clamp arm. Blade (152) may be integral with ultrasonic waveguide (148) and formed as a single unit. In some versions, blade (152) may be connected to waveguide (148) by a threaded connection, a welded joint, and/or some other coupling feature(s). The distal end of blade (152) is disposed at or near a longitudinal position corresponding to an anti-node associated with ultrasonic vibrations communicated along waveguide (148) and blade (152) in order to tune the acoustic assembly to a preferred resonant frequency $f_o$ when the acoustic assembly is not loaded by tissue. When transducer (26) is energized, the distal end of blade (152) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. The distal end of blade (152) may also vibrate in the y-axis at about 1 to about 10 percent of the motion in the x-axis. Of course, movement of blade (152) may alternatively have any other suitable characteristics.

Waveguide (148) is positioned within outer sheath (142) and held in place via pin (147). Pin (147) may be made of any compatible metal, such as stainless steel or titanium or a durable plastic, such as polycarbonate or a liquid crystal polymer. Alternatively, any other suitable material or combination of materials may be used. In some versions, pin (147) is partially coated with an elastomeric material, such as silicon, etc., for the portion of pin (147) that extends through ultrasonic waveguide (148). Elastomeric material may provide insulation from the vibrating blade throughout the length of bore (145). In some settings, this may enable high efficiency operation whereby minimal overheating is generated and maximum ultrasonic output power is available at the distal end of blade (152) for cutting and coagulation, etc. Of course, such elastomeric material is merely optional.

As can be seen in FIG. 3, waveguide (148) has a plurality of acoustic isolators (149) positioned along the longitudinal length of waveguide (148). Isolators (149) may provide structural support to waveguide (148); and/or acoustic isolation between waveguide (148) and other portions of shaft assembly (140). Isolators (149) generally have a circular or ovular cross-section and extend circumferentially around the diameter of waveguide (148). The inner diameter of each isolator (149) is generally sized slightly smaller than the outer diameter of waveguide (148) to create a slight interference fit, thus securing each isolator (149) to waveguide (148). In some examples, waveguide (148) may include annular, recessed channels that are configured to receive each isolator (149) to further aid in securing each isolator (149) along the longitudinal length of waveguide (148). In the present example, each isolator (149) is positioned at or near to an acoustic node along the longitudinal length of waveguide (148) (i.e., a longitudinal position corresponding to a node associated with resonant ultrasonic vibrations communicated through waveguide (148)). Such positioning may reduce the vibrations transferred to isolators (149) (and to other components in contact with isolators (149)) via waveguide (148).

Outer sheath (142) passes through an aperture (162) of release button (135). A spring (164) is positioned below button (135) and resiliently biases button (135) upwardly. The upward force imposed by spring (164) causes the perimeter of aperture (162) to firmly assert pressure against outer sheath (142), and thereby selectively prevents outer sheath (142), waveguide (148), and ultrasonic blade (152) from either rotating within handle assembly (130) or axially translating with respect to handle assembly (130). When the operator exerts a downward force on button (135), spring (164) is compressed and it no longer asserts a holding force on outer sheath (142). The operator may then axially translate outer sheath (142), waveguide (148), and blade (152) relative to handle assembly (130) and/or rotate outer sheath (142), waveguide (148), and blade (152) relative to handle assembly (130). Accordingly, it should be understood that the longitudinal and/or rotational position of blade (152) relative to handle assembly (130) may be selectively adjusted by the operator while depressing button (135), while still allowing blade (152) to vibrate ultrasonically at such selected positions, allowing blade (152) to be used in various surgical procedures at such selected positions. To initiate such ultrasonic action of blade (152), the operator may operate a footswitch (not shown), activate pair of buttons (136) as described below, activate a button on generator (12), or perform some other act on some component of system (10).

In the present example, body (132) of handle assembly (130) includes a proximal end, a distal end, and a cavity (139) extending longitudinally therein. Cavity (139) is configured to accept a switch assembly (170) and at least a portion of ultrasonic transducer assembly (26). In some versions, the distal end of transducer (26) threadably attaches to the proximal end of waveguide (148), though any other suitable type of coupling may be used. Electrical contacts of transducer (26) also interface with switch assembly (170) to provide the operator with finger-activated controls on surgical instrument (120). Transducer (26) of the present example includes two conductive rings (not shown) which are securely disposed within the body of transducer (26). Merely exemplary transducers having such conductive rings are also described in U.S. Pat. No. 8,152,825, entitled "Medical Ultrasound System and Handpiece and Methods for Making and Tuning," issued Apr. 10, 2012, the disclosure of which is incorporated by reference herein. Switch assembly (170) of the present example comprises a pushbutton assembly (172), a circuit assembly (180), a switch housing (182), a first pin conductor (184), and a second pin conductor (not shown). Switch housing (182) is annular-shaped and is supported within handle assembly (130) by way of corresponding supporting mounts on switch housing (182) and body (132).

Pushbutton assembly (172) of the present example comprises pair of buttons (136). Circuit assembly (180) provides for the electro-mechanical interface between pair of buttons (136) and generator (12) via transducer (26). Circuit assembly (180) comprises two dome switches (194, 196) that are mechanically actuated by depressing each button of pair of buttons (136). Dome switches (194, 196) are electrical contact switches, that when depressed provide an electrical signal to generator (12). In particular, various components of circuit assembly (180) interface with transducer (26) via the ring conductors of transducer (26), which are in turn connected to conductors in cable (14) that connects to generator (12). In an exemplary operation, when the operator depresses one button of the pair of buttons (136), generator (12) may respond with a certain energy level, such as a maximum ("max") power setting. When the operator depresses another button of the pair of buttons (136), generator (12) may respond with a certain energy level, such as a minimum ("min") power setting, which conforms to accepted industry practice for pushbutton location and the corresponding power setting. Instrument (120) may further be configured and operable in accordance with the teachings of U.S. Pub. No. 2008/0200940, entitled "Ultrasonic Energy Device for Cutting and Coagulating," published Aug. 21, 2008, the disclosure of which is incorporated by reference herein. Alternatively, instrument (120) may be provided with a variety of other components, configurations, and/or types of operability as will be apparent to those of ordinary skill in the art in view of the teachings herein.

In addition to or in lieu of being constructed in accordance with the above teachings, at least part of instrument (120)

may be constructed and operable in accordance with at least some of the teachings of U.S. Pat. No. 5,322,055; U.S. Pat. No. 5,873,873; U.S. Pat. No. 5,980,510; U.S. Pat. No. 6,283,981; U.S. Pat. No. 6,309,400; U.S. Pat. No. 6,325,811; U.S. Pat. No. 6,423,082; U.S. Pat. No. 6,783,524; U.S. Pat. No. 8,057,498; U.S. Pat. No. 8,461,744; U.S. Pub. No. 2006/0079874; U.S. Pub. No. 2007/0191713; U.S. Pub. No. 2007/0282333; U.S. Pub. No. 2008/0200940; U.S. Pub. No. 2008/0234710, now U.S. Pat. No. 8,911,460, issued on Dec. 16, 2014; U.S. Pub. No. 2010/0069940, now U.S. Pat. No. 9,023,071, issued on May 5, 2015; U.S. Pub. No. 2012/0112687, now U.S. Pat. No. 9,381,058, issued on Jul. 5, 2016; U.S. Pub. No. 2012/0116265; U.S. Pub. No. 2014/0005701, now U.S Pat. No. 9,393,037, issued on Jul. 19, 2016; U.S. Pub. No. 2014/0114334, now U.S. Pat. No. 9,095,367, issued on Aug. 4, 2015; and/or U.S. Pat. App. No. 61/410,603. The disclosures of each of the foregoing patents, publications, and applications are incorporated by reference herein. Additional merely illustrative variations for instrument (120) will be apparent to those of ordinary skill in the art in view of the teachings herein. It should be understood that the below described variations may be readily applied to instrument (120) described above and any of the instruments referred to in any of the references that are cited herein, among others.

III. Exemplary Modified Ultrasonic Scalpel Instrument with Removable Clamp Arm

It will be appreciated by those of ordinary skill in the art that it may be desirable in some versions of instrument (120) to provide instrument (120) with a clamp arm. A clamp arm may be used to compress tissue against ultrasonic blade (152) before and/or during ultrasonic activation of ultrasonic blade (152). Such compression may promote hemostasis in tissue and/or cutting of tissue more quickly and/or more effectively than hemostasis and/or cutting that could otherwise be achieved by ultrasonic blade (152) without a clamp arm. For instance, such a clamp arm may be desirable to enable instrument (120) to achieve large vessel hemostasis, e.g. vessels larger than 1 mm-2 mm in diameter. It may further be desirable to provide such clamp arms with features which allow them to be easily attached to and/or removed from instrument (120), i.e. a "removable" clamp arm. This may enable instrument (120) to selectively transition between two operational modes (one mode with clamp arm attached and another mode with clamp arm detached). The operator may thus chose whether to attach or detach the clamp arm based on whether a clamp arm would be useful in a particular clinical setting. The operator may further switch between these modes within the same surgical procedure, if desired. By way of example only, an operator may choose to operate instrument with the clamp arm detached when the operator wishes to use instrument (120) to primarily cut tissue; and operate instrument with the clamp arm attached when the operator wishes to use instrument (120) to primarily coaptate tissue and/or coagulate tissue.

Figure 4:
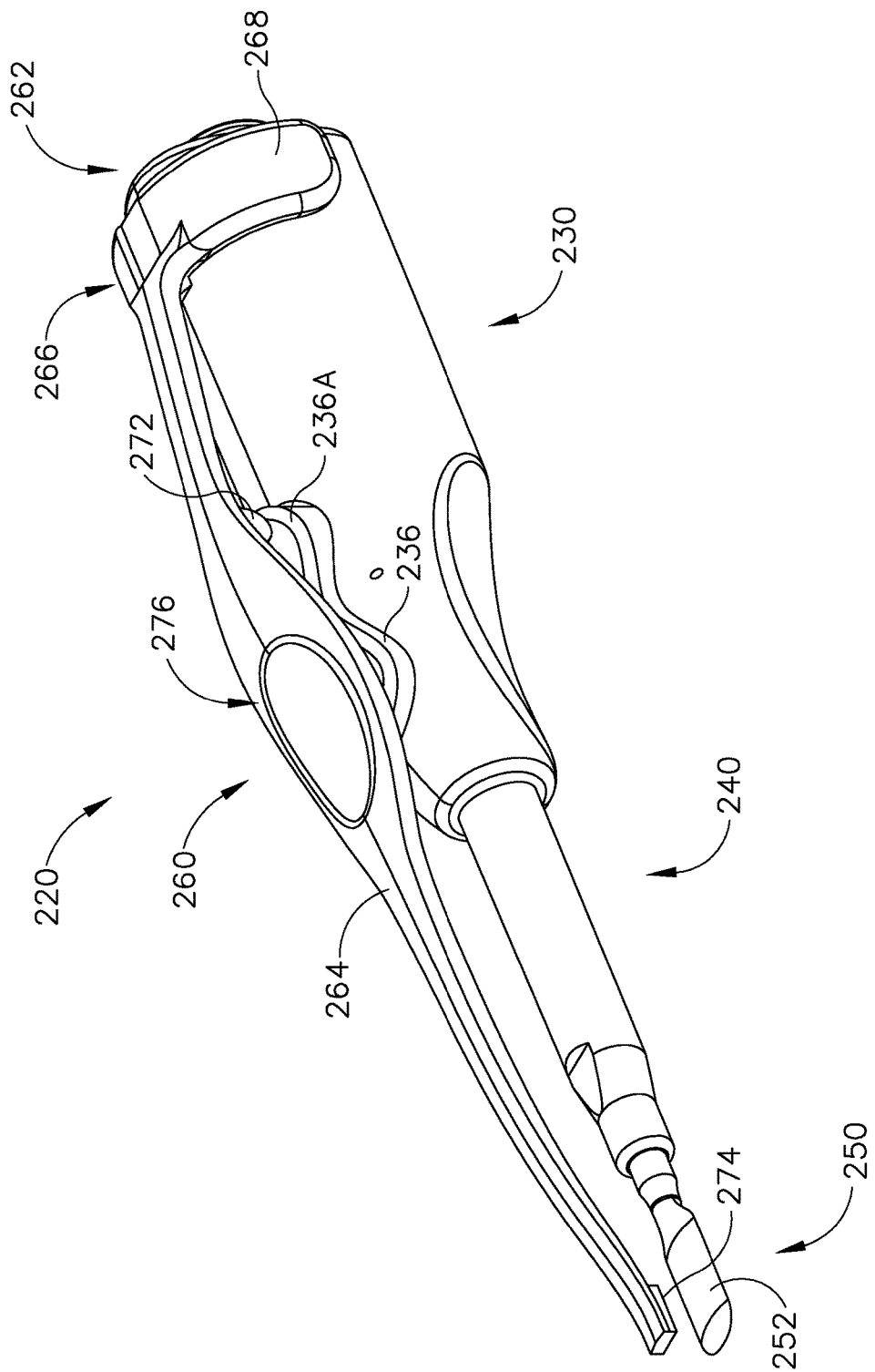
FIG. 4 depicts a perspective view of an exemplary alternative surgical instrument having a removable clamp arm.

As will be discussed in more detail below, FIGS. 4-55 show examples of such exemplary ultrasonic scalpel instruments having removable clamp arms. Various examples of such clamp arms will be described in greater detail below; while other examples will be apparent to those of ordinary skill in the art according to the teachings herein. It should be understood that the instruments described below are configured to function substantially similar to instruments (120) described above except for the differences described below. In particular, the instruments described below may be used to cut tissue and seal or weld tissue (e.g., a blood vessel, etc.) substantially simultaneously.

While the following examples are provided in the context of harmonic surgical instruments, it should be understood that the below teachings may also be readily incorporated into RF electrosurgical instruments. The clamp pad may be configured to include an RF return electrode. By way of example only, an RF electrosurgical instrument may be used with the clamp arm detached when the operator wishes to use the instrument in a monopolar mode; and the instrument may be used with the clamp arm attached when the operator wishes to use the instrument in a bipolar mode. Other suitable ways in which the teachings herein may be modified for incorporation into an RF electrosurgical context will be apparent to those of ordinary skill in the art in view of the teachings herein. Of course, the teachings herein may also be applied to instruments that provide both RF electrosurgical functionality and ultrasonic surgical functionality.

A. Exemplary Ultrasonic Scalpel Instrument with Snap-Fit Clamp Arm

FIGS. 4-7B illustrate an exemplary ultrasonic surgical instrument (220) configured to be used as a scalpel. Instrument (220) may be used in conjunction with ultrasonic surgical system (10), which includes ultrasonic transducer (26) coupled with ultrasonic generator (12) via cable (14). Instrument (220) of this example comprises a handle assembly (230), a shaft assembly (240), and an end effector (250). Instrument (220) is configured to operate substantially similar to instrument (120) discussed above except for the differences discussed below. In particular, instrument (220) may be used to cut tissue and seal or weld tissue (e.g., a blood vessel, etc.) substantially simultaneously. Unlike instrument (120) discussed above, however, instrument (220) of the present example comprises a removable clamp arm (260). As will be discussed in more detail below, clamp arm (260) is configured to be selectively coupled to handle assembly (230) in a snap-fit manner.

Figure 5:
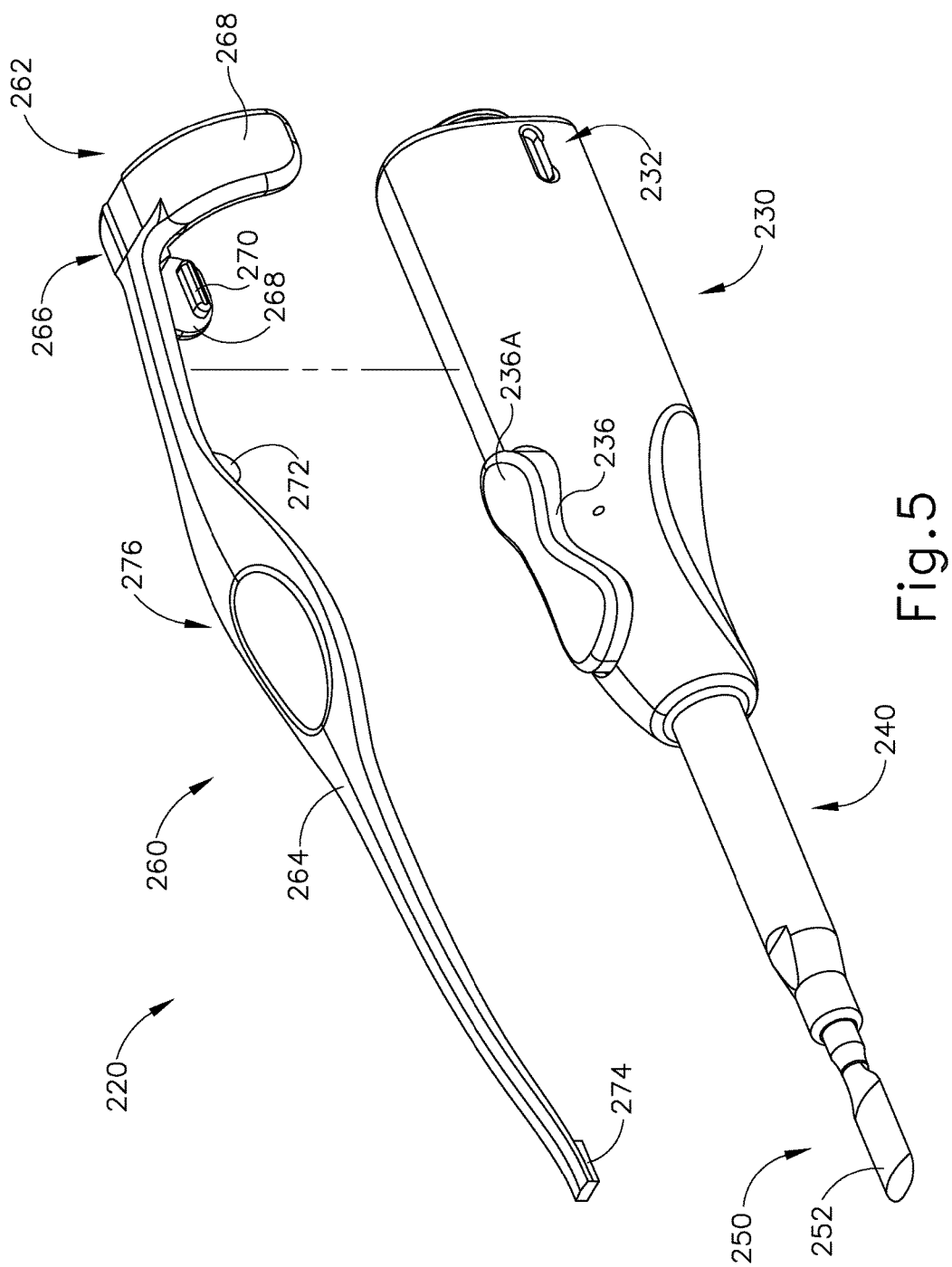
FIG. 5 depicts a partially exploded perspective view of the instrument and clamp arm of FIG. 4.
Figure 6:
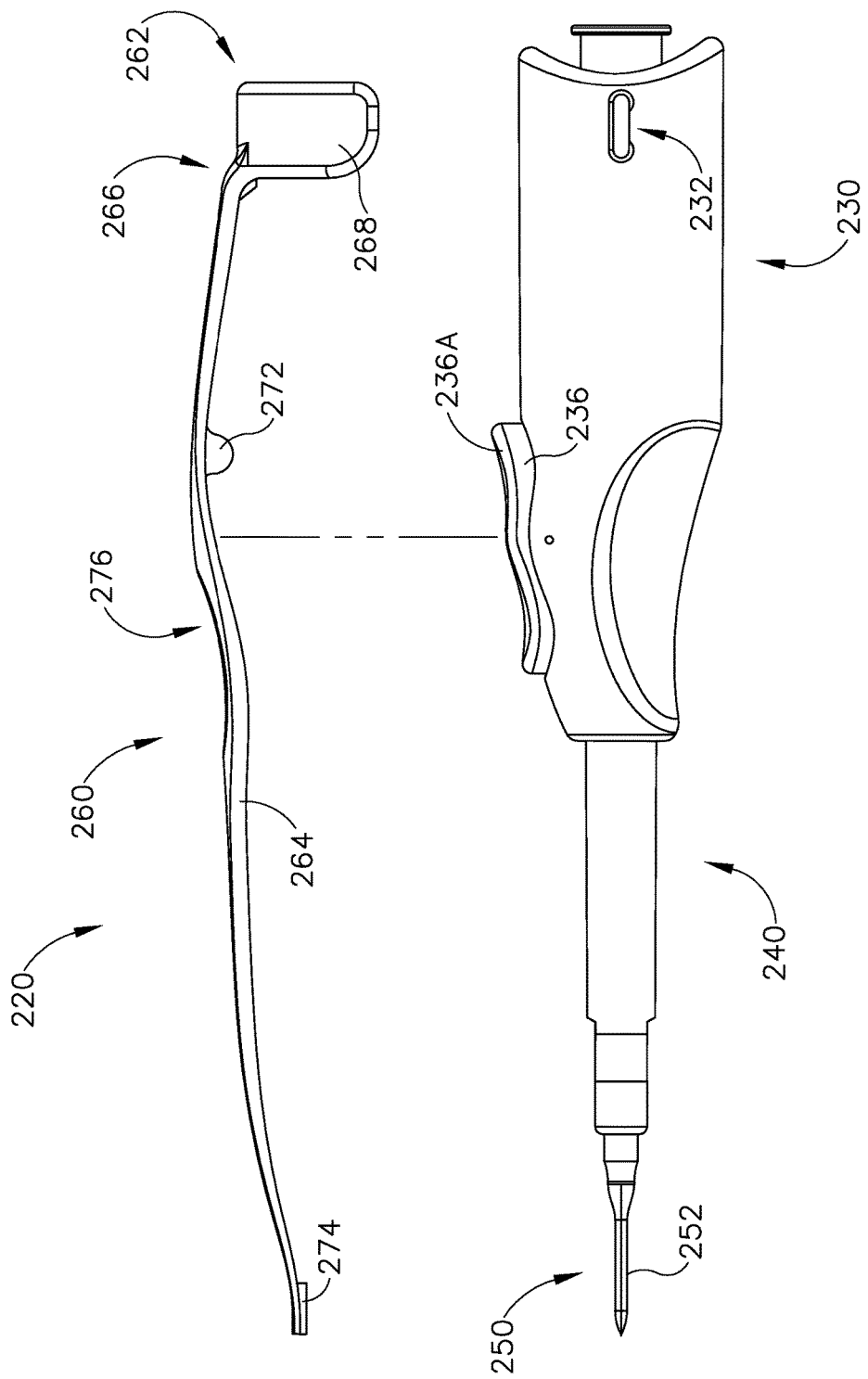
FIG. 6 depicts a partially exploded side elevational view of the instrument and clamp arm of FIG. 4.
Figure 7A:
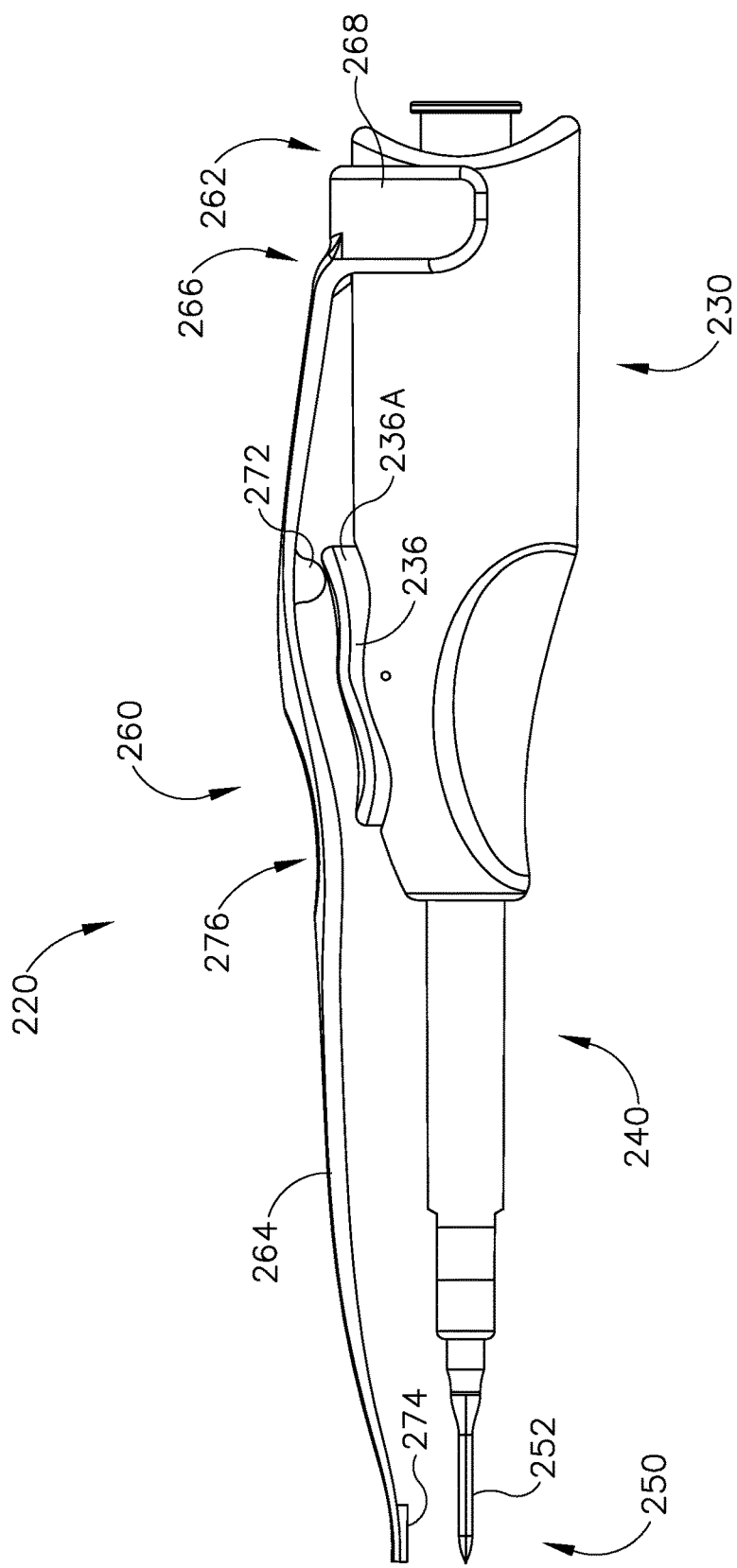
FIG. 7A depicts a side elevational view of the instrument and clamp arm of FIG. 4, with the clamp arm in a first position.
Figure 7B:
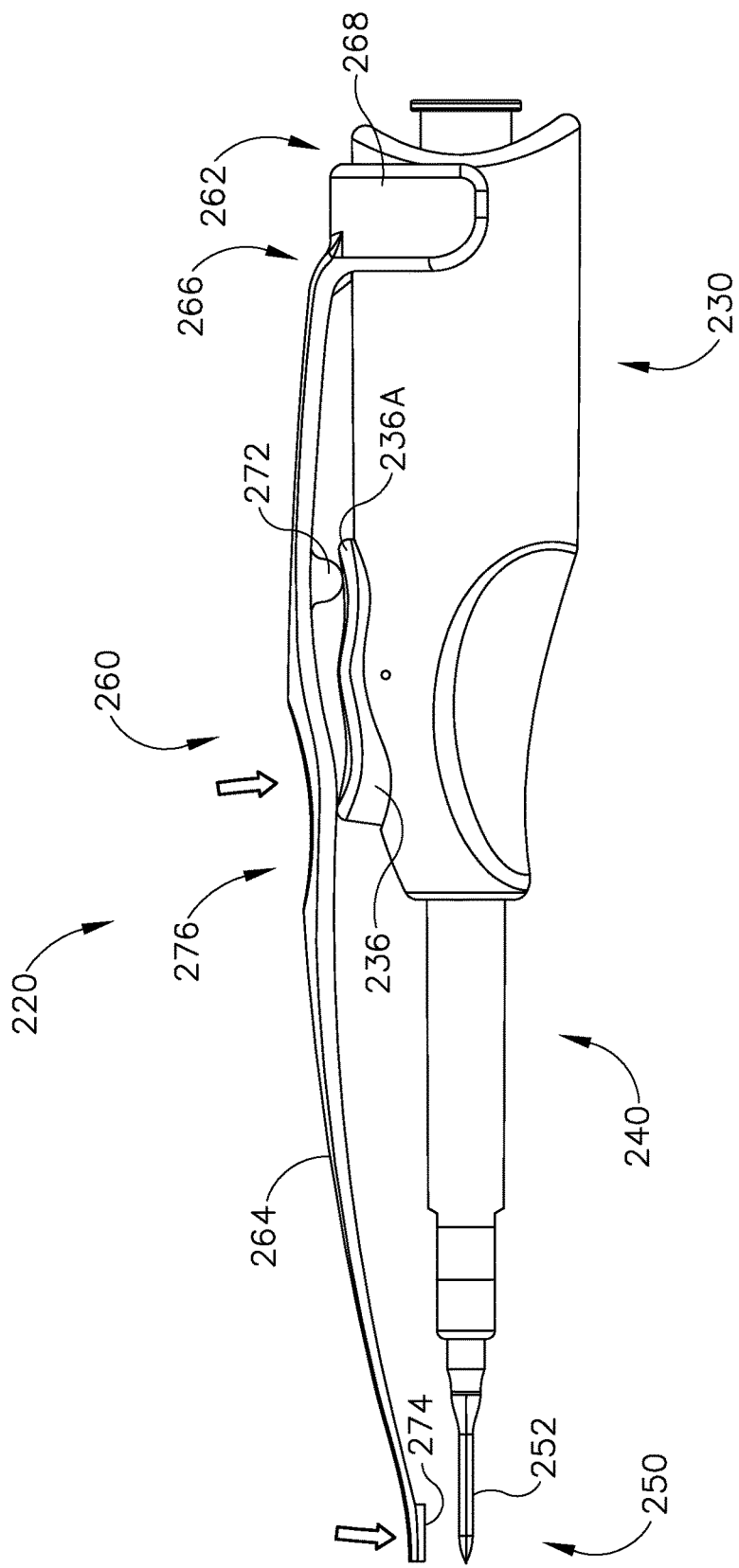
FIG. 7B depicts a side elevational view of the instrument and clamp arm of FIG. 4, with the clamp arm actuated into a second position.

Clamp arm (260) comprises an arcuate proximal portion (262) and a resilient arm (264). Arcuate proximal portion (262) comprises a pair of resilient limbs (268). Limbs (268) extend transversely from the proximal end of resilient arm (264). Limbs (268) are resiliently biased to assume the position best seen in FIG. 5, but are configured to flex as will be described in more detail below. Each limb (268) comprises a respective tab (270) extending inwardly from an interior surface of limb (268). As best seen in FIGS. 5 and 6, handle assembly (230) comprises a pair of recesses (232) formed in a proximal portion of handle assembly (230). Recesses (232) are configured to receive tabs (270) of limbs (268) in a snap fit manner. To couple clamp arm (260) with instrument (220), the operator forces arcuate proximal portion (262) of clamp arm (260) about the proximal portion of handle assembly (230) along a transverse path so as to position tabs (270) within recesses (232). The cylindrical shape of handle assembly (230) causes limbs (268) to flex outwardly due to engagement between an exterior surface of handle assembly (230) and tabs (270) as arcuate proximal portion (262) is forced about the proximal portion of handle assembly (230). Upon alignment of tabs (270) with recesses (232) of handle assembly (230), limbs (268) are configured to "snap" back into the position best seen in FIG. 4 such that tabs (270) are positioned within recesses (268) and such that clamp arm (260) is coupled with handle assembly (230). To decouple clamp arm (260) from instrument (220), the operator overcomes the resilient bias of limbs (268) by forcing limbs (268) outwardly relative to handle assembly (230) so as to remove tabs (270) from recesses (232). This may be done by pulling clamp arm (260) away from handle assembly (230) along a transverse path with sufficient force; and/or by prying limbs (268) outwardly away from handle assembly (230) to disengage tabs (270) from recesses (232).

Although tabs (270) and recesses (232) of the present example are pill-shaped, it should be understood that tabs (270) and recesses (232) may comprise any appropriate shape or size.

A proximal end of resilient arm (264) is coupled with arcuate proximal portion (262) via a living hinge (266) and extends distally therefrom. Resilient arm (264) is resiliently biased to assume the position shown in FIG. 7A, but is configured to flex downwardly and/or upwardly as will be described in more detail below. Resilient arm (264) comprises a post (272) and a clamp pad (274). In some versions, clamp pad (274) comprises polytetrafluoroethylene (PTFE). Alternatively, clamp pad (274) may comprise any other suitable material(s) as will be apparent to those of ordinary skill in the art in view of the teachings herein. In the position shown in FIG. 7A, tissue may be positioned between a bottom surface of clamp pad (274) and an ultrasonic blade (252). Additionally, an operator may force resilient arm (264) to flex upwardly to provide a larger gap between the bottom surface of clamp pad (274) and blade (252) into which tissue may be positioned. For instance, the operator may use his or her index finger to force resilient arm (264) upwardly. At this point, the operator may force resilient arm (264) to flex downwardly into the position shown in FIG. 7B so as to capture and compress tissue between the bottom surface of clamp pad (274) and blade (252). For instance, the operator may use his or her index finger to force resilient arm (264) downwardly. As resilient arm (264) is flexed downwardly, post (272) bears against a button (236A) of a pair of buttons (236) of instrument (220), thereby depressing button (236A) and activating blade (252) as discussed above with reference to instrument (120). It should be appreciated that depression of button (236A) may correlate to generator (12) producing a "max" power setting, a "min" power setting, or any other power setting. Thus, it should be understood that forcing resilient arm (264) to flex downwardly into the position shown in FIG. 7B will simultaneously compress tissue between the bottom surface of clamp pad (274) and blade (252) and activate blade (252).

As best seen in FIGS. 4-6, blade (252) of the present example comprises a broad top surface so as to provide a broad surface for compression of tissue between blade (252) and clamp pad (274). The side surfaces of blade (252), on the other hand, are relatively thin such that the side surfaces of blade (252) may be used for cutting tissue without the assistance of clamp pad (274). It should be understood, however, that blade (252) may have any other suitable shape, including but not limited to any other ultrasonic blade shapes shown or described herein and/or shown or described in any of the references cited herein.

As best seen in FIG. 4, resilient arm (264) comprises a finger pad (276). Finger pad (276) may provide for comfort and/or non-visual positioning of the operator's finger along resilient arm (264). For instance, finger pad (276) may comprise a recessed or raised portion or a material which contrasts with a material of resilient arm (264) such that finger pad (276) may be tactilely sensed by the operator. Finger pad (276) may also include ridges, knurling, elastomeric material, and/or other features that prevent the operator's finger from sliding along clamp arm (260) as the operator presses clamp arm (260) toward handle assembly (230).

In an exemplary use, the operator may readily transition instrument (220) between two modes of operation by selectively attaching and detaching clamp arm (260). For instance, the operator may perform at least part of a surgical procedure with clamp arm (260) detached, such that the operator uses ultrasonic blade (252) like a scalpel. The operator may thus grip and use instrument (220) in a manner similar to a grip and use of instrument (120) when clamp arm (260) is detached. Within the same surgical procedure (or in a different surgical procedure), the operator may attach clamp arm (260) to handle assembly (230), then compress tissue between clamp pad (274) and ultrasonic blade (252) as described above. The operator may transition between these two modes as many times as desired within a given surgical procedure. Other suitable ways in which instrument (220) may be used will be apparent to those of ordinary skill in the art in view of the teachings herein.

B. Exemplary Ultrasonic Scalpel Instrument with Slide-on Clamp Arm

FIGS. 8-12B illustrate another exemplary ultrasonic surgical instrument (320) configured to be used as a scalpel. Instrument (320) may be used in conjunction with ultrasonic surgical system (10), which includes ultrasonic transducer (26) coupled with ultrasonic generator (12) via cable (14). Instrument (320) of this example comprises a handle assembly (330), a shaft assembly (340), and an end effector (350). Instrument (320) is configured to operate substantially similar to instrument (120) discussed above except for the differences discussed below. In particular, instrument (320) may be used to cut tissue and seal or weld tissue (e.g., a blood vessel, etc.) substantially simultaneously. Unlike instrument (120) discussed above, however, instrument (320) of the present example comprises a removable clamp arm (360, 380). As will be discussed in more detail below, clamp arms (360, 380) are configured to be selectively coupled to shaft assembly (340).

Figure 8:
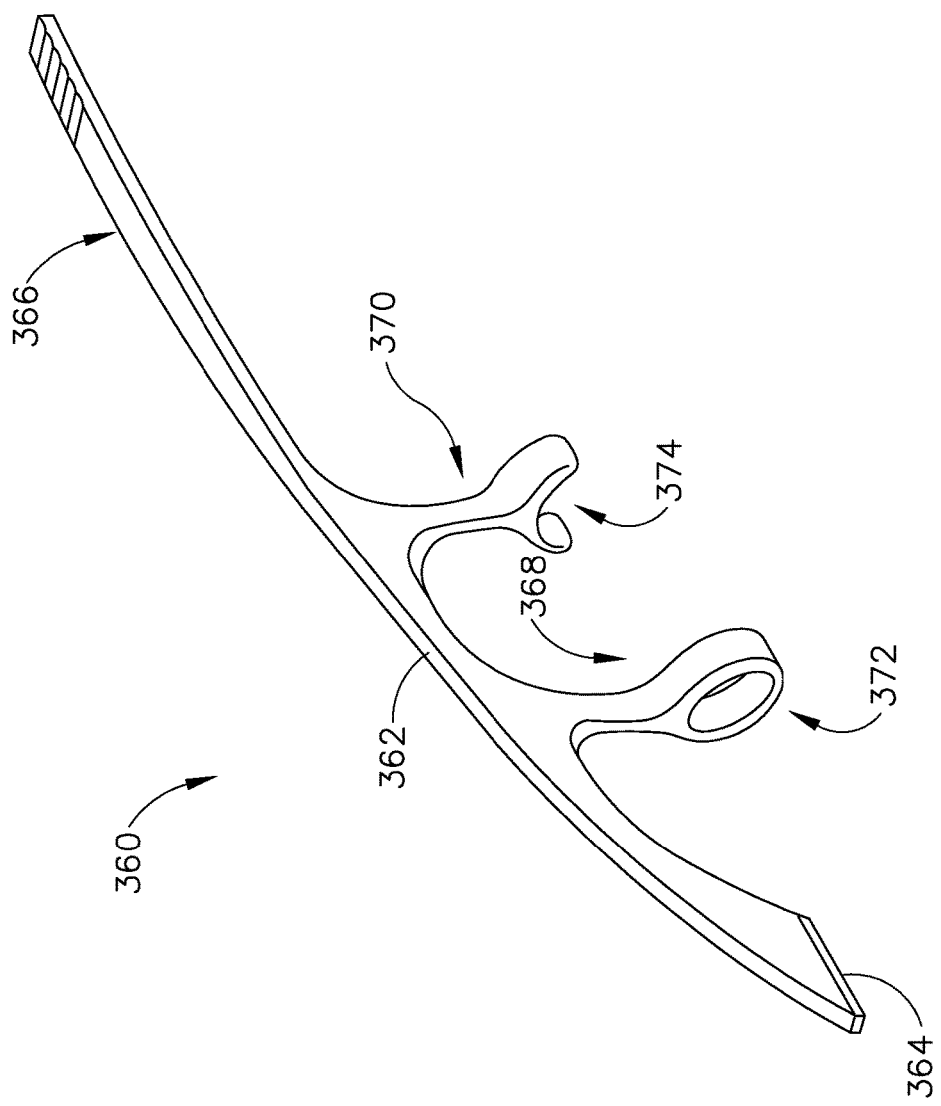
FIG. 8 depicts a perspective view of an exemplary removable clamp arm.
Figure 9:
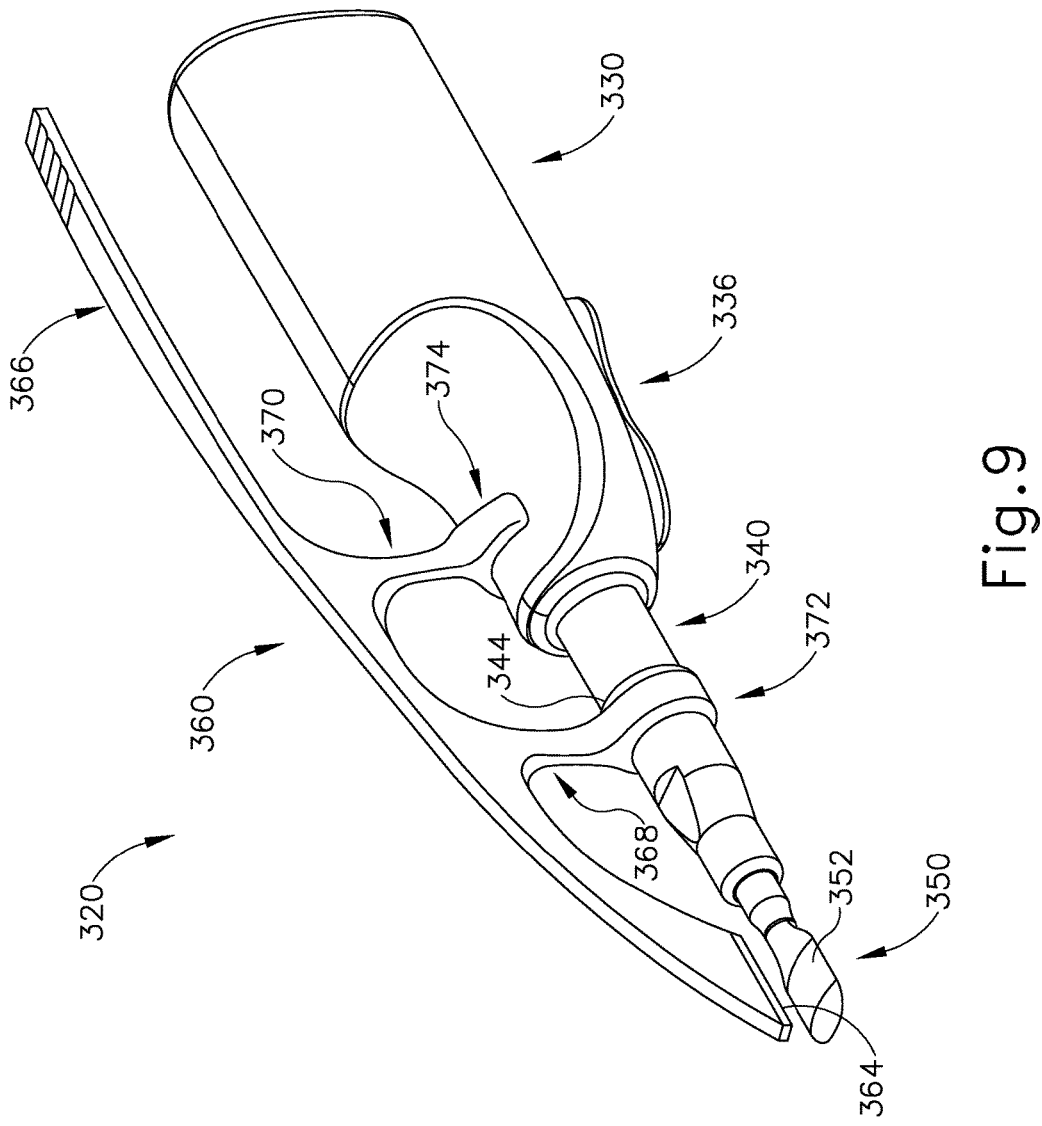
FIG. 9 depicts a perspective view of the clamp arm of FIG. 8 attached to another exemplary alternative surgical instrument.

As shown in FIGS. 8 and 9, clamp arm (360) comprises a resilient curved body member (362) having a clamp pad (364) formed at a distal end and a handle (366) formed at a proximal end. In some versions, clamp pad (364) comprises polytetrafluoroethylene (PTFE). Alternatively, clamp pad (364) may comprise any other suitable material(s) as will be apparent to those of ordinary skill in the art in view of the teachings herein. Clamp arm (360) further comprises a pair of rigid arms (368, 370) extending downwardly from a bottom surface of body member (362). Arm (368) is positioned proximal to clamp pad (364). Arm (370) is positioned proximal to arm (368). Arm (368) includes a fixing member such as a coupler sleevecoupling collar (372). As will be discussed in more detail below, coupler sleevecoupling collar (372) is configured to receive shaft assembly (340). Arm (370) includes a sliding member such as a U-shaped yoke (374). To couple clamp arm (360) with instrument (320), an operator inserts shaft assembly (340) within coupler sleevecoupling collar (372) of arm (368) to the position shown in FIG. 9. The inner diameter of coupler sleevecoupling collar (372) may be sized slightly smaller than the outer diameter of an outer sheath (342) of shaft assembly (340) to create a slight interference fit, thus securing clamp arm (360) to shaft assembly (340). The depth by which shaft assembly (340) may be inserted into coupler sleevecoupling collar (372) may be limited by, for instance, an annular flange (344) extending outwardly from an exterior surface of outer sheath (342) of shaft assembly (340). Furthermore, as will be discussed in more detail below, clamp arm (360) may be guided into position by, for instance, a magnetic guidance system. With coupler sleevecoupling collar (372) coupled about shaft assembly (340), U-shaped yoke (374) is configured to engage and bear against handle assembly (330) as shown in FIG. 9. To remove clamp arm (360) from instrument (320), the operator removes shaft assembly (340) from coupler sleevecoupling collar (372) of arm (368).

Figure 10:
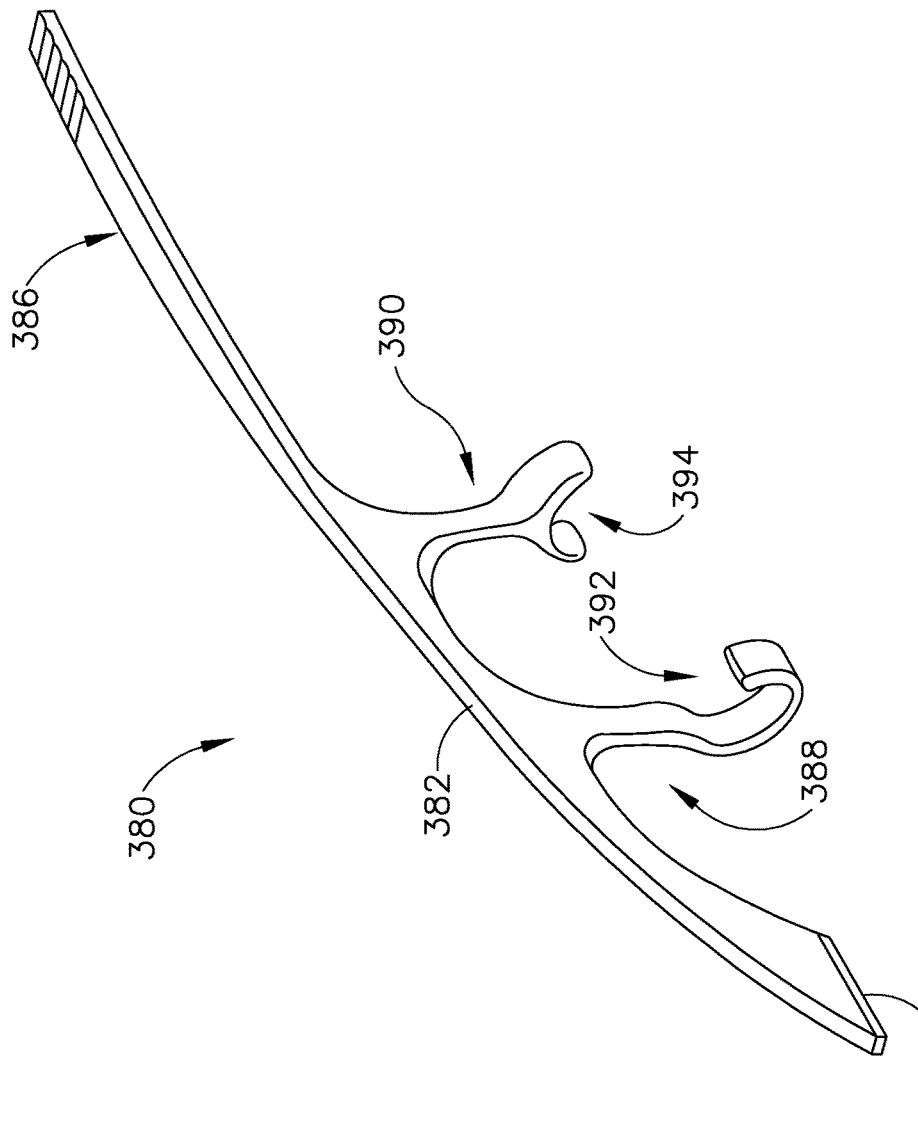
FIG. 10 depicts a perspective view of another exemplary removable clamp arm.
Figure 11:
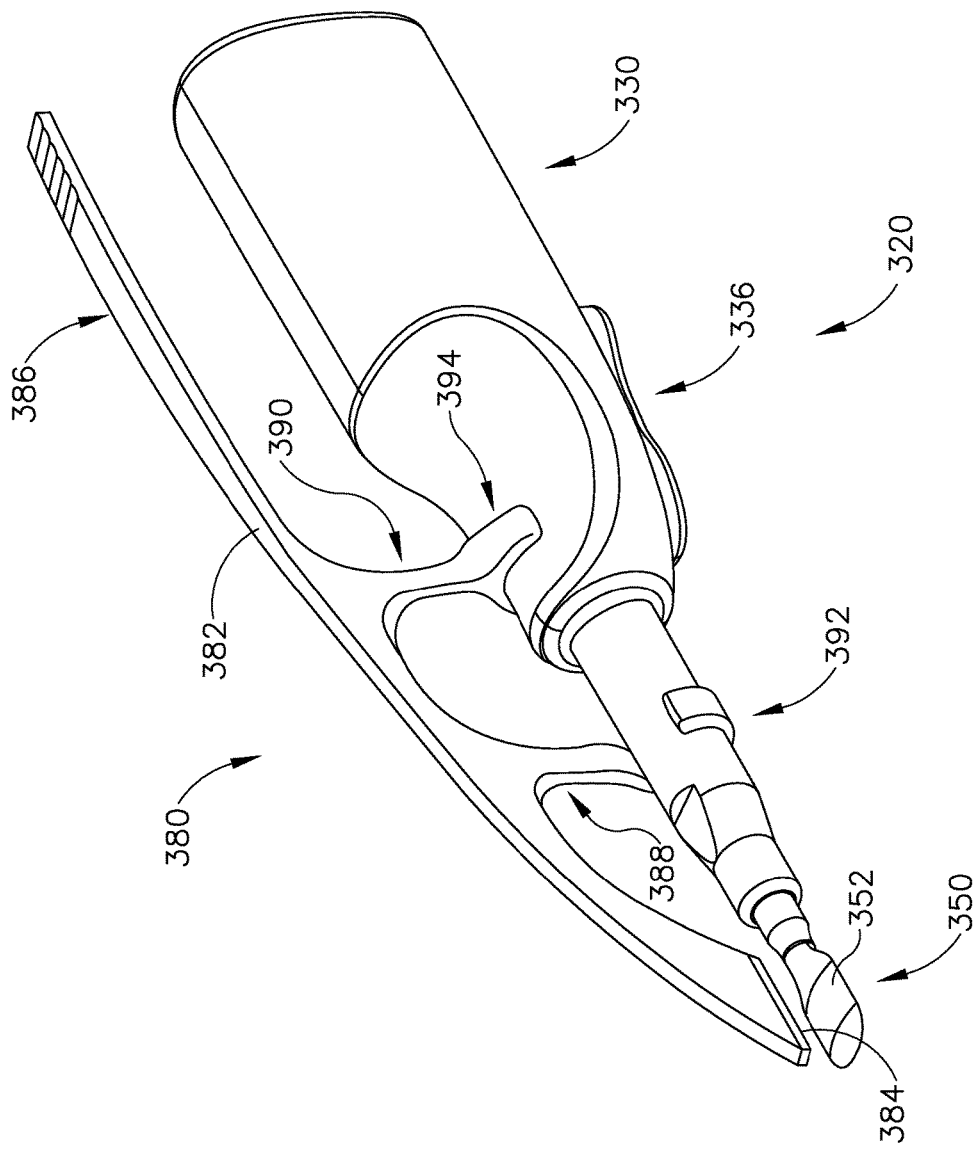
FIG. 11 depicts a perspective view of the clamp arm of FIG. 10 attached to the instrument of FIG. 9.

As shown in FIGS. 10 and 11, an exemplary alternative clamp arm (380) comprises a resilient curved body member (382) having a clamp pad (384) formed at a distal end and a handle (386) formed at a proximal end. In some versions, clamp pad (384) comprises polytetrafluoroethylene (PTFE). Alternatively, clamp pad (384) may comprise any other suitable material(s) as will be apparent to those of ordinary skill in the art in view of the teachings herein. Clamp arm (380) further comprises a pair of rigid arms (388, 390) extending downwardly from a bottom surface of body member (382). Arm (388) is positioned proximal to clamp pad (384). Arm (390) is positioned proximal to arm (388). Arm (388) includes a hook-shaped coupling feature (392). As will be discussed in more detail below, hook-shaped coupling feature (392) is configured to receive shaft assembly (340). Arm (390) includes a U-shaped yoke (394). To couple clamp arm (380) with instrument (320), the operator inserts shaft assembly (340) into hook-shaped coupling feature (392) of arm (388) to the position shown in FIG. 11. The inner diameter of hook-shaped coupling feature (392) may be sized slightly smaller than the outer diameter of an outer sheath (342) of shaft assembly (340) to create a slight interference fit, thus securing clamp arm (380) to shaft assembly (340). The depth by which shaft assembly (340) may be inserted into hook-shaped coupling feature (392) may be limited by, for instance, annular flange (344) of outer sheath (342) of shaft assembly (340). Furthermore, as will be discussed in more detail below, clamp arm (380) may be guided into position by, for instance, a magnetic guidance system. With hook-shaped coupling feature (392) coupled about shaft assembly (340), U-shaped yoke (394) is configured to engage and bear against handle assembly (330) as shown in FIG. 11. To remove clamp arm (380) from instrument (320), the operator removes shaft assembly (340) from hook-shaped coupling feature (392) of arm (388).

Figure 12A:
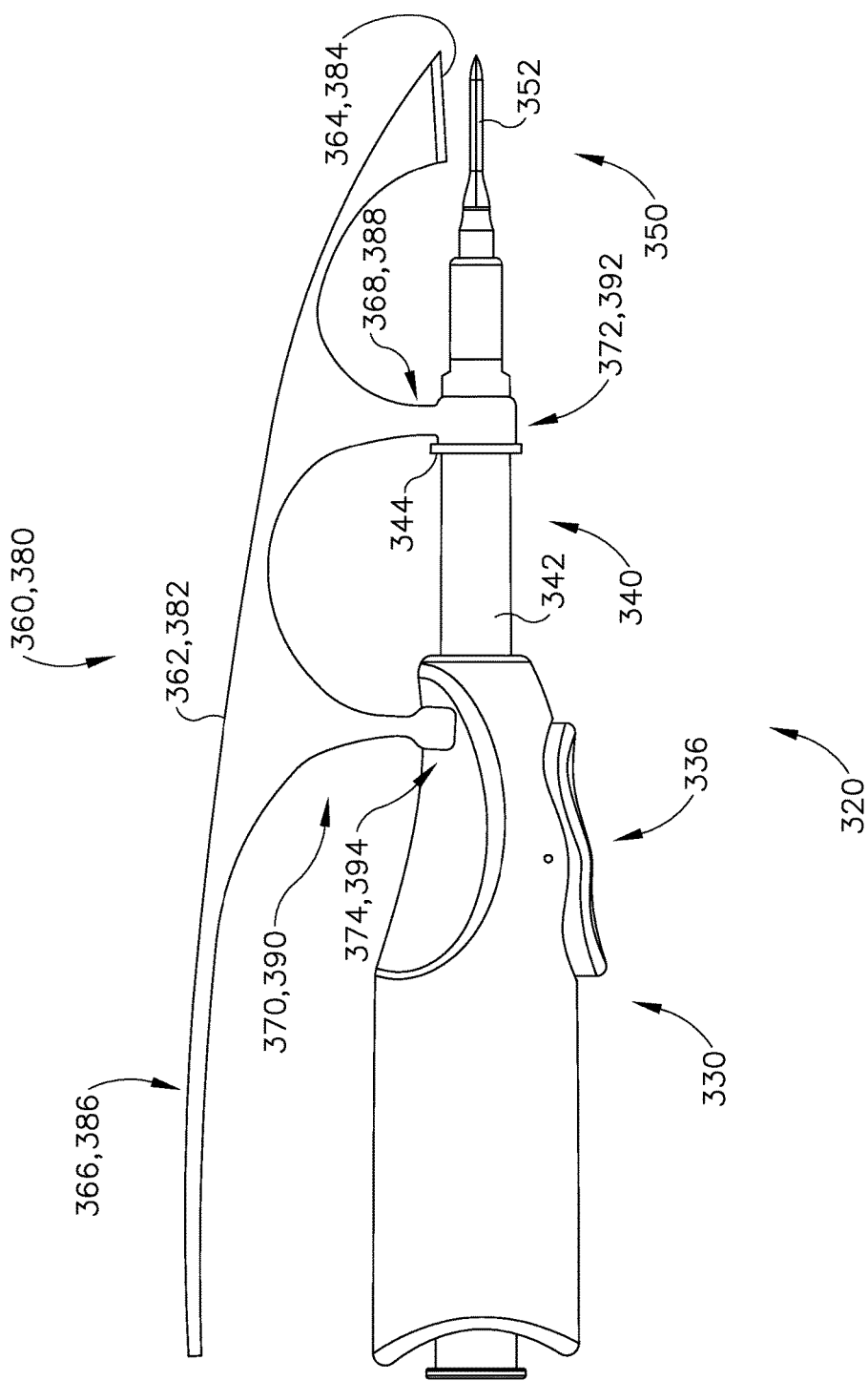
FIG. 12A depicts a side elevational view of the instrument of FIG. 9 having the clamp arm of FIG. 8 or FIG. 10 attached, with the clamp arm in an open position.
Figure 12B:
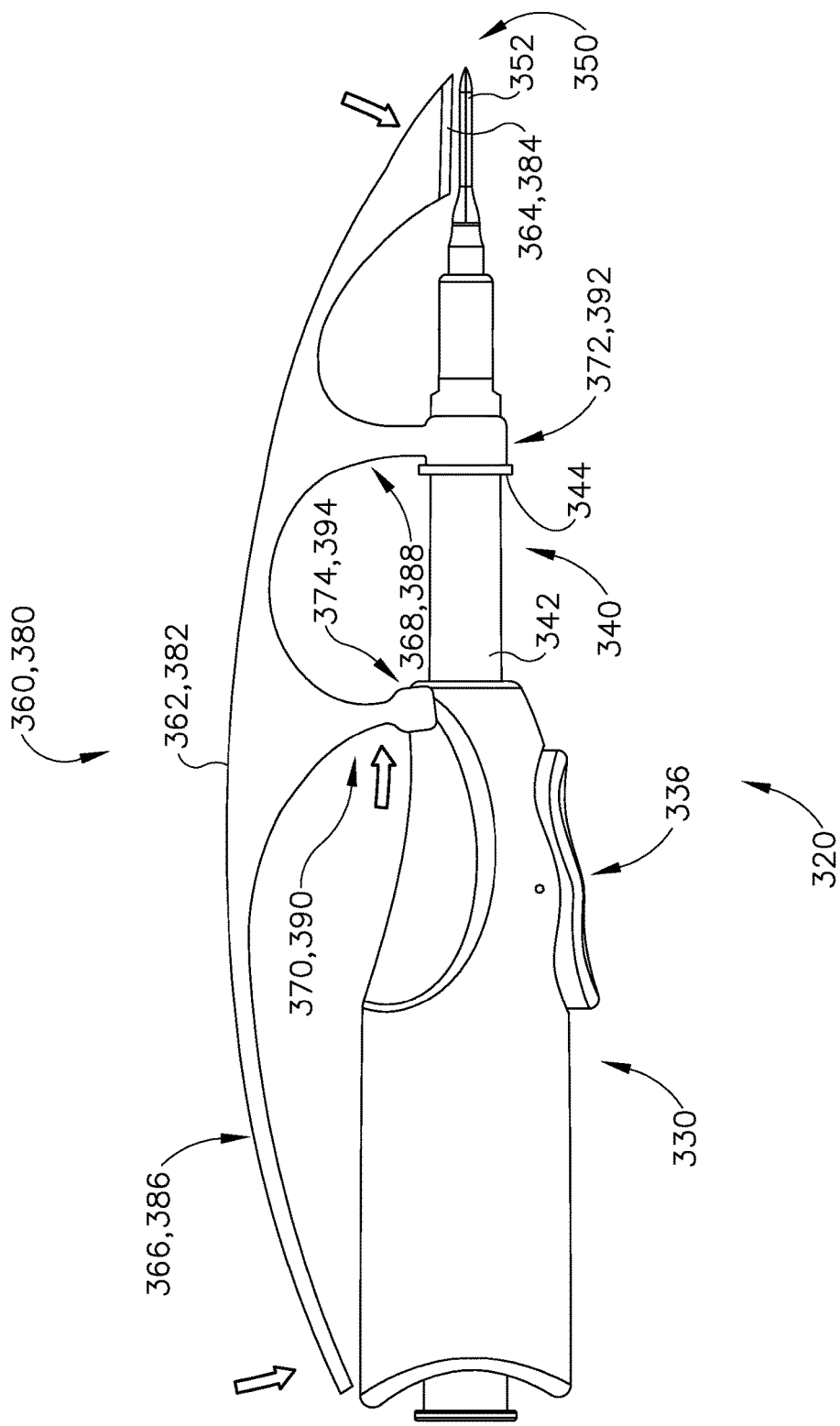
FIG. 12B depicts a side elevational view of the instrument of FIG. 9 having the clamp arm of FIG. 8 or FIG. 10 attached, with the clamp arm moved into a closed position.

Operation of clamp arms (360, 380) is shown in FIGS. 12A and 12B. With clamp arms (360,380) in the position shown in FIGS. 9, 11, and 12A, tissue may be positioned between a bottom surface of clamp pads (364, 384) and an ultrasonic blade (352) of end effector (350). With tissue positioned between a bottom surface of clamp pads (364, 384) and blade (352), the operator bears downwardly upon handles (366, 386), causing curved body member (362) to bow. As shown in FIG. 12B, as curved body member (362) bows, the distal end of curved body members (362, 382), including clamp pad (364, 384), rotates toward blade (352) so as to capture and compress tissue between the bottom surface of clamp pads (364, 384) and blade (352). Further, as curved body member (362) bows, couplers (374, 394) translate distally along handle assembly (330). It should be understood from the foregoing that clamp arms (360, 380) provide double-action leverage, with arms (368, 388) serving as one fulcrum and arms (370, 390) serving as another fulcrum.

Handle assembly (330) comprises a pair of buttons (336). Pair of buttons (336) is configured to operate substantially similar to pair of buttons (136) discussed above. For instance, as with pair of buttons (136) discussed above, when the operator depresses one button of the pair of buttons (336), generator (12) may respond with a certain energy level, such as a maximum power setting; and when the operator depresses another button of the pair of buttons (336), generator (12) may respond with another energy level, such as a minimum power setting. It should be appreciated that as the operator uses instrument (320) with clamp arms (360, 380) attached, the operator may readily depress the buttons of pair of buttons (336) using his or her index finger or thumb to thereby activate blade (352). Thus, it should be appreciated that the operator may simultaneously activate blade (352) and compress tissue between the bottom surface of clamp pads (364, 384) and blade (352).

As with blade (252) discussed above, and as best seen in FIGS. 9, 11, and 12A-12B, blade (352) of the present example comprises a broad top surface so as to provide a broad surface for compression of tissue between blade (352) and clamp pads (364, 384). The side surfaces of blade (352), on the other hand, are relatively thin such that the side surfaces of blade (352) may be used for cutting tissue without the assistance of clamp pads (364, 384). It should be understood, however, that blade (352) may have any other suitable shape, including but not limited to any other ultrasonic blade shapes shown or described herein and/or shown or described in any of the references cited herein.

It should also be understood that clamp arms (360, 380) may be rotated about the longitudinal axis of shaft assembly (340) to any appropriate rotational position, allowing clamp pads (364, 384) to compress tissue against ultrasonic blade (352) at various selected angular positions about ultrasonic blade (352). Alternatively, outer sheath (342) of shaft assembly (340) may be keyed into couplers (372, 392) of clamp arms (360, 380) to thereby prevent rotation as will be discussed in more detail below.

In an exemplary use, the operator may readily transition instrument (320) between two modes of operation by selectively attaching and detaching clamp arms (360, 380). For instance, the operator may perform at least part of a surgical procedure with clamp arms (360, 380) detached, such that the operator uses ultrasonic blade (352) like a scalpel. The operator may thus grip and use instrument (320) in a manner similar to a grip and use of instrument (120) when clamp arms (360, 380) are detached. Within the same surgical procedure (or in a different surgical procedure), the operator may attach clamp arms (360, 380) to shaft assembly (340), then compress tissue between clamp pads (364, 384) and ultrasonic blade (352) as described above. The operator may transition between these two modes as many times as desired within a given surgical procedure. Other suitable ways in which instrument (320) may be used will be apparent to those of ordinary skill in the art in view of the teachings herein.

C. Exemplary Ultrasonic Scalpel Instrument with Slide-on Clamp Arm and Magnetic Guidance System FIGS. 13-16C illustrate yet another exemplary ultrasonic surgical instrument (420) configured to be used as a scalpel. Instrument (420) may be used in conjunction with ultrasonic surgical system (10), which includes ultrasonic transducer (26) coupled with ultrasonic generator (12) via cable (14). Instrument (420) of this example comprises a handle assembly (430), a shaft assembly (440), and an end effector (450). Instrument (420) is configured to operate substantially similar to instrument (120) discussed above except for the differences discussed below. In particular, instrument (420) may be used to cut tissue and seal or weld tissue (e.g., a blood vessel, etc.) substantially simultaneously. Unlike instrument (120) discussed above, however, instrument (420) of the present example comprises a removable clamp arm (460). As will be discussed in more detail below, clamp arm (460) is configured to be selectively coupled to shaft assembly (440).

As best seen in FIG. 13, clamp arm (460) comprises a resilient curved body member (462) having a clamp pad (464) formed at a distal end and a handle (466) formed at a proximal end. In some versions, clamp pad (464) comprises polytetrafluoroethylene (PTFE). Alternatively, clamp pad (464) may comprise any other suitable material(s) as will be apparent to those of ordinary skill in the art in view of the teachings herein. Clamp arm (460) further comprises a pair of rigid arms (468, 470) extending downwardly from a bottom surface of body member (462). Arm (468) is positioned proximal to clamp pad (464). Arm (470) is positioned proximal to arm (468). Arm (468) includes an elongate coupling rail (472). Elongate coupling rail (472) of the present example has a T-shaped cross-sectional profile defined by a web portion (474) and a flange portion (476). As will be discussed in more detail below, an outer sheath (442) of shaft assembly (440) is configured to receive elongate coupling rail (472).

Arm (470) includes a U-shaped yoke (478). Outer sheath (442) comprises an elongate projection (444) having an elongate slot (446). Slot (446) has a T-shaped cross-sectional profile that is sized slightly larger than the T-shaped cross-sectional profile of coupling rail (472), such that coupling rail (472) may be received within slot (446). To couple clamp arm (460) with instrument (420), an operator inserts coupling rail (472) within slot (446) of outer sheath (442) to the position shown in FIG. 14.

Shaft assembly (440) further comprises a magnetic guidance system. The magnetic guidance system comprises an elongate magnet (448) disposed within outer sheath (442) beneath a bottom surface of slot (446) of projection (444), as best seen in FIG. 15. Coupling rail (472) comprises a magnet and/or a ferrous metal such that as coupling rail (472) is inserted within slot (446), magnet (448) repels coupler (472) until coupling rail (472) is positioned at a point relative to magnet (448) where the magnet (448) attracts coupling rail (472), thus guiding clamp arm (460) to a particular longitudinal position relative to shaft assembly (440) and securing clamp arm (460) to shaft assembly (440). To remove clamp arm (460) from instrument (420), the operator removes coupling rail (472) from slot (446) of projection (444) by urging clamp arm (460) distally with enough force to overcome the magnetic attraction of magnet (448).

While clamp arm (460) of the present example is described as being secured to shaft assembly (440) by the magnetic guidance system, instrument (420) may omit the magnetic guidance system altogether. For instance, slot (446) may be sized slightly smaller than the coupling rail (472) to create a slight interference fit, thus securing clamp arm (460) to shaft assembly (440). Further, the depth by which shaft assembly (340) may be inserted into slot (446) may be limited by, for instance, closing off an end of slot (446). Slot (446) and coupling rail (472) may also comprise complementary snap fit features, detent features, and/or various other kinds of features to provide a suitable (and in some versions, removable) coupling between clamp arm (460) and shaft assembly (440).

Figure 16A:
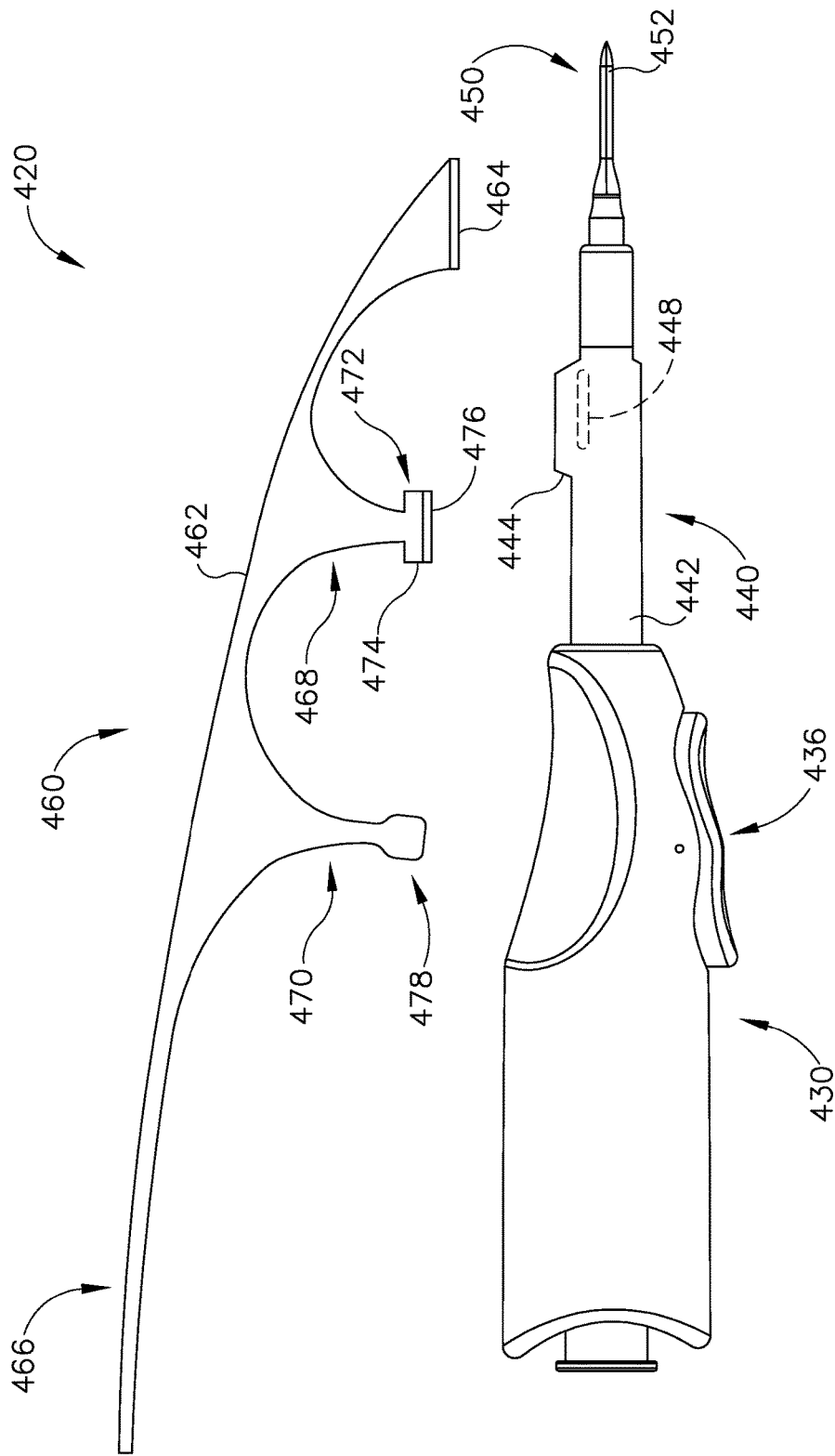
FIG. 16A depicts a partially exploded side elevational view of the clamp arm of FIG. 13 and the instrument of FIG. 14.
Figure 16B:
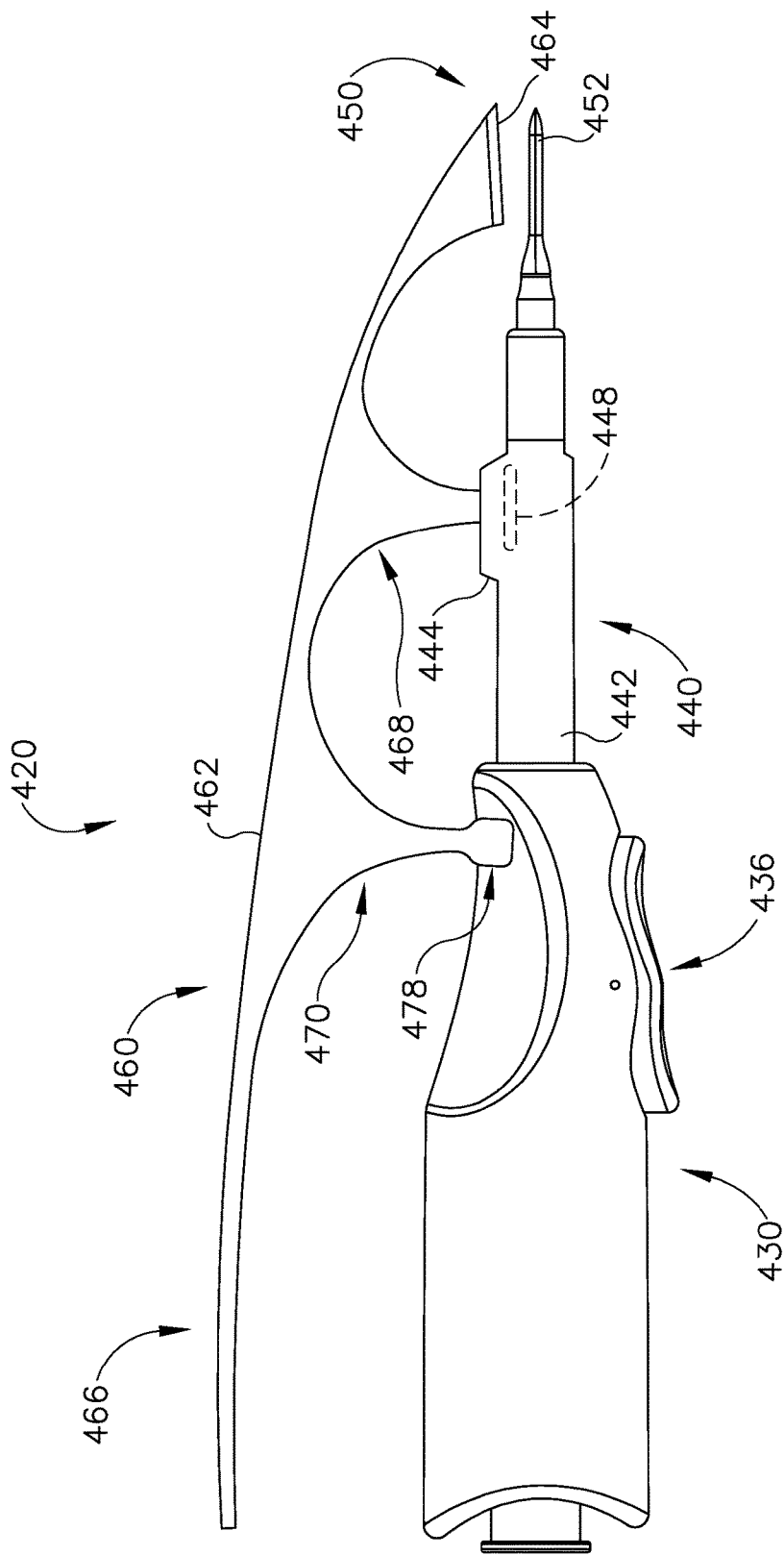
FIG. 16B depicts a side elevational view of the clamp arm of FIG. 13 attached to the instrument of FIG. 14, with the clamp arm in an open position.
Figure 16C:
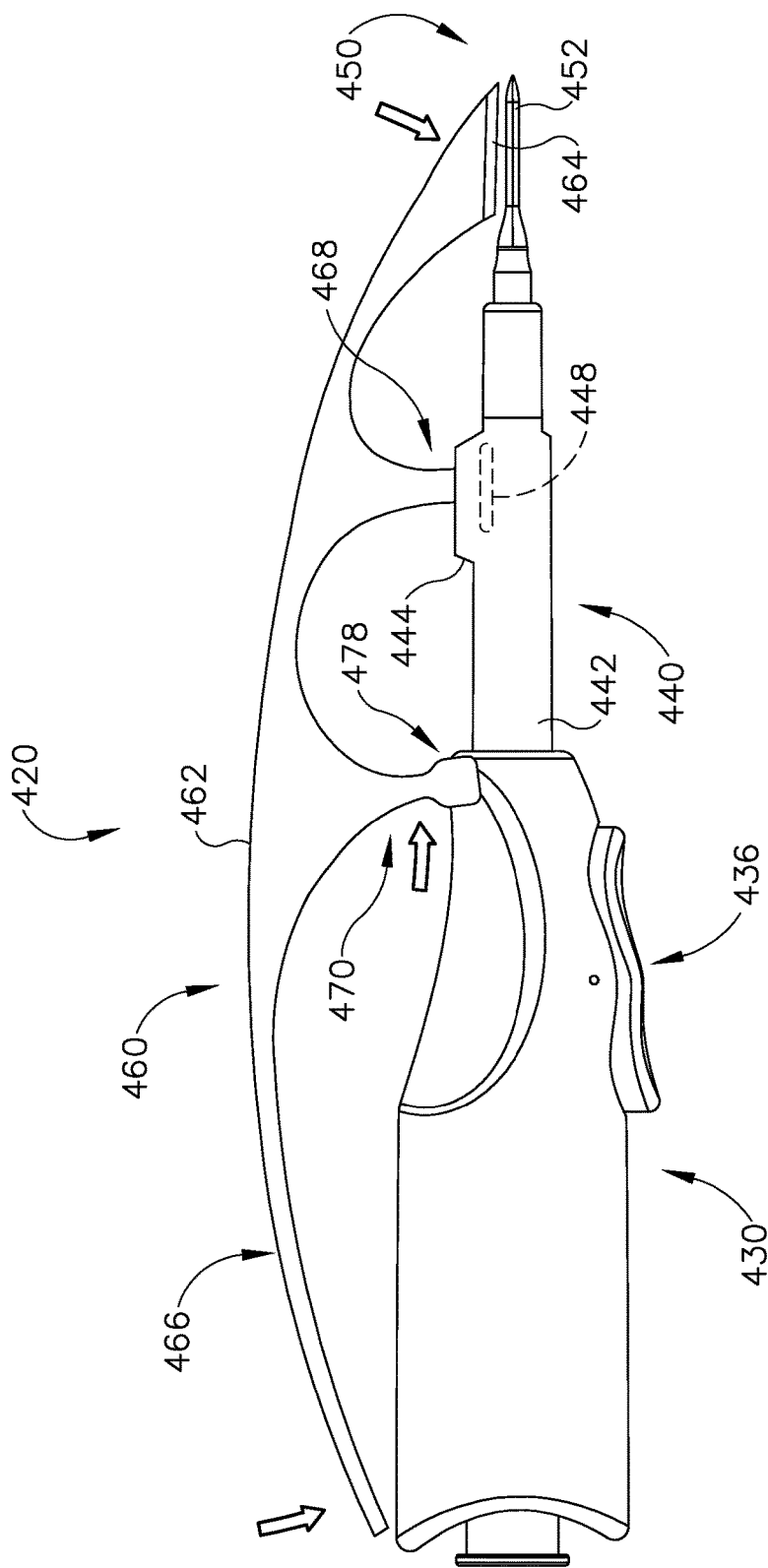
FIG. 16C depicts a side elevational view of the clamp arm of FIG. 13 attached to the instrument of FIG. 14, with the clamp arm moved into a closed position.
Figure 17:
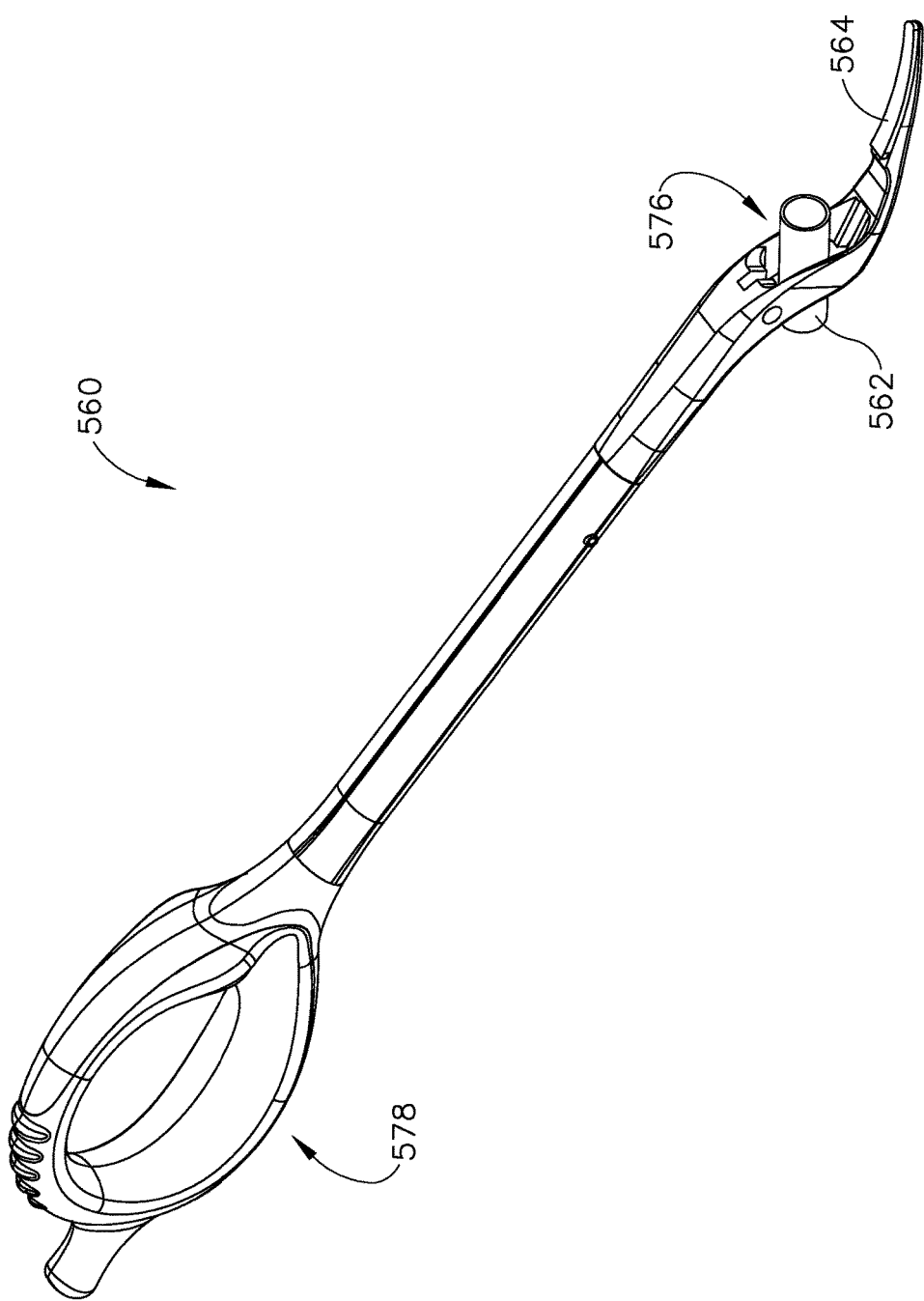
FIG. 17 depicts a perspective view of yet another exemplary alternative removable clamp arm.
Figure 18:
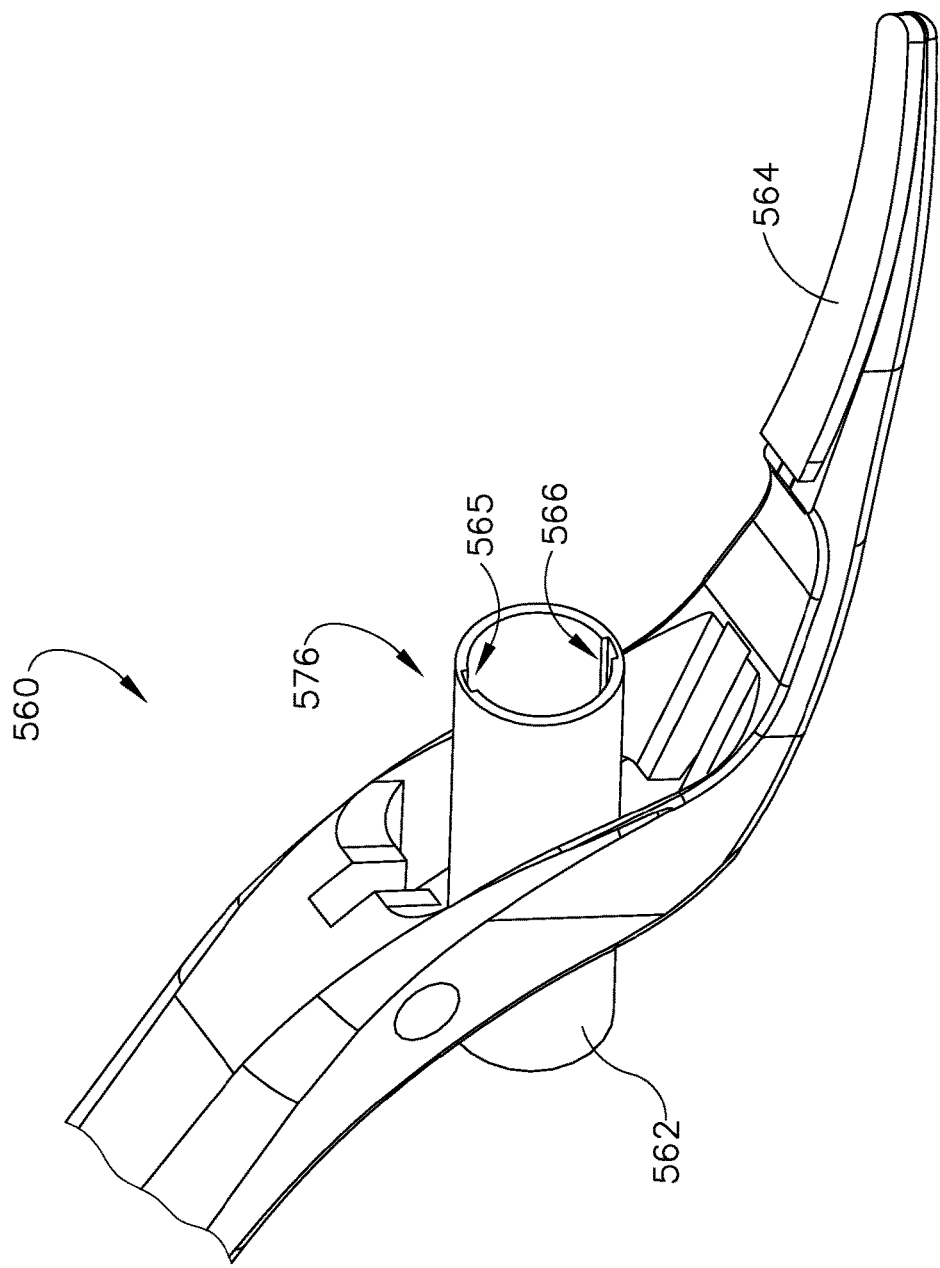
FIG. 18 depicts a perspective view of a distal end of the clamp arm of FIG. 17.
Figure 19:
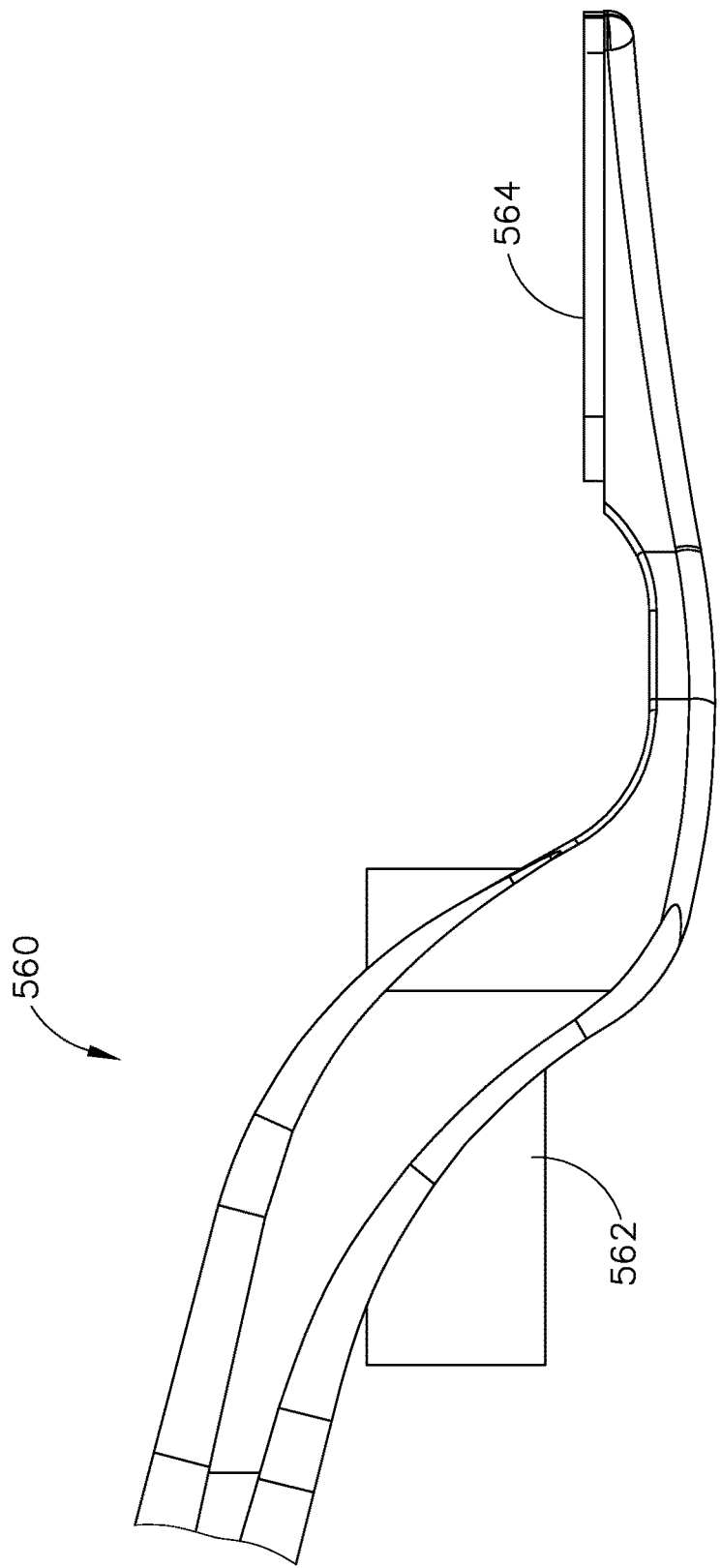
FIG. 19 depicts a side elevational view of the distal end of the clamp arm of FIG. 17.

Operation of clamp arm (460) is shown in FIGS. 16A-16C. Clamp arm (460) is guided into position and secured to shaft assembly (440) by the magnetic guidance system as described above. With clamp arm (460) in the position shown in FIGS. 15 and 16B, tissue may be positioned between a bottom surface of clamp pad (464) and an ultrasonic blade (452) of end effector (450). With tissue positioned between a bottom surface of clamp pad (464) and blade (452) the operator bears downwardly upon handle (466) causing curved body member (462) to bow. As shown in FIG. 16C, as curved body member (462) bows, the distal end of curved body member (462), including clamp pad (464), rotates toward blade (452) so as to capture and compress tissue between the bottom surface of clamp pad (464) and blade (452). Further, as curved body member (462) bows, yoke (478) translates distally along handle assembly (430). It should be understood from the foregoing that clamp arm (460) provides double-action leverage, with arm (468) serving as one fulcrum and arm (470) serving as another fulcrum.

Handle assembly (430) comprises a pair of buttons (436). Pair of buttons (436) is configured to operate substantially similar to pair of buttons (136) discussed above. For instance, as with pair of buttons (136) discussed above, when the operator depresses one button of the pair of buttons (436), generator (12) may respond with a certain energy level, such as a maximum power setting; and when the operator depresses another button of the pair of buttons (436), generator (12) may respond with another energy level, such as a minimum power setting. It should be appreciated that as the operator uses instrument (420) with clamp arm (460) attached, the operator may readily depress the buttons of pair of buttons (436) using his or her index finger or thumb to thereby activate blade (452). Thus, it should be appreciated that the operator may simultaneously activate blade (452) and compress tissue between the bottom surface of clamp pad (464) and blade (452).

As with blades (252, 352) discussed above, and as best seen in FIGS. 15 and 16A-16C, blade (452) of the present example comprises a broad top surface so as to provide a broad surface for compression of tissue between blade (452) and clamp pad (464). The side surfaces of blade (452), on the other hand, are relatively thin such that the side surfaces of blade (452) may be used for cutting tissue without the assistance of clamp pad (464). It should be understood, however, that blade (452) may have any other suitable shape, including but not limited to any other ultrasonic blade shapes shown or described herein and/or shown or described in any of the references cited herein.

In an exemplary use, the operator may readily transition instrument (420) between two modes of operation by selectively attaching and detaching clamp arm (460). For instance, the operator may perform at least part of a surgical procedure with clamp arm (460) detached, such that the operator uses ultrasonic blade (452) like a scalpel. The operator may thus grip and use instrument (420) in a manner similar to a grip and use of instrument (120) when clamp arm (460) is detached. Within the same surgical procedure (or in a different surgical procedure), the operator may attach clamp arm (460) to shaft assembly (440), then compress tissue between clamp pad (464) and ultrasonic blade (452) as described above. The operator may transition between these two modes as many times as desired within a given surgical procedure. Other suitable ways in which instrument (420) may be used will be apparent to those of ordinary skill in the art in view of the teachings herein.

D. Exemplary Ultrasonic Scalpel Instrument with Keyed Coupling

FIGS. 17-24C illustrate a clamp arm (560) and various features of yet another exemplary ultrasonic surgical instrument (520) configured to be used as a scalpel. Instrument (520) may be used in conjunction with ultrasonic surgical system (10), which includes ultrasonic transducer (26) coupled with ultrasonic generator (12) via cable (14). Instrument (520) of this example comprises a handle assembly (530), a shaft assembly (540), and an end effector (550). Instrument (520) is configured to operate substantially similar to instrument (120) discussed above except for the differences discussed below. In particular, instrument (520)

may be used to cut tissue and seal or weld tissue (e.g., a blood vessel, etc.) substantially simultaneously. Unlike instrument (120) discussed above, however, instrument (520) of the present example comprises a removable clamp arm (560). As will be discussed in more detail below, clamp arm (560) is configured to be selectively coupled to shaft assembly (540).

Figure 20:
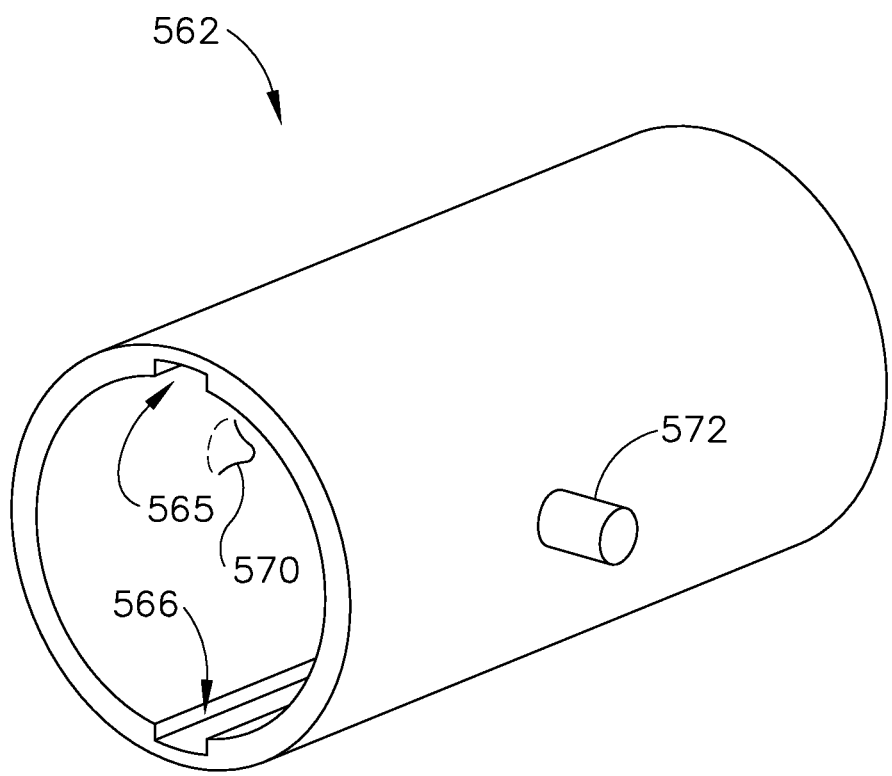
FIG. 20 depicts a perspective view of an exemplary coupler sleeve of the clamp arm of FIG. 17.

Clamp arm (560) comprises a hollow, cylindrical coupler sleeve (562). As will be discussed in more detail below, coupler sleeve (562) is configured to receive and selectively couple with shaft assembly (540). As best seen in FIG. 20, coupler sleeve (562) comprises a pair of elongate channels (565, 566) formed in an interior surface of coupler sleeve (562). Channels (565, 566) include a first channel (565) formed in a top portion of the interior surface of coupler sleeve (562) and opening downwardly; and a second channel (566) formed in a bottom portion of the interior surface of coupler sleeve (562) and opening upwardly. Coupler sleeve (562) further comprises a pair of detent recesses (568, 570) formed in opposing sides of the interior surface of coupler sleeve (562) and a pair of pins (572, 574) extending outwardly from opposing sides of an exterior surface of coupler sleeve (562).

Figure 22:
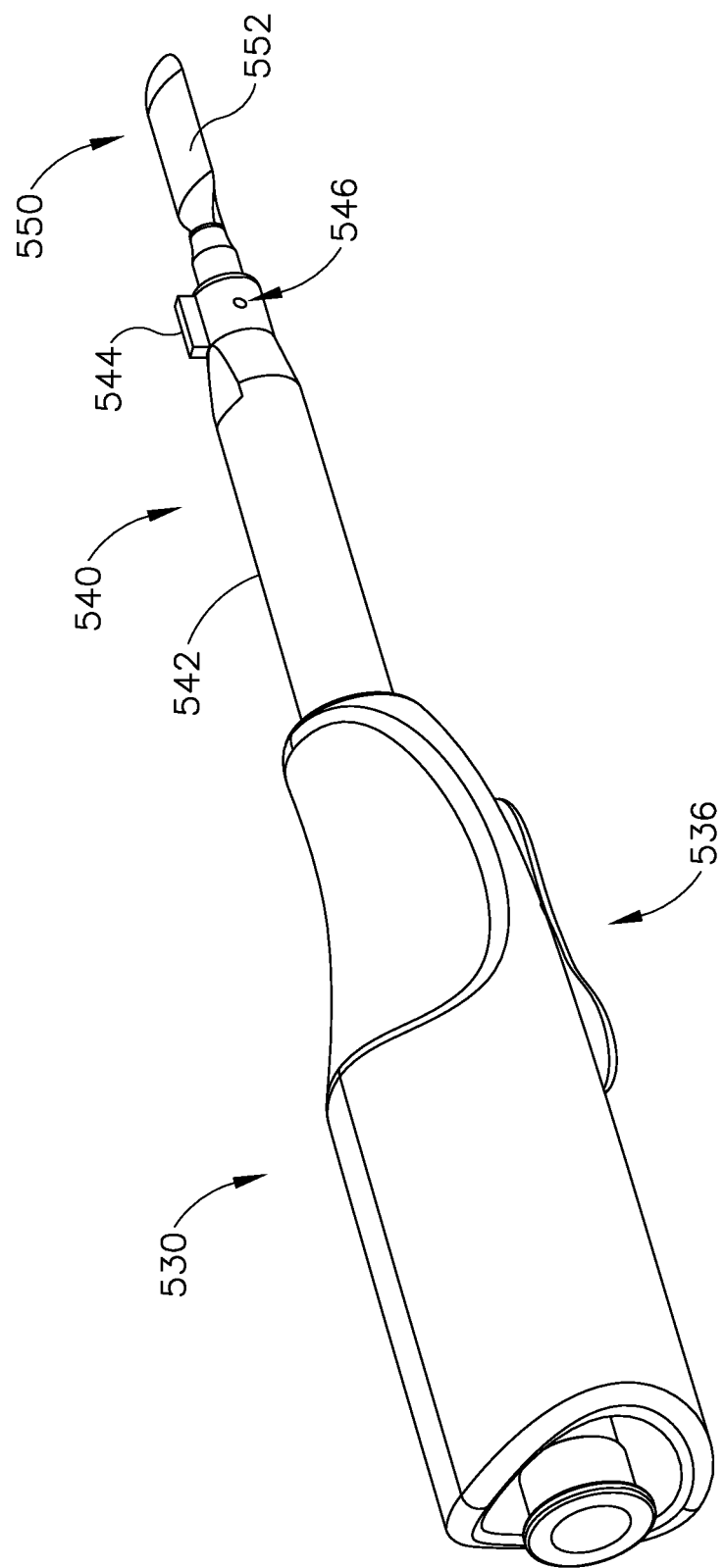
FIG. 22 depicts a perspective view of yet another exemplary alternative surgical instrument.
Figure 23:
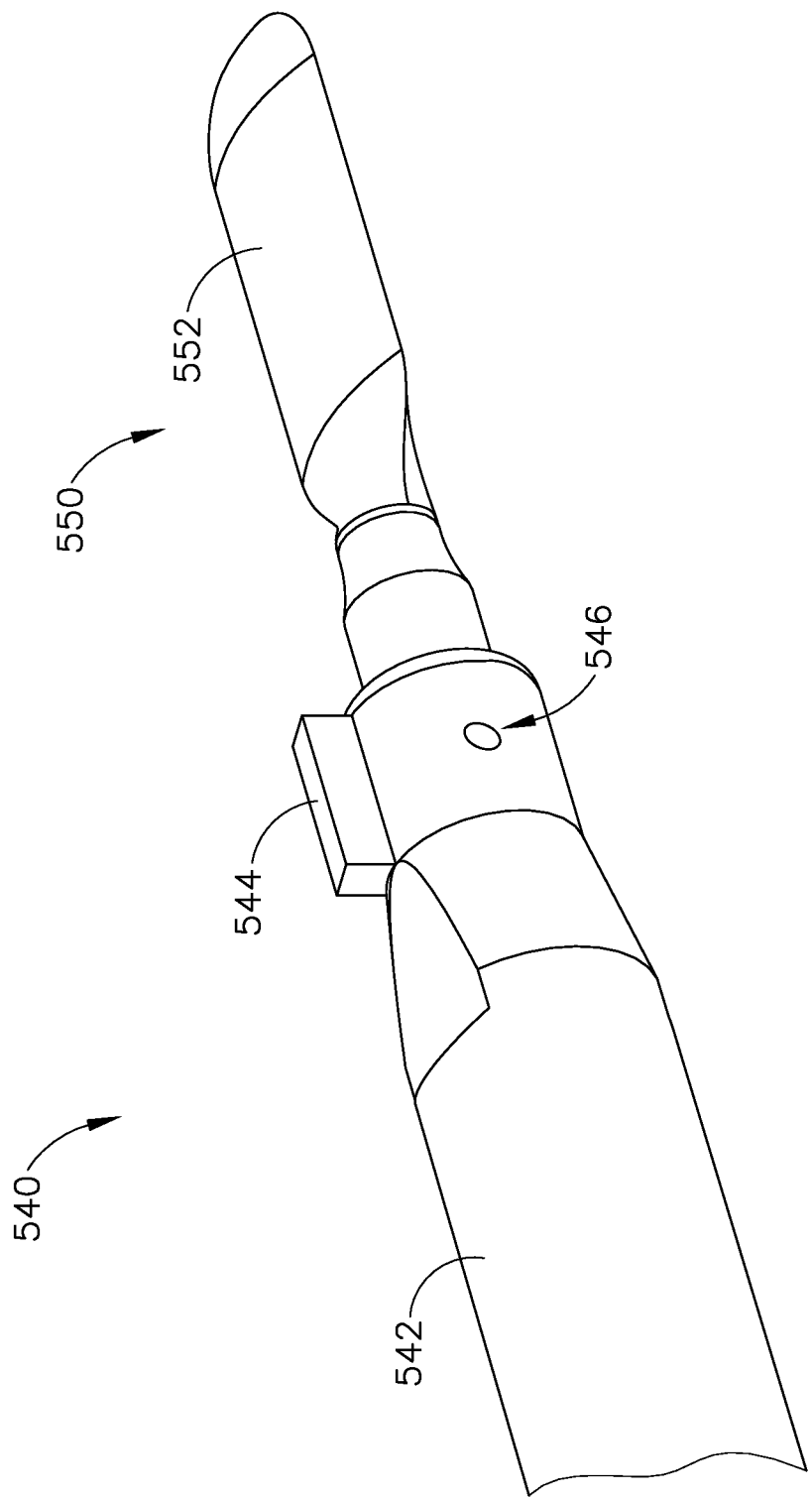
FIG. 23 depicts a perspective view of a distal end of the instrument of FIG. 22.

As shown in FIGS. 22-23, an outer sheath (542) of shaft assembly (540) comprises an elongate rectangular projection (544) extending upwardly from an exterior surface of outer sheath (542) and a pair of detent protrusions (546, 548) extending inwardly from opposing sides of the exterior surface of outer sheath (542). Channels (565, 566) are configured to receive projection (544) such that projection (544) may be keyed into a channel (565, 566) to thereby prevent rotation of coupler sleeve (562) (and thus clamp arm (560)) about the longitudinal axis of shaft assembly (540) when coupler sleeve (562) is disposed about shaft assembly (540). It should be understood that projection (544) may be disposed within either channel (565, 566) so as to allow an operator to orient coupler sleeve (562) (and thus clamp arm (560)) at multiple angular positions about the longitudinal axis of shaft assembly (540), 180° from one another. It will also be appreciated, however, that any number of channels oriented at any appropriate rotational position relative to one another may be formed in the interior surface of coupler sleeve (562) so as to allow coupler sleeve (562) (and thus clamp arm (560)) to be oriented at any appropriate angular position about the longitudinal axis of shaft assembly (540).

Detent recesses (568, 570) of coupler sleeve (562) are configured to receive detent protrusions (546, 548) of outer sheath (542) so as to selectively prevent longitudinal movement of coupler sleeve (562) (and thus clamp arm (560)) relative to shaft assembly (540). It should be appreciated that engagement of detent protrusions (546, 548) and detent recesses (568, 570) may also provide audible and/or tactile feedback to the operator signaling proper orientation and/or longitudinal positioning of clamp arm (560) relative to shaft assembly (540).

Coupler sleeve (562) is disposed within a passageway (576) of clamp arm (560). Coupler sleeve (562) is pivotably coupled to clamp arm (560) within through-bore (576) via pins (572, 574) such that clamp arm (560) is pivotable toward and away from an ultrasonic blade (552) of shaft assembly (540) to thereby clamp and compress tissue between a clamp pad (564) of clamp arm (560) and ultrasonic blade (552). In some versions, clamp pad (564) comprises polytetrafluoroethylene (PTFE). Alternatively, clamp pad (564) may comprise any other suitable material(s) as will be apparent to those of ordinary skill in the art in view of the teachings herein.

Figure 24A:
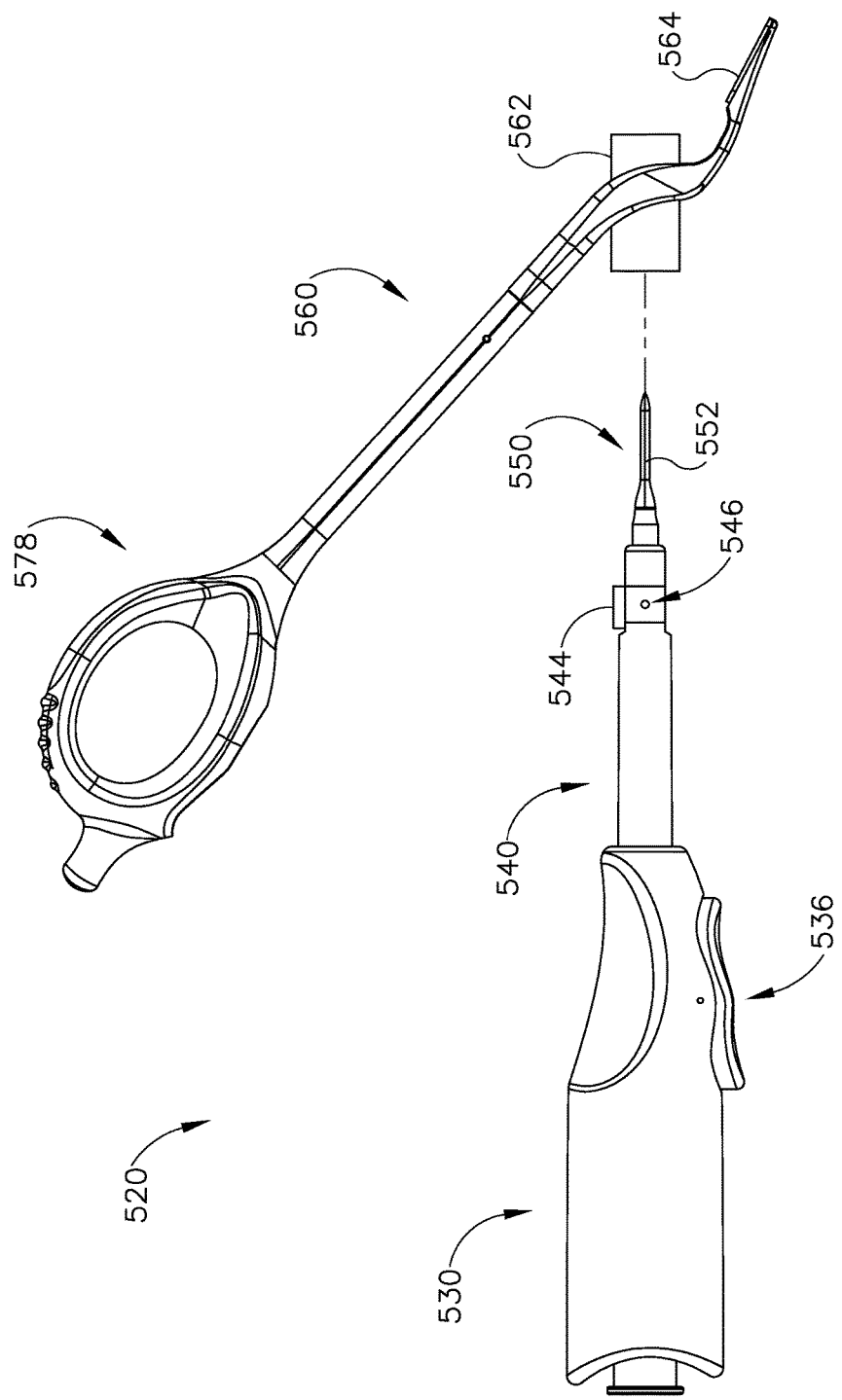
FIG. 24A depicts a partially exploded side elevational view of the clamp arm of FIG. 17 and the instrument of FIG. 22.
Figure 24B:
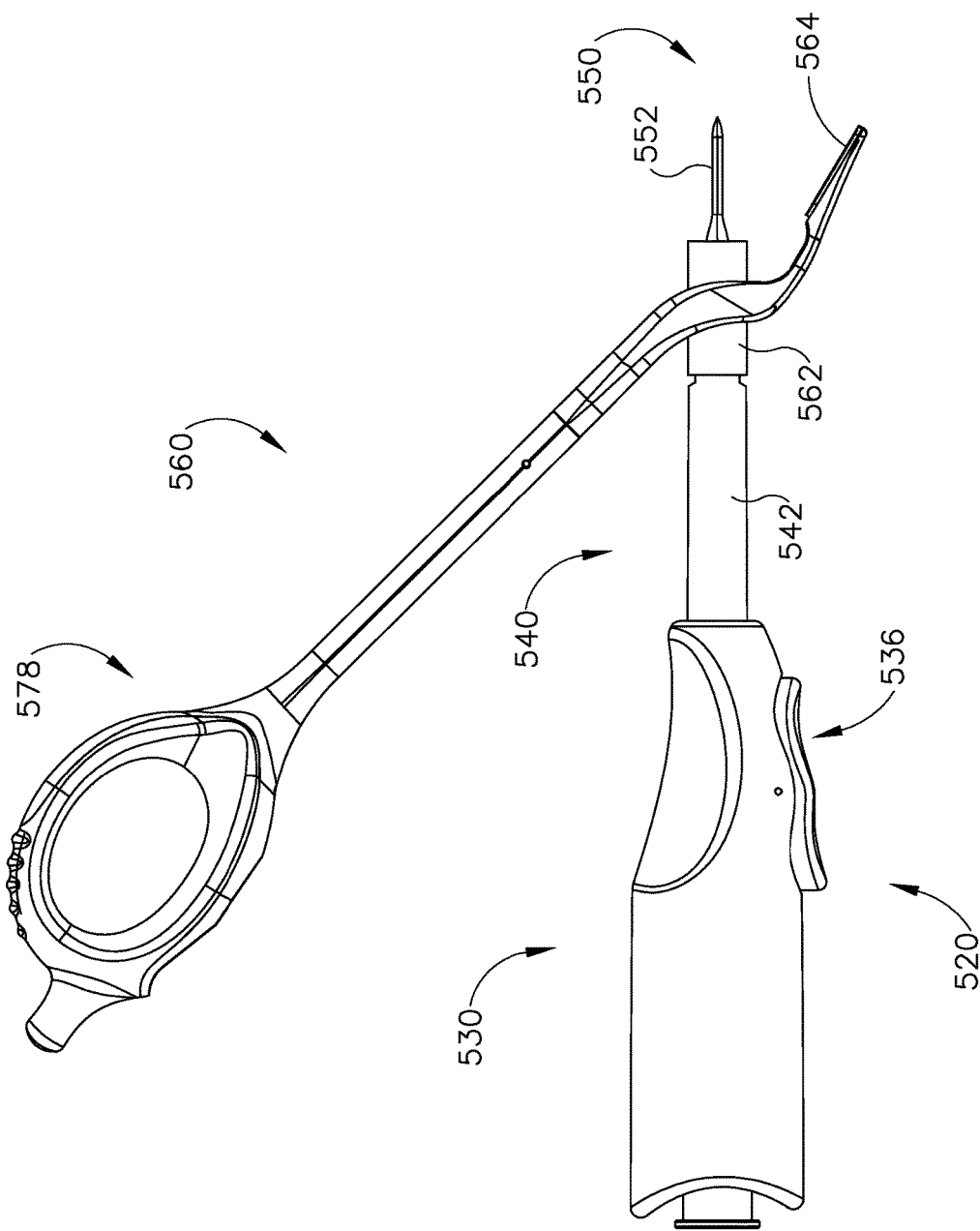
FIG. 24B depicts a side elevational view of the clamp arm of FIG. 17 attached to the instrument of FIG. 22, with the clamp arm in an open position.
Figure 24C:
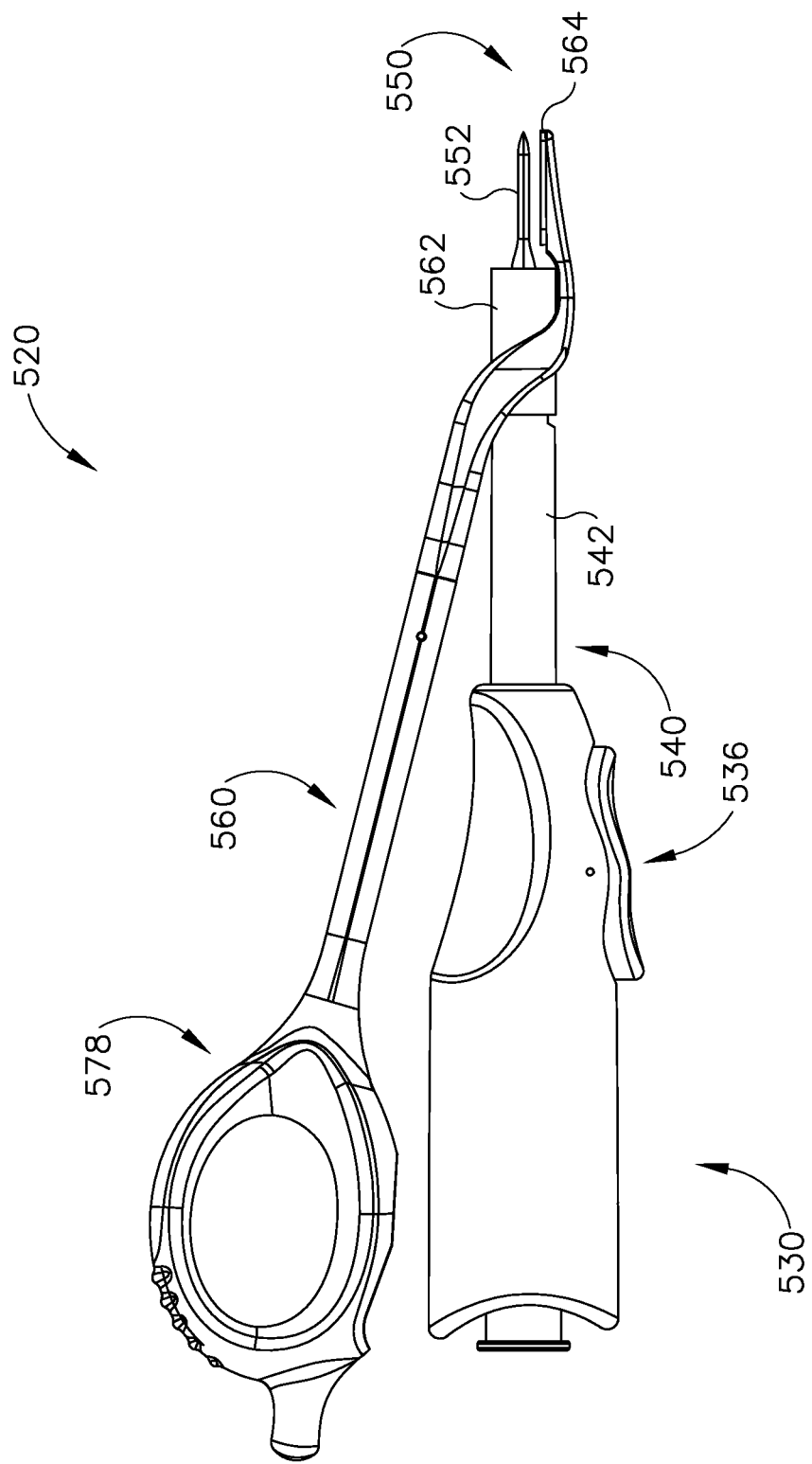
FIG. 24C depicts a side elevational view of the clamp arm of FIG. 17 attached to the instrument of FIG. 22, with the clamp arm moved into a closed position.
Figure 25:
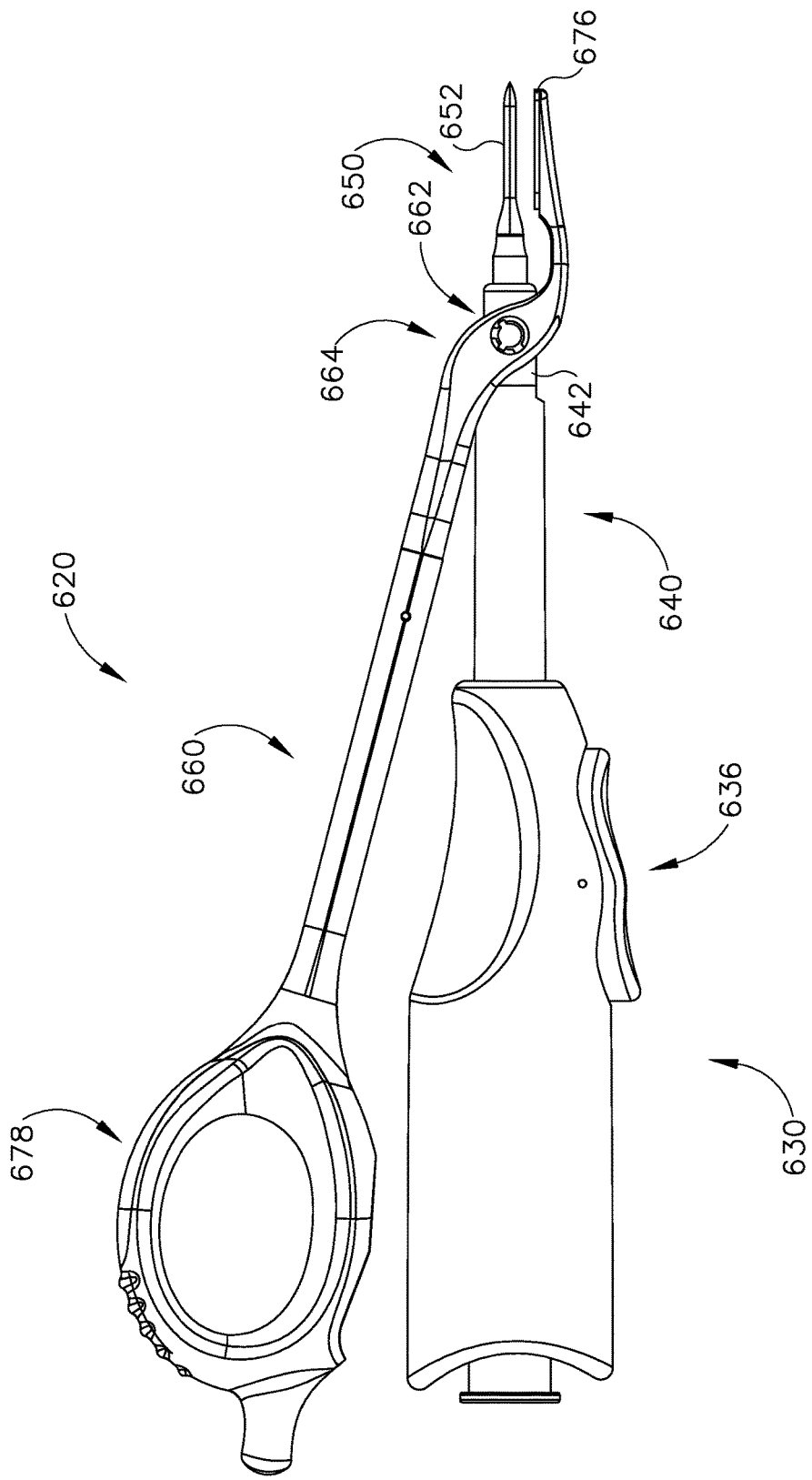
FIG. 25 depicts a side elevational view of yet another exemplary alternative surgical instrument having a removable clamp arm.
Figure 26:
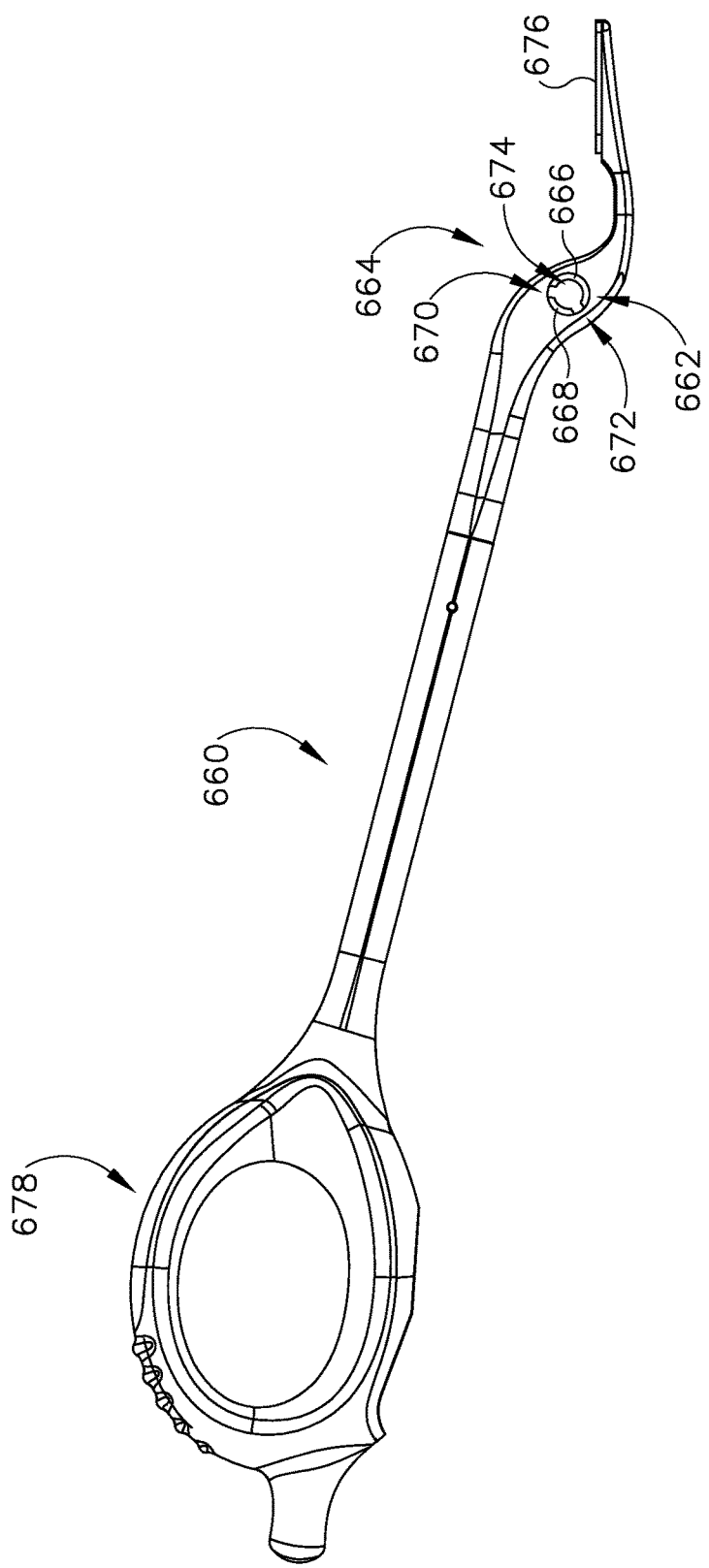
FIG. 26 depicts a side elevational view of the clamp arm of FIG. 25.

To couple clamp arm (560) with instrument (520), the operator inserts shaft assembly (540) within coupler sleeve (562) of clamp arm (560) to the position shown in FIG. 24B. In this position, projection (544) has been keyed into a channel (565, 566) to thereby prevent rotation of clamp arm (560) about the longitudinal axis of shaft assembly (540); and detent protrusions (546, 548) have engaged detent recesses (568, 570) so as to prevent longitudinal movement of clamp arm (560) relative to shaft assembly (540). At this point, the operator may use instrument (520), including clamp arm (560), as he or she would a pair of surgical forceps to capture tissue between the bottom surface of clamp pad (564) and blade (552) as shown in FIGS. 24B and 24C. A proximal portion of clamp arm (560) comprises a thumb grip (578) to facilitate pivotable movement of clamp arm (560). In some versions, with clamp arm (560) coupled with instrument (520), instrument (520) is constructed and operable in accordance with at least some of the teachings of U.S. patent application Ser. No. 14/031,665, entitled "Alignment Features for Ultrasonic Surgical Instrument," filed Sep. 19, 2013, published as U.S. Pub. No. 2015/0080925 on Mar. 19, 2015, the disclosure of which is incorporated by reference herein; and/or U.S. Pub. No. 2007/0191713, entitled "Ultrasonic Device for Cutting and Coagulating," published Aug. 16, 2007, the disclosure of which is incorporated by reference herein. To remove clamp arm (560) from instrument (520), the operator merely removes shaft assembly (540) from coupler sleeve (562) of clamp arm (560) by overcoming the engagement of detents (546, 548) and dimples (568, 570).

Handle assembly (530) comprises a pair of buttons (536). Pair of buttons (536) is configured to operate substantially similar to pair of buttons (136) discussed above. For instance, as with pair of buttons (136) discussed above, when the operator depresses one button of the pair of buttons (536), generator (12) may respond with a certain energy level, such as a maximum power setting; and when the operator depresses another button of the pair of buttons (536), generator (12) may respond with another energy level, such as a minimum power setting. It should be appreciated that as the operator uses instrument (520) as a pair of surgical forceps, the operator may readily depress the buttons of pair of buttons (536) using his or her index finger to thereby activate blade (552). Thus, it should be appreciated that the operator may simultaneously activate blade (552) and compress tissue between the bottom surface of clamp pad (564) and blade (552). Furthermore, in those versions of instrument (520) in which clamp arm (560) is oriented 180° from the orientation shown in FIGS. 24A-24C, clamp arm (560) will be aligned adjacent to pair of buttons (536). In such versions of instrument (520), clamp arm (560) may include a protrusion configured to engage a button of pair of buttons (536) upon closure of clamp arm (560) to thereby activate blade (552). For instance, clamp arm (560) may be constructed and operable in accordance with at least some of the teachings of U.S. patent application No. 14/488,454, entitled "Ultrasonic Surgical Instrument with Retractable Integral Clamp Arm," filed on even date herewith, published as U.S. Pub. No. 2016/0074061 on Mar. 17, 2016, now U.S. Pat. No. 9,901,360, issued on Feb. 27, 2018, the disclosure of which is incorporated by reference herein. Thus, it should be understood that clamp arm (560) may be configured to simultaneously activate blade (552) and compress tissue between the bottom surface of clamp pad (564) and blade (552) upon closure of clamp arm (560).

As with blades (252, 352, 452) discussed above, blade (552) of the present example comprises a broad top surface so as to provide a broad surface for compression of tissue between blade (552) and clamp pad (564). The side surfaces of blade (552), on the other hand, are relatively thin such that the side surfaces of blade (552) may be used for cutting tissue without the assistance of clamp pad (564). It should be understood, however, that blade (552) may have any other suitable shape, including but not limited to any other ultrasonic blade shapes shown or described herein and/or shown or described in any of the references cited herein.

Figure 21:
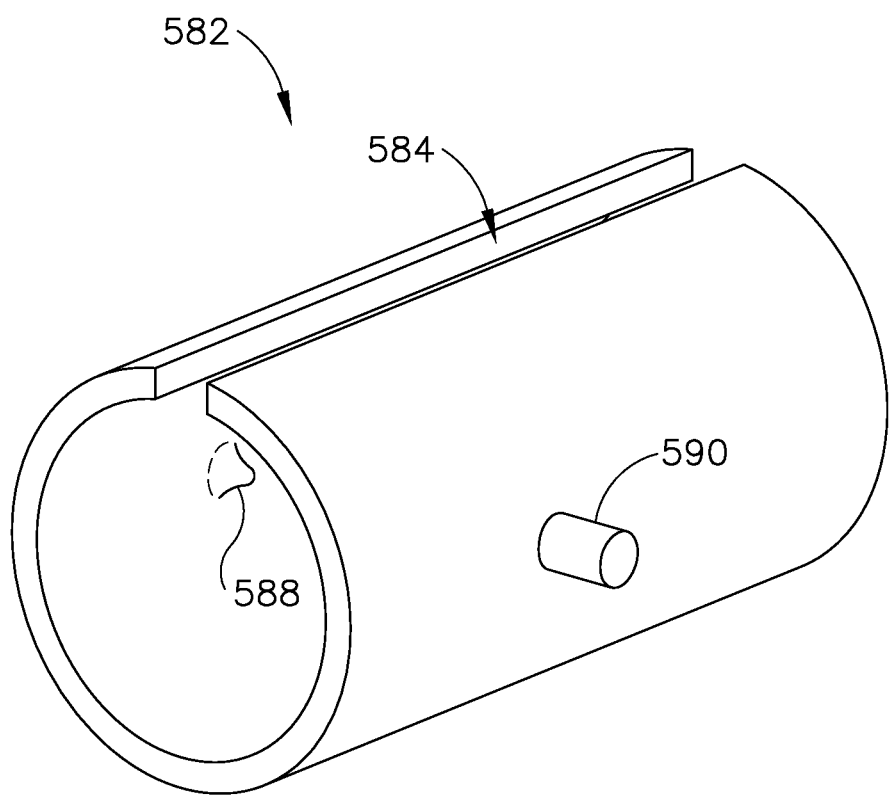
FIG. 21 depicts a perspective view of an exemplary alternative coupler sleeve of the clamp arm of FIG. 17.

FIG. 21 shows an exemplary alternative coupler sleeve (582) configured to operate substantially similar to coupler sleeve (562) except for the differences discussed below. In particular, coupler sleeve (582) is configured to receive and selectively couple with shaft assembly (540) and to provide pivotable movement of clamp arm (560) toward and away from ultrasonic blade (552) to thereby clamp and compress tissue between clamp pad (564) of clamp arm (560) and blade (552). Coupler sleeve (582) comprises an elongate slot (584) formed in a sidewall of coupler sleeve (582). Coupler sleeve (582) further comprises a pair of detent recesses (586, 588) formed in opposing sides of an interior surface of coupler sleeve (582) and a pair of pins (590, 592) extending from opposing sides of an exterior surface of coupler sleeve (582). Slot (584) is configured to receive projection (544) of outer sheath (542) such that projection (544) may be keyed into a slot (584) to thereby prevent rotation of coupler sleeve (562) (and thus clamp arm (560)) about the longitudinal axis of shaft assembly (540) when clamp arm (560) is disposed about shaft assembly (540). As with detent recesses (568, 570) of coupler sleeve (562) discussed above, detent recesses (586, 588) of coupler sleeve (582) are configured to receive detent protrusions (546, 548) of outer sheath (542) so as to selectively prevent longitudinal movement of coupler sleeve (562) (and thus clamp arm (560)) relative to shaft assembly (540).

In an exemplary use, the operator may readily transition instrument (520) between two modes of operation by selectively attaching and detaching clamp arm (560). For instance, the operator may perform at least part of a surgical procedure with clamp arm (560) detached, such that the operator uses ultrasonic blade (552) like a scalpel. The operator may thus grip and use instrument (520) in a manner similar to a grip and use of instrument (120) when clamp arm (560) is detached. Within the same surgical procedure (or in a different surgical procedure), the operator may attach clamp arm (560) to shaft assembly (540), then compress tissue between clamp pad (564) and ultrasonic blade (552) as described above. The operator may transition between these two modes as many times as desired within a given surgical procedure. Other suitable ways in which instrument (520) may be used will be apparent to those of ordinary skill in the art in view of the teachings herein.

E. Exemplary Ultrasonic Scalpel Instrument with Tabbed Coupling Feature

FIGS. 25-30C illustrate yet another exemplary ultrasonic surgical instrument (620) configured to be used as a scalpel. Instrument (620) may be used in conjunction with ultrasonic surgical system (10), which includes ultrasonic transducer (26) coupled with ultrasonic generator (12) via cable (14). Instrument (620) of this example comprises a handle assembly (630), a shaft assembly (640), and an end effector (650). Instrument (620) is configured to operate substantially similar to instrument (120) discussed above except for the differences discussed below. In particular, instrument (620) may be used to cut tissue and seal or weld tissue (e.g., a blood vessel, etc.) substantially simultaneously. Unlike instrument (120) discussed above, however, instrument (620) of the present example comprises a removable clamp arm (660). As will be discussed in more detail below, clamp arm (660) is configured to be selectively coupled to shaft assembly (640).

Figure 27:
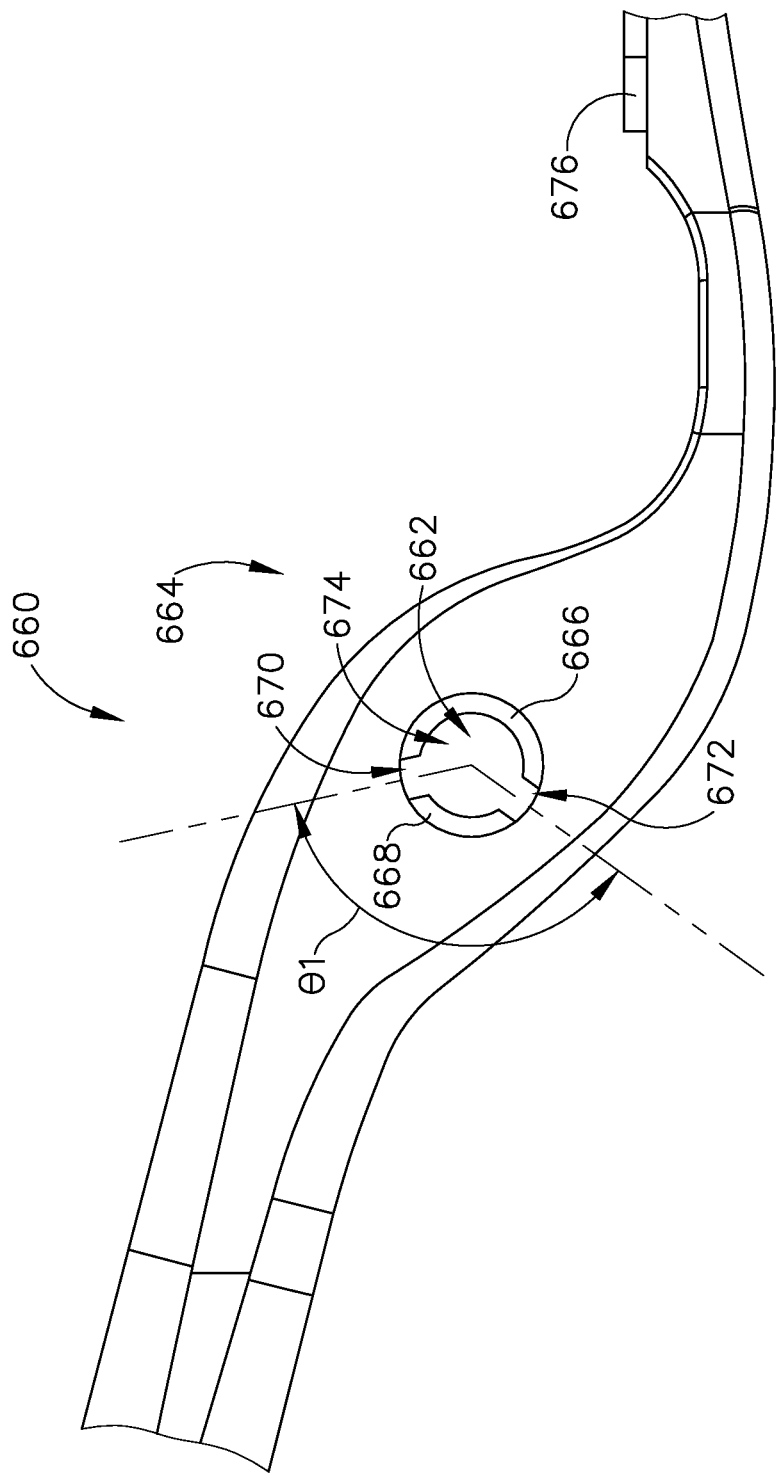
FIG. 27 depicts a detailed side elevational view of an intermediate portion of the clamp arm of FIG. 25.
Figure 28:
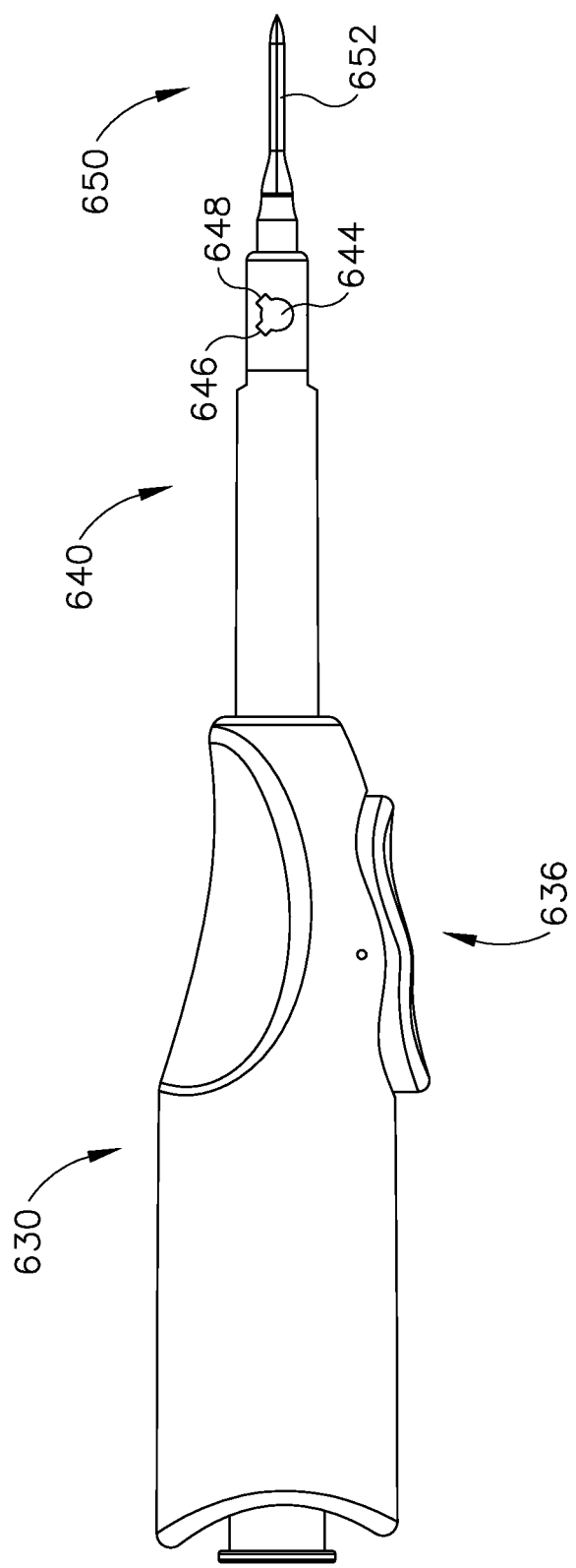
FIG. 28 depicts a side elevational view of the instrument of FIG. 25.
Figure 29:
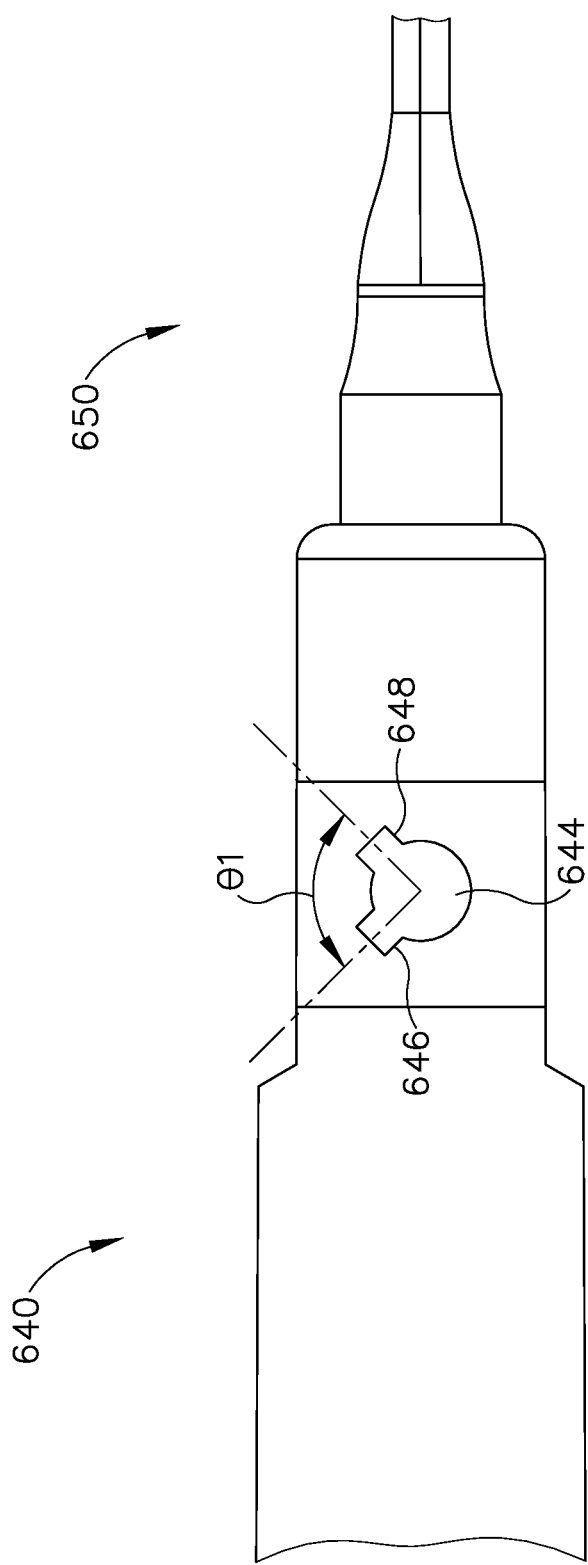
FIG. 29 depicts a detailed side elevational view of an intermediate portion of the instrument of FIG. 25.

As best seen in FIG. 27, clamp arm (660) comprises a through-bore (662) extending transversely through an intermediate portion (664) of clamp arm (660). Through-bore (662) comprises a pair of inwardly extending arcuate projections (666, 668). Arcuate projections (666, 668) together define a circular opening (674) and a pair of slots (670, 672). Slots (670, 672) are located between the circumferentially terminal ends of arcuate projections (666, 668). Slots (670, 672) are disposed at an angle (θ1) relative to one another. As best seen in FIGS. 28-29, an outer sheath (642) of shaft assembly (640) comprises a cylindrical projection (644) extending transversely from an exterior surface of outer sheath (642). Cylindrical projection (644) comprises a pair of outwardly extending tabs (646, 648). Tabs (646, 648) are disposed at the same angle (θ1) relative to one another. Cylindrical projection (644) and tabs (646, 648) are sized slightly smaller than circular opening (674) and slots (670, 672), respectively, such that cylindrical projection (644) and tabs (646, 648) may be passed through circular opening (674) and slots (670, 672). However, as shown in FIG. 30A, and as will be discussed in more detail below, through-bore (662) and cylindrical projection (644) are angularly oriented such that tabs (646, 648) and slots (670, 672) align only when clamp arm (660) is oriented into a rotational position beyond an angular range (θ2) of normal operation.

Figure 30A:
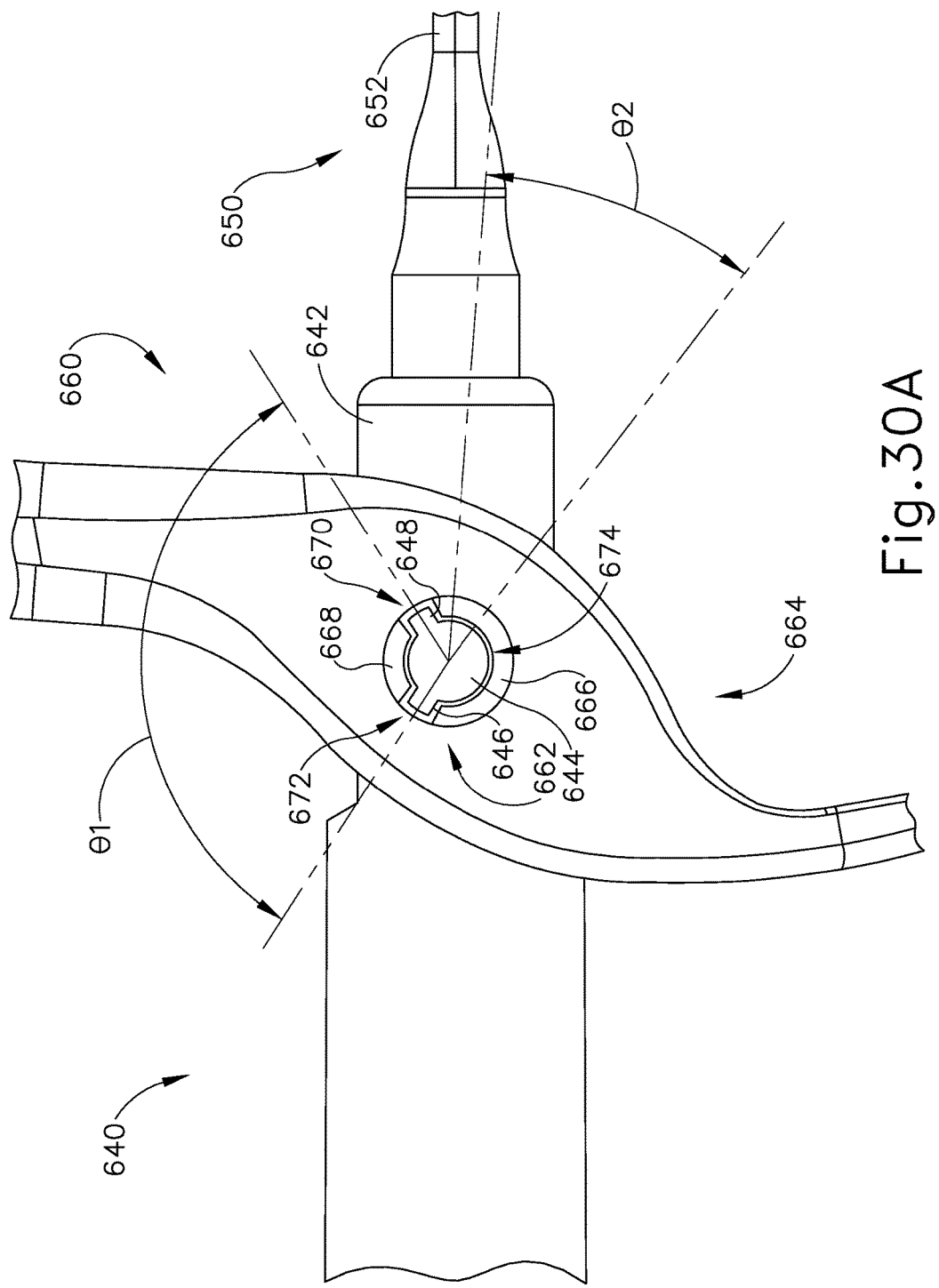
FIG. 30A depicts a detailed side elevational view of the intermediate portions of the instrument and clamp arm of FIG. 25, with the clamp arm in a first rotational position.
Figure 30B:
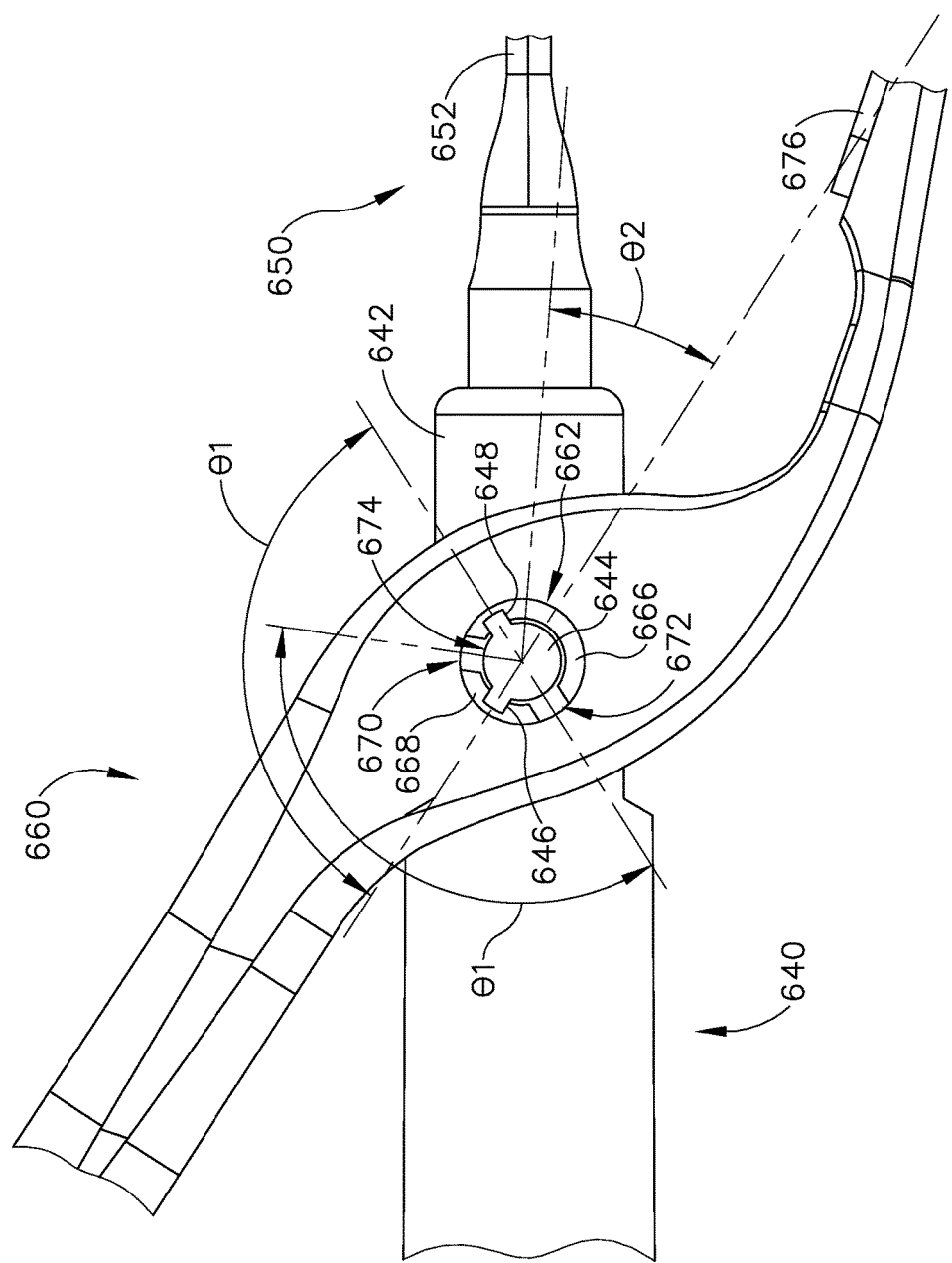
FIG. 30B depicts a detailed side elevational view of the intermediate portions of the instrument and clamp arm of FIG. 25, with the clamp arm rotated into an open position.
Figure 30C:
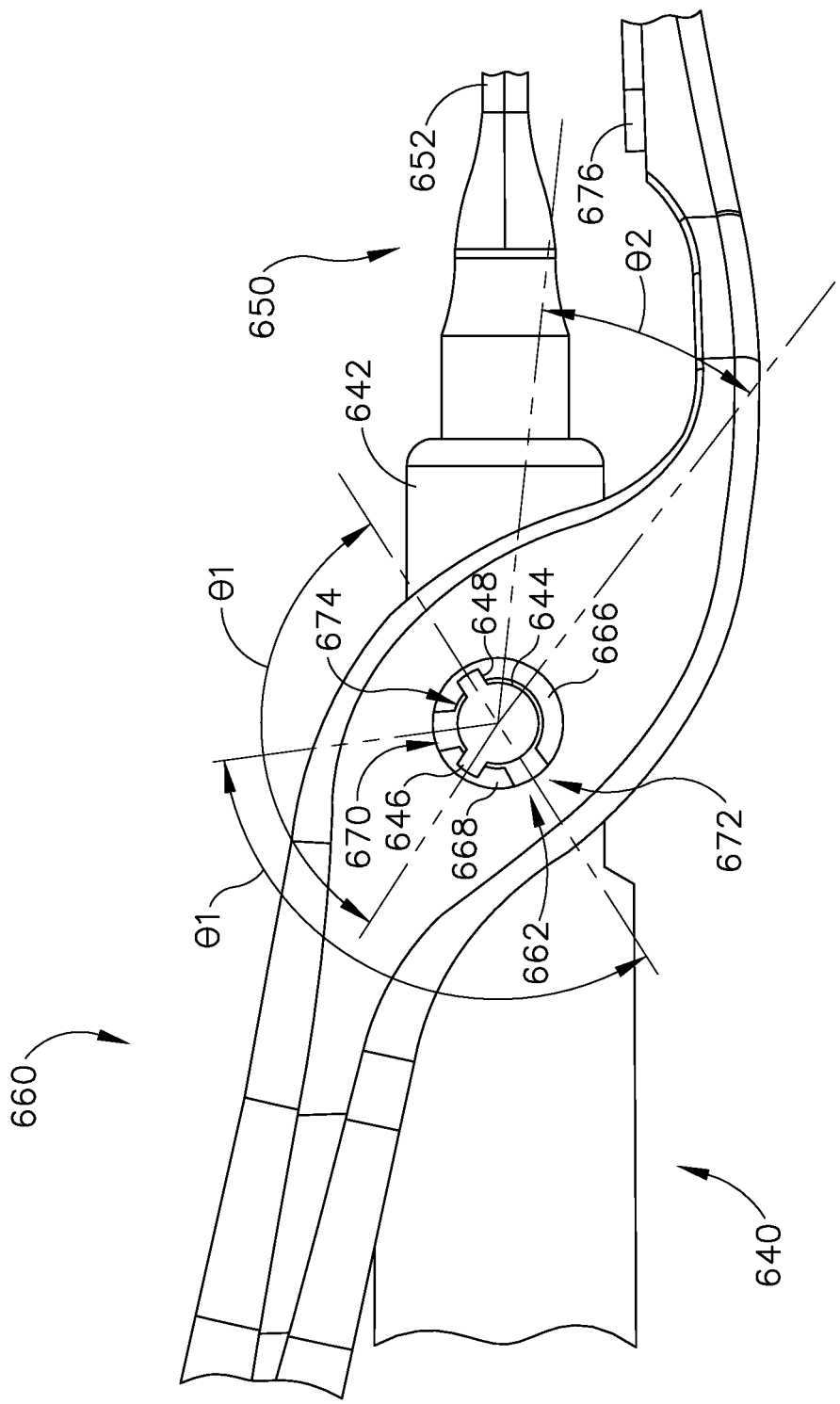
FIG. 30C depicts a detailed side elevational view of the intermediate portions of the instrument and clamp arm of FIG. 25, with the clamp arm rotated into a closed position.

To couple clamp arm (660) with instrument (620), an operator orients clamp arm (660) into the rotational position shown in FIG. 30A so as to align cylindrical projection (644) and tabs (646, 648) with circular opening (674) and slots (670, 672) respectively. At this point, the operator inserts cylindrical projection (644) and tabs (646, 648) into circular opening (674) and slots (670, 672) by urging clamp arm (660) along a path that is transverse to the longitudinal axis of shaft assembly (640); then rotates clamp arm (660) into the rotational position shown in FIG. 30B. The rotational position of clamp arm (660) shown in FIG. 30B represents an operational extent of angular range (θ2), with clamp arm (660) in an open position. The operator may then use instrument (620), including clamp arm (660), as he or she would a pair of surgical forceps to capture and compress tissue between a top surface of a clamp pad (676) and an ultrasonic blade (652) of end effector (650) by pivoting clamp arm (660) into the rotational position shown in FIG. 30C. A proximal portion of clamp arm (660) comprises a thumb grip (678) to facilitate pivotable movement of clamp arm (660). In some versions, with clamp arm (660) coupled with instrument (620), instrument (620) is constructed and operable in accordance with at least some of the teachings of U.S. patent application Ser. No. 14/031,665, entitled "Alignment Features for Ultrasonic Surgical Instrument," filed Sep. 19, 2013, published as U.S. Pub. No. 2015/0080925 on Mar. 19, 2015, the disclosure of which is incorporated by reference herein; and/or U.S. Pub. No. 2007/0191713, entitled "Ultrasonic Device for Cutting and Coagulating," published Aug. 16, 2007, the disclosure of which is incorporated by reference herein. The rotational position of clamp arm (660) shown in FIG. 30C represents another operational extent of angular range (θ2), with clamp arm (660) in a closed position. It should be understood that as clamp arm (660) is pivoted within angular range (θ2), cylindrical projection (644) and tabs (646, 648) do not align with circular opening (674) and slots (670, 672), such that tabs (646, 648) cooperate with arcuate projections (666, 668) to prevent clamp arm (660) from inadvertently decoupling from shaft assembly (640) during operation.

Handle assembly (630) comprises a pair of buttons (636). Pair of buttons (636) is configured to operate substantially similar to pair of buttons (136) discussed above. For instance, as with pair of buttons (136) discussed above, when the operator depresses one button of the pair of buttons (636), generator (12) may respond with a certain energy level, maximum power setting; and when the operator depresses another button of the pair of buttons (636), generator (12) may respond with another energy level, such as a minimum power setting. It should be appreciated that as the operator uses instrument (620) as a pair of surgical forceps, the operator may readily depress the buttons of pair of buttons (636) using his or her index finger to thereby activate blade (652). Thus, it should be appreciated that the operator may simultaneously activate blade (652) and compress tissue between the bottom surface of clamp pad (676) and blade (652).

As with blades (252, 352, 452, 552) discussed above, blade (652) of the present example comprises a broad top surface so as to provide a broad surface for compression of tissue between blade (652) and clamp pad (676). The side surfaces of blade (652), on the other hand, are relatively thin such that the side surfaces of blade (652) may be used for cutting tissue without the assistance of clamp pad (676). It should be understood, however, that blade (652) may have any other suitable shape, including but not limited to any other ultrasonic blade shapes shown or described herein and/or shown or described in any of the references cited herein.

Figure 31:
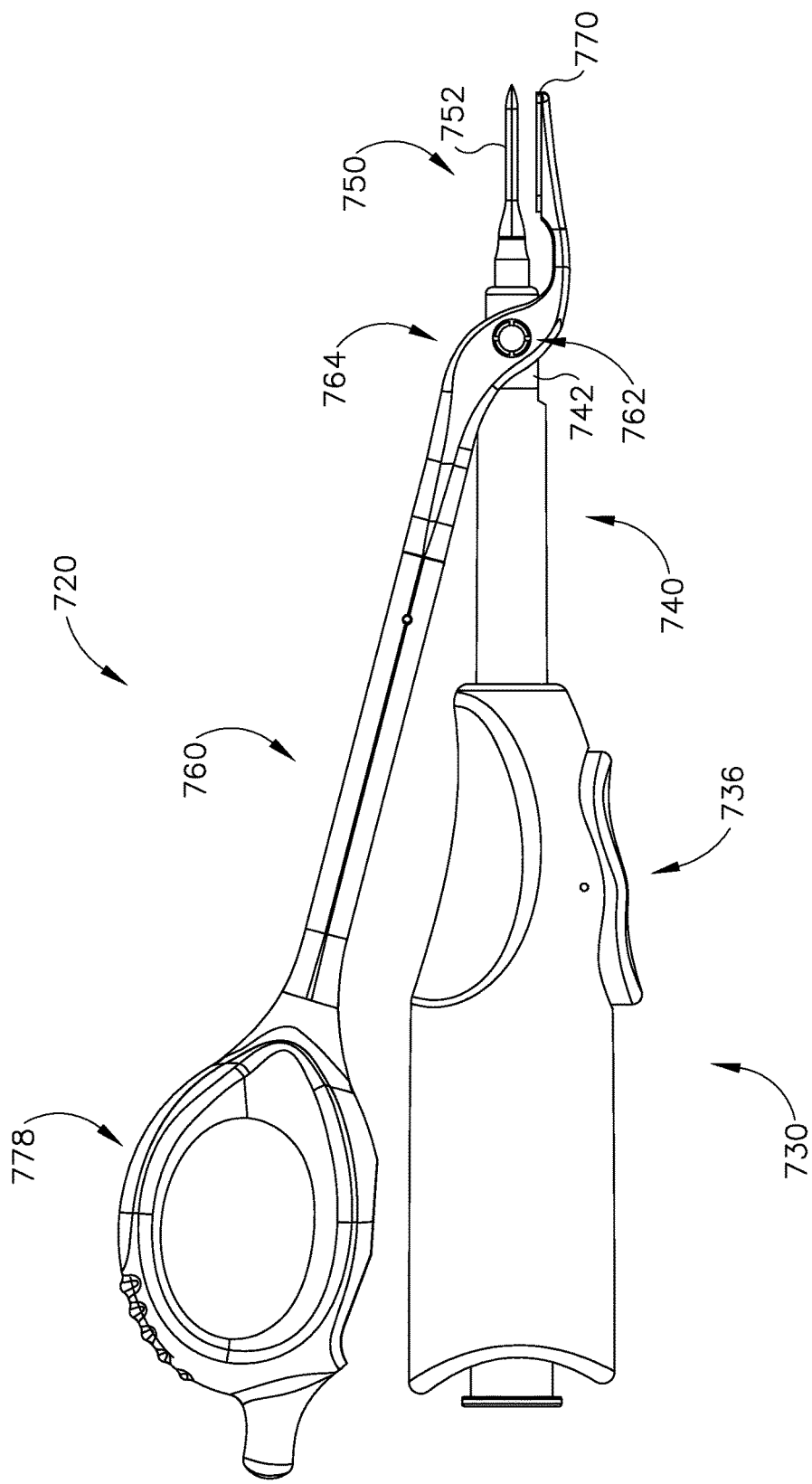
FIG. 31 depicts a side elevational view of yet another exemplary alternative surgical instrument having a removable clamp arm.
Figure 32:
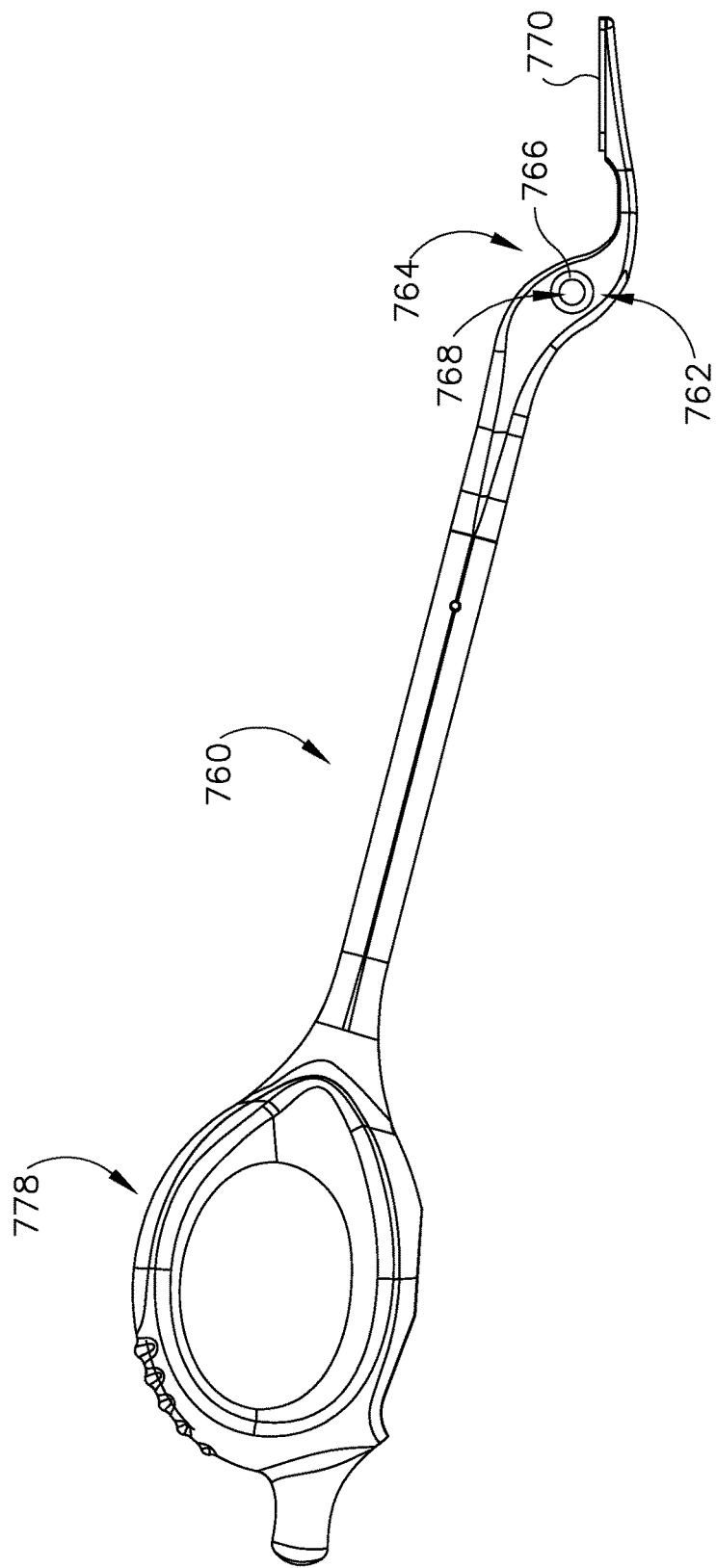
FIG. 32 depicts a side elevational view of the clamp arm of FIG. 31.

To remove clamp arm (660) from instrument (620), the operator must rotate clamp arm (660) back to the rotational position shown in FIG. 31C so as to align cylindrical projection (644) and tabs (646, 648) with circular opening (674) and slots (670, 672), respectively, such that clamp arm (560) may be removed from shaft assembly (640) by urging clamp arm (660) along a path that is transverse to the longitudinal axis of shaft assembly (640).

In an exemplary use, the operator may readily transition instrument (620) between two modes of operation by selectively attaching and detaching clamp arm (660). For instance, the operator may perform at least part of a surgical procedure with clamp arm (660) detached, such that the operator uses ultrasonic blade (652) like a scalpel. The operator may thus grip and use instrument (620) in a manner similar to a grip and use of instrument (120) when clamp arm (660) is detached. Within the same surgical procedure (or in a different surgical procedure), the operator may attach clamp arm (660) to shaft assembly (640), then compress tissue between clamp pad (676) and ultrasonic blade (652) as described above. The operator may transition between these two modes as many times as desired within a given surgical procedure. Other suitable ways in which instrument (620) may be used will be apparent to those of ordinary skill in the art in view of the teachings herein.

F. Exemplary Ultrasonic Scalpel Instrument with Resilient Coupling Feature

FIGS. 31-36 illustrate yet another exemplary ultrasonic surgical instrument (720) configured to be used as a scalpel. Instrument (720) may be used in conjunction with ultrasonic surgical system (10), which includes ultrasonic transducer (26) coupled with ultrasonic generator (12) via cable (14). Instrument (720) of this example comprises a handle assembly (730), a shaft assembly (740), and an end effector (750). Instrument (720) is configured to operate substantially similar to instrument (120) discussed above except for the differences discussed below. In particular, instrument (720) may be used to cut tissue and seal or weld tissue (e.g., a blood vessel, etc.) substantially simultaneously. Unlike instrument (120) discussed above, however, instrument (720) of the present example comprises a removable clamp arm (760). As will be discussed in more detail below, clamp arm (760) is configured to be selectively coupled to shaft assembly (740).

Figure 33:
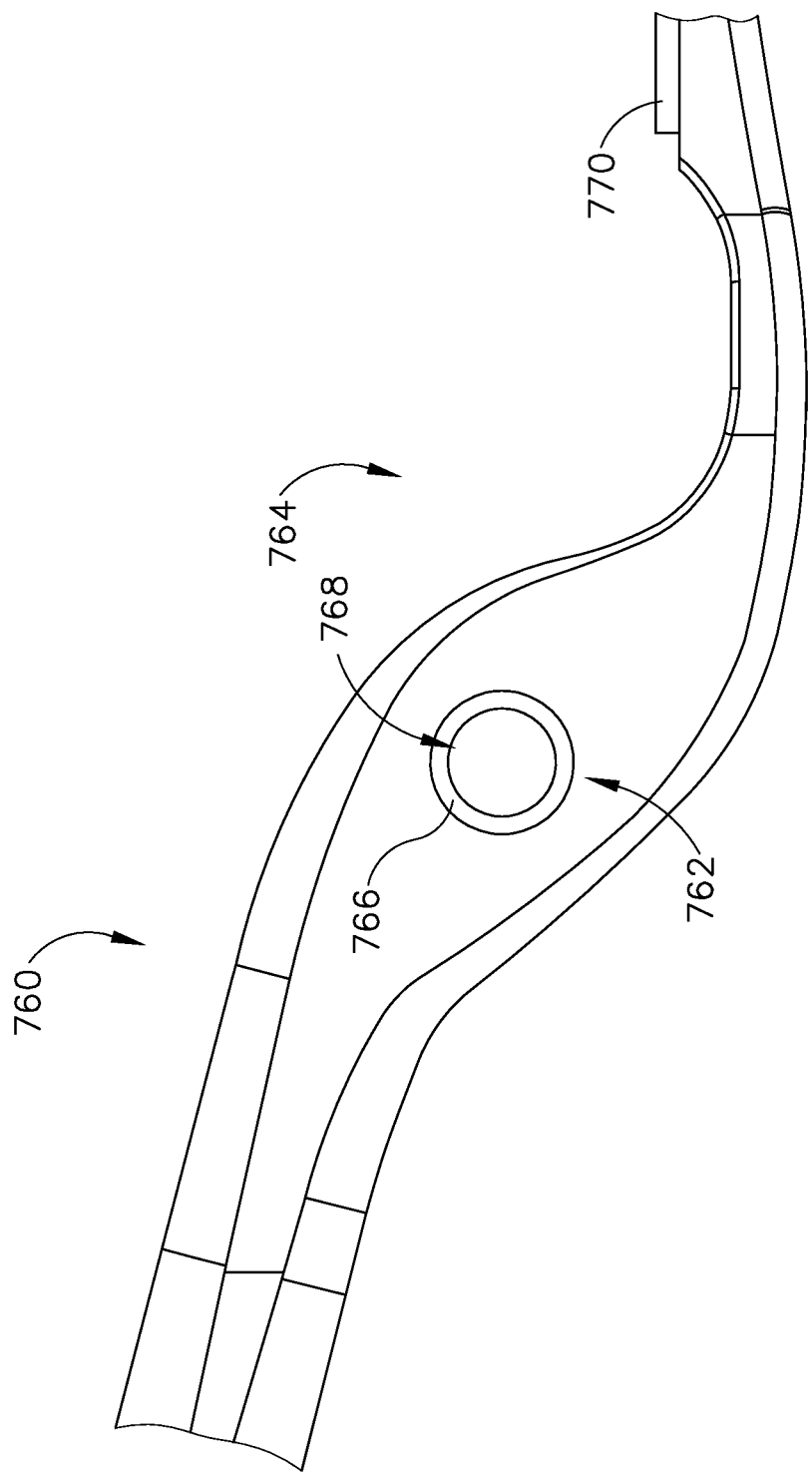
FIG. 33 depicts a detailed side elevational view of an intermediate portion of the clamp arm of FIG. 31.
Figure 34:
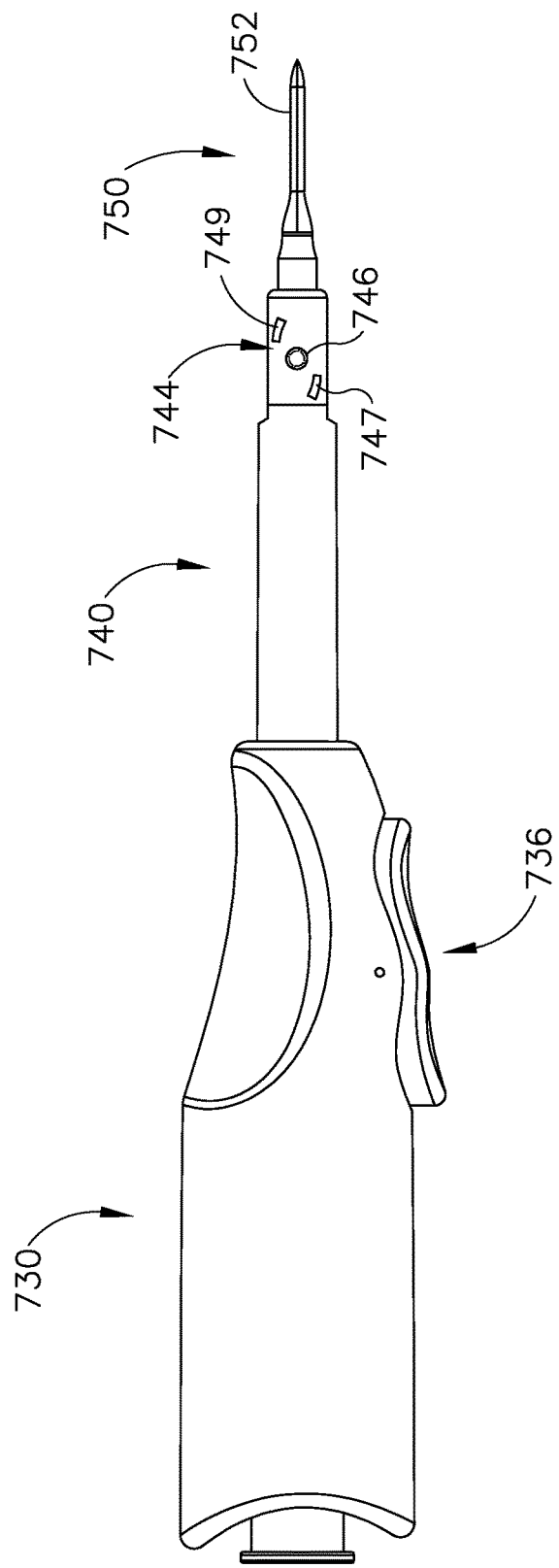
FIG. 34 depicts a side elevational view of the instrument of FIG. 31.
Figure 35:
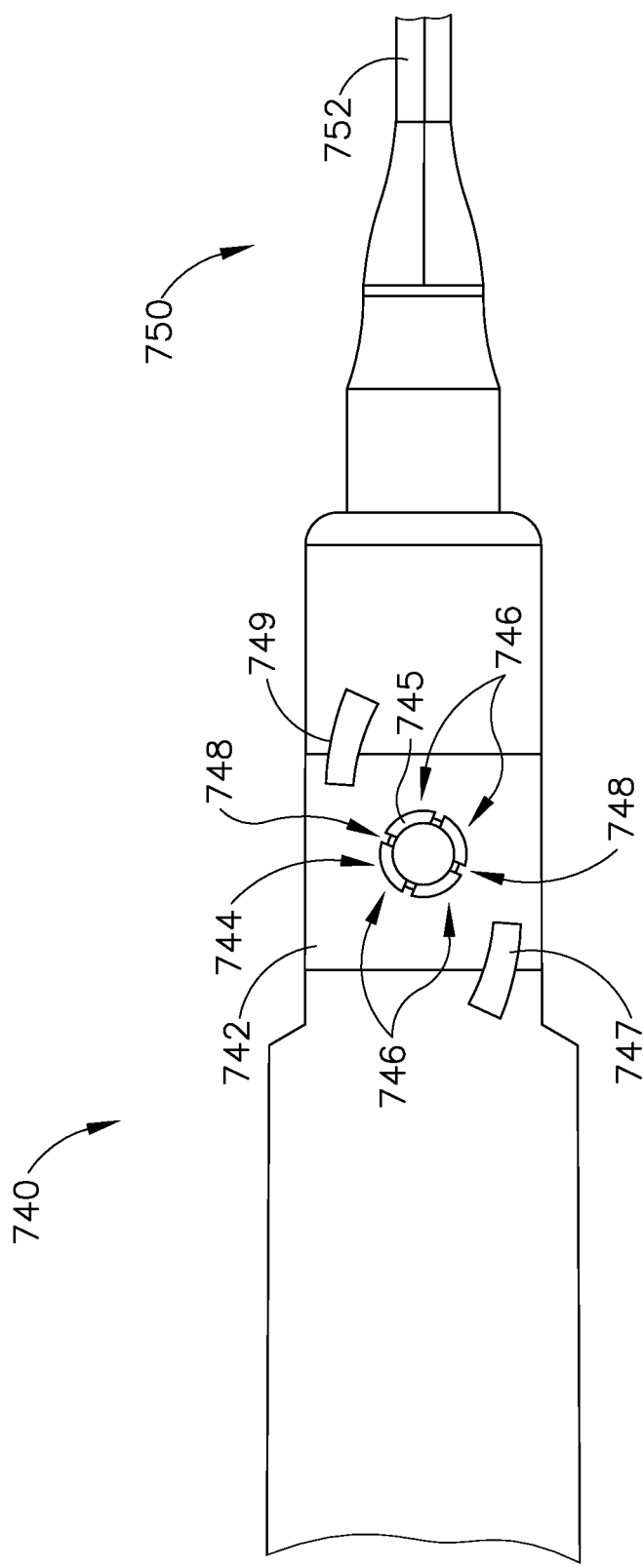
FIG. 35 depicts a detailed side elevational view of an intermediate portion of the instrument of FIG. 31.
Figure 36:
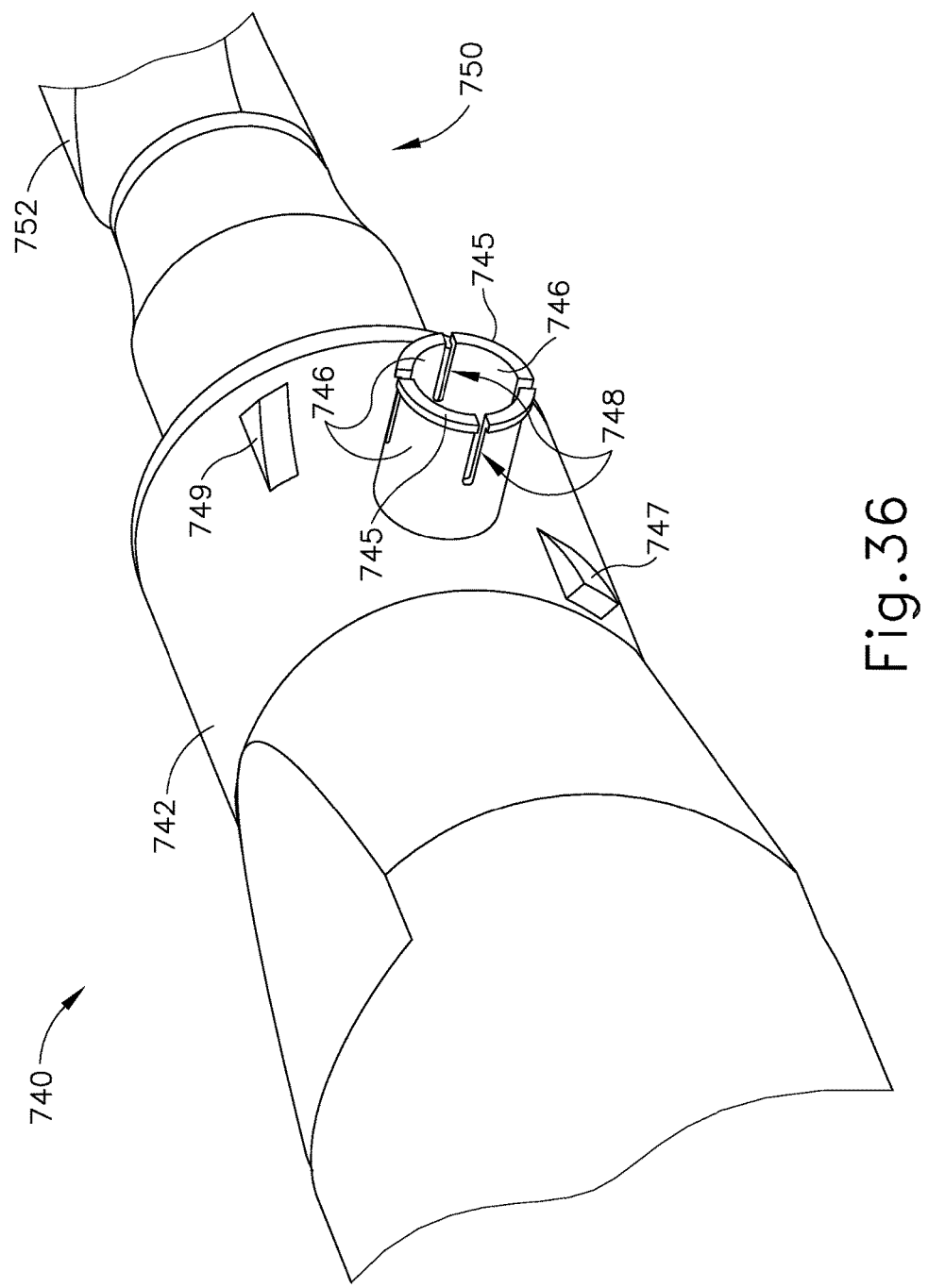
FIG. 36 depicts a detailed perspective view of an intermediate portion of the instrument of FIG. 31.
Figure 37:
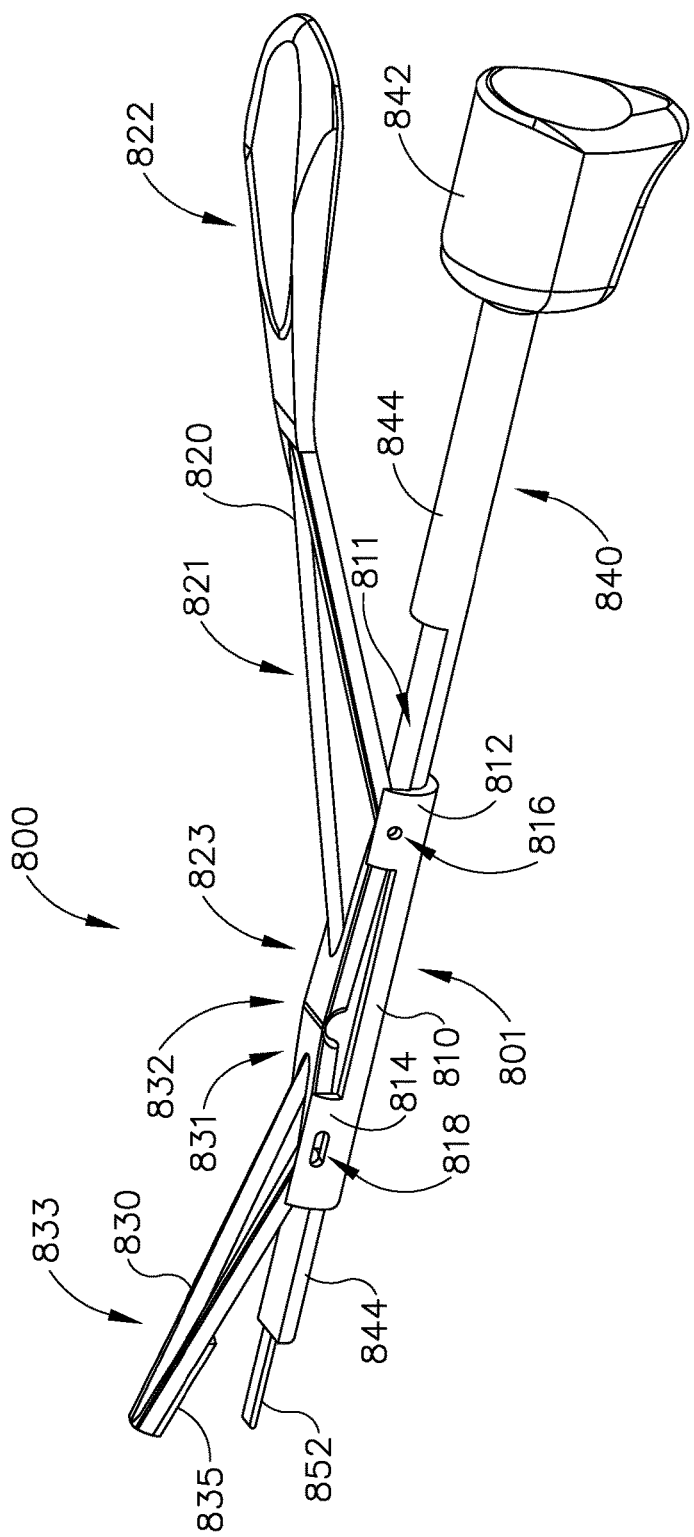
FIG. 37 depicts a perspective view of an exemplary shaft assembly and removable clamp arm.

As best seen in FIG. 33, clamp arm (760) comprises a through-bore (762) extending transversely through an intermediate portion (764) of clamp arm (760). Through-bore (762) comprises an inwardly extending circular flange (766). Circular flange (766) defines a circular opening (768). An outer sheath (742) of shaft assembly (740) comprises a hollow, cylindrical projection (744) extending transversely from an exterior surface of outer sheath (742). As best seen in FIG. 36, a tip of projection (744) comprises an outwardly extending circular lip (745). The tip of projection (744) is divided into a plurality of resilient tabs (746) by a plurality of slots (748). Tabs (746) are resiliently biased to the position shown in FIGS. 35 and 36, but as will be discussed in more detail below, tabs (746) are configured to flex to provide for coupling of clamp arm (760) and shaft assembly (740). Outer sheath (742) further comprises a pair of arcuate ramps (747, 749). As will be discussed in more detail below, ramps (747, 749) are configured to provide for decoupling of clamp arm (760) from shaft assembly (740) when clamp arm (760) is rotated clockwise beyond an open position.

To couple clamp arm (760) with instrument (720), an operator aligns projection (744) with circular opening (768) of clamp arm (760). Projection (744) is then inserted into circular opening (768) by urging clamp arm (760) along a path that is transverse to the longitudinal axis of shaft assembly (740). As projection (744) is inserted into circular opening (768), engagement between an interior surface of circular flange (766) and lip (745) of projection (744) causes tabs (746) to flex inwardly toward each other. As lip (745) passes through circular opening (768), such that lip (745) of projection (744) no longer engages the interior surface of circular projection (766), tabs (746) "snap" back into the position shown in FIGS. 35 and 36, thus coupling clamp arm (760) to shaft assembly (740). The operator may then use instrument (720), including clamp arm (760), as he or she would a pair of surgical forceps to capture and compress tissue between a top surface of a clamp pad (770) and an ultrasonic blade (752) by pivoting clamp arm (760) between an open position and a closed position. A proximal portion of clamp arm (760) comprises a thumb grip (778) to facilitate pivotable movement of clamp arm (760). In some versions, with clamp arm (760) coupled with instrument (720), instrument (720) is constructed and operable in accordance with at least some of the teachings of U.S. patent application Ser. No. 14/031,665, entitled "Alignment Features for Ultrasonic Surgical Instrument," filed Sep. 19, 2013, published as U.S. Pub. No. 2015/0080925 on Mar. 19, 2015, the disclosure of which is incorporated by reference herein; and/or U.S. Pub. No. 2007/0191713, entitled "Ultrasonic Device for Cutting and Coagulating," published Aug. 16, 2007, the disclosure of which is incorporated by reference herein.

Handle assembly (730) comprises a pair of buttons (736). Pair of buttons (736) is configured to operate substantially similar to pair of buttons (136) discussed above. For instance, as with pair of buttons (136) discussed above, when the operator depresses one button of the pair of buttons (736), generator (12) may respond with a certain energy level, maximum power setting; and when the operator depresses another button of the pair of buttons (736), generator (12) may respond with another energy level, such as a minimum power setting. It should be appreciated that as the operator uses instrument (720) as a pair of surgical forceps, the operator may readily depress the buttons of pair of buttons (736) using his or her index finger to thereby activate blade (752). Thus, it should be appreciated that the operator may simultaneously activate blade (752) and compress tissue between the bottom surface of clamp pad (770) and blade (752).

As with blades (252, 352, 452, 552, 652) discussed above, blade (752) of the present example comprises a broad top surface so as to provide a broad surface for compression of tissue between blade (752) and clamp pad (770). The side surfaces of blade (752), on the other hand, are relatively thin such that the side surfaces of blade (752) may be used for cutting tissue without the assistance of clamp pad (770). It should be understood, however, that blade (752) may have any other suitable shape, including but not limited to any other ultrasonic blade shapes shown or described herein and/or shown or described in any of the references cited herein.

To remove clamp arm (760) from instrument (720), the operator merely rotates clamp arm (760) clockwise beyond the open position such that clamp arm (760) engages ramps (747, 749). As clamp arm (760) is further rotated clockwise, ramps (747, 749) drive clamp arm (760) transversely outwardly until engagement between an interior surface of circular flange (766) and lip (745) of projection (744) causes tabs (746) to flex inwardly toward each other. At this point, clamp arm (760) may be removed from shaft assembly (740). Alternatively, the operator may manually pull clamp arm (760) transversely outwardly until engagement between an interior surface of circular flange (766) and lip (745) of projection (744) causes tabs (746) to flex inwardly toward each other. Then clamp arm (760) may be removed from shaft assembly (740).

In an exemplary use, the operator may readily transition instrument (720) between two modes of operation by selectively attaching and detaching clamp arm (760). For instance, the operator may perform at least part of a surgical procedure with clamp arm (760) detached, such that the operator uses ultrasonic blade (752) like a scalpel. The operator may thus grip and use instrument (720) in a manner similar to a grip and use of instrument (120) when clamp arm (760) is detached. Within the same surgical procedure (or in a different surgical procedure), the operator may attach clamp arm (760) to shaft assembly (740), then compress tissue between clamp pad (770) and ultrasonic blade (752) as described above. The operator may transition between these two modes as many times as desired within a given surgical procedure. Other suitable ways in which instrument (720) may be used will be apparent to those of ordinary skill in the art in view of the teachings herein.

G. Exemplary Ultrasonic Scalpel Instrument with Clamping Mechanism

FIGS. 37-54 illustrate exemplary clamping mechanisms that may be readily incorporated into any instrument (120, 220, 320, 420, 520, 620, 720) in lieu of the clamping mechanisms discussed above. FIGS. 37-43 show an exemplary surgical instrument (800) that comprises a coupling sleeve (810), a clamping mechanism (801) (which includes a rigid handle (820) and a rigid clamp arm (830)), and a shaft assembly (840). Shaft assembly (840) comprises a coupler (842) such that a handle assembly (such as any handle assembly (130, 230, 330, 430, 530, 630, 730) described above) may be coupled with shaft assembly (840), with an acoustic waveguide (positioned within with a sheath (844)) providing acoustic continuity to an ultrasonic blade (852). Alternatively, a transducer (such as transducer (26) described above) may be coupled directly with shaft assembly (840) via coupler (842), with the waveguide providing acoustic continuity to blade (852).

Figure 38:
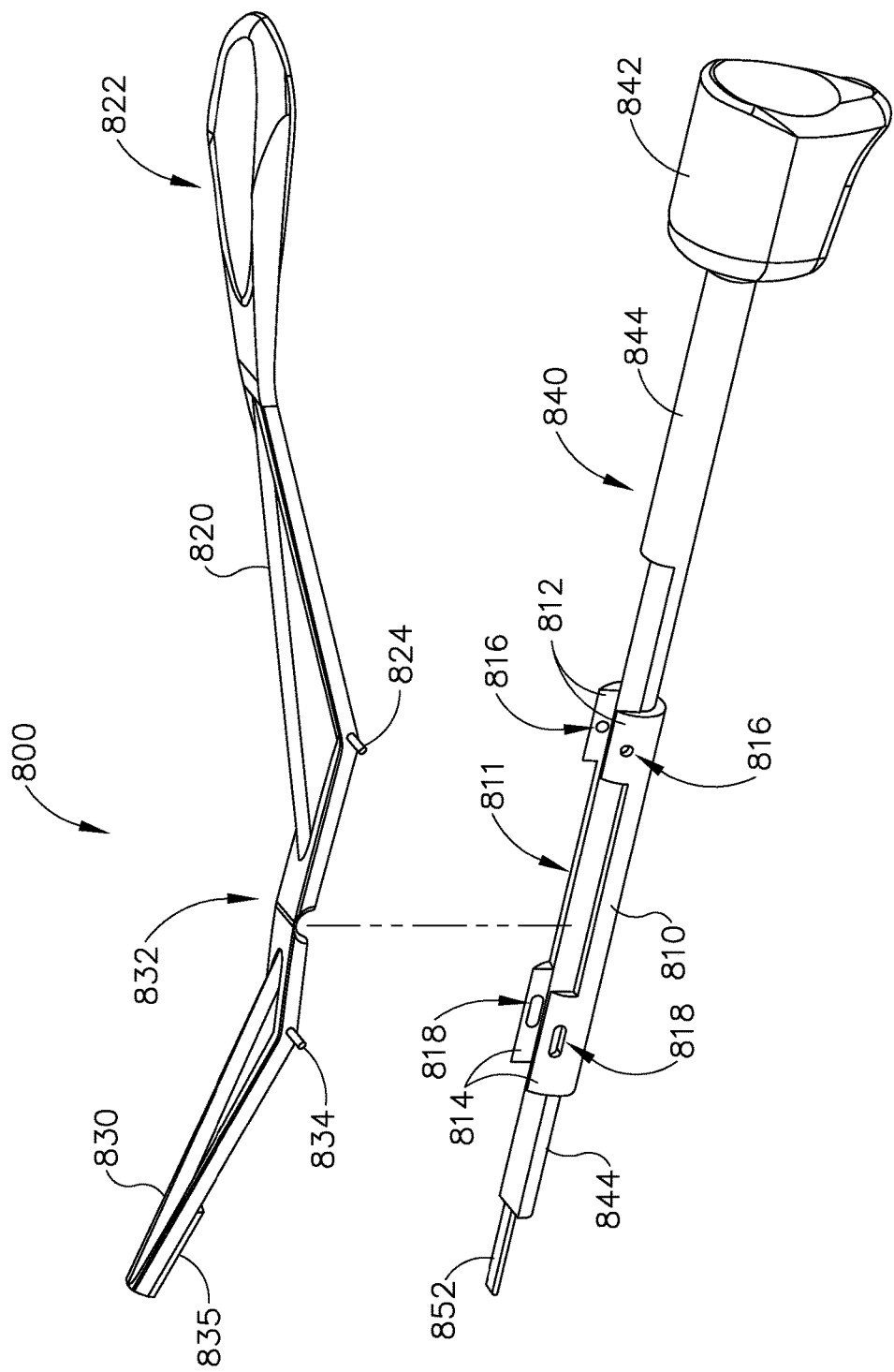
FIG. 38 depicts a partially exploded perspective view of the shaft assembly and clamp arm of FIG. 37.

Handle (820) comprises a proximal segment (821) and a distal segment (823). Proximal segment (821) and distal segment (823) together define an obtuse angle. Clamp arm (830) comprises a proximal segment (831) and a distal segment (833). Proximal segment (831) and distal segment (833) together define an obtuse angle. A distal end of distal segment (823) of handle (820) is pivotably coupled with a proximal end of proximal segment (831) of clamp arm (830) via a living hinge (832) such that handle (820) and clamp arm (830) are pivotable relative to each other. A proximal portion of handle (820) comprises a thumb grip (822) to facilitate pivotable movement of handle (820). As best seen in FIG. 38, handle (820) comprises a pair of outwardly extending pins (824) extending from opposing sides of handle (820); and clamp arm (830) comprises a pair of outwardly extending pins (834) extending from opposing sides of clamp arm (830). Pins (824) are positioned at the vertex of the obtuse angle defined by proximal segment (821) and distal segment (823) of handle (820). Pins (834) are positioned at the vertex of the obtuse angle defined by proximal segment (831) and distal segment (833) of clamp arm (830). Sleeve (810) comprises a pair of proximal tabs (812) and a pair of distal tabs (814). Proximal tabs (812) comprise through-bores (816) and distal tabs (814) comprise elongate slots (818). Pins (824) of handle (820) are disposed within through-bores (816) of proximal tabs (812) such that handle (820) is pivotably coupled to sleeve (810). Pins (834) of clamp arm (830) are disposed within elongate slots (818) of distal tabs (814) such that clamp arm (830) is pivotably and slidably coupled to sleeve (810).

Figure 39:
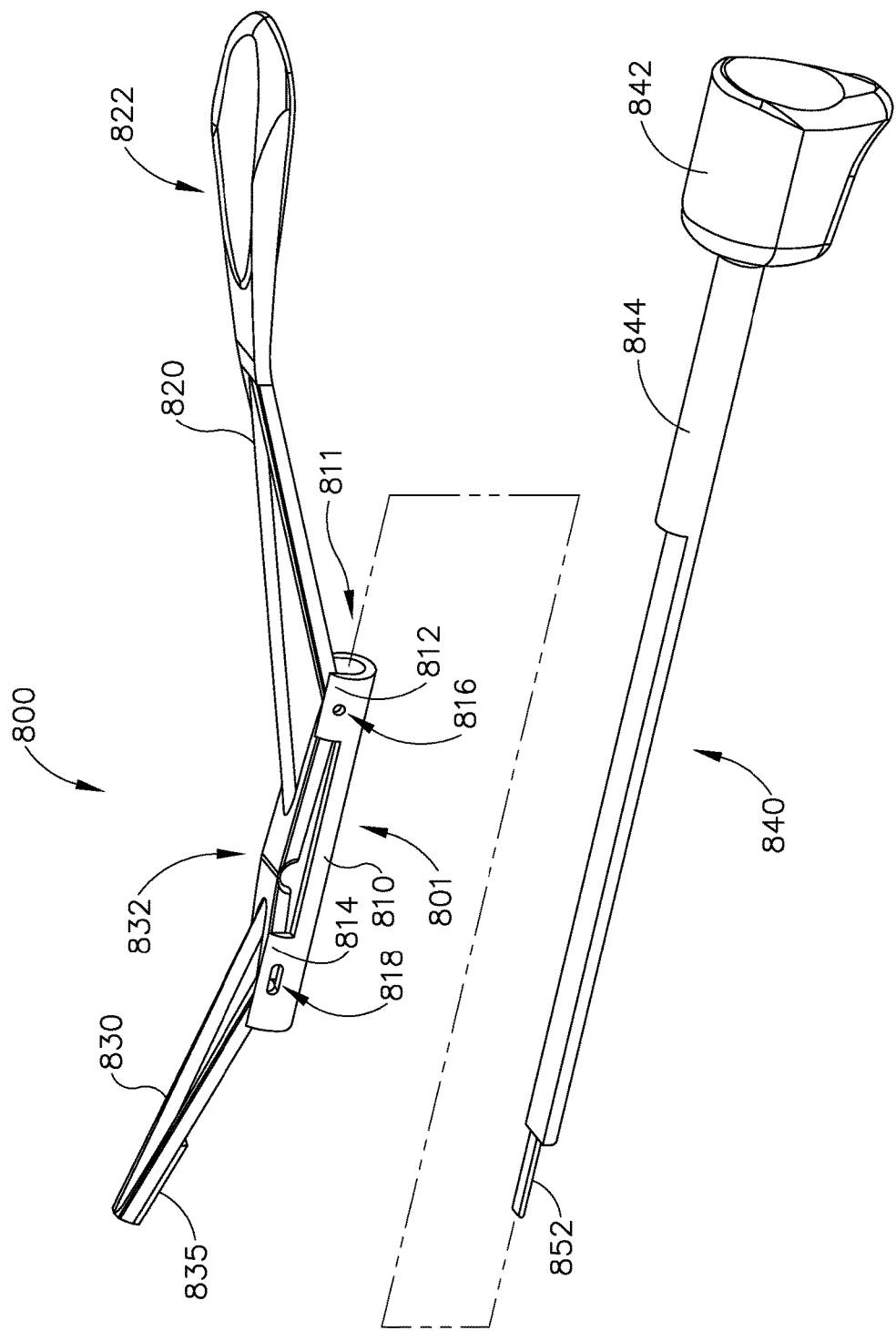
FIG. 39 depicts another partially exploded perspective view of the shaft assembly and clamp arm of FIG. 37.

As shown in FIG. 38, sleeve (810) may be an integral part of, or permanently secured to, shaft assembly (840). Handle (820) and clamp arm (830) may be selectively coupled to sleeve (810) by inserting pins (824) within through-bores (816) and pins (834) within slots (818). To allow for such insertion, pins (824, 834) and/or tabs (812, 814) may be resiliently biased and configured to flex to accommodate pins (824, 834). Alternatively, and as best seen in FIG. 39, clamping mechanism (801) may be selectively coupled with shaft assembly (840). For instance, as shown in FIG. 39, sleeve (810) comprises a channel (811) configured to receive a shaft assembly (840). Sleeve (810) is configured to receive and selectively couple clamping mechanism (801) to shaft assembly (840). The inner diameter of channel (811) may be sized slightly smaller than the outer diameter of shaft assembly (840) to create a slight interference fit, thus securing clamping mechanism (801) to shaft assembly (840). Clamping mechanism (801) may be rotated about shaft assembly (840) to any appropriate angular position about the longitudinal axis of shaft assembly (840). Alternatively, shaft assembly (840) may be keyed into sleeve (810) of clamping mechanism (801) to thereby prevent rotation of clamping mechanism (801) about the longitudinal axis of shaft assembly (840).

Figure 40A:
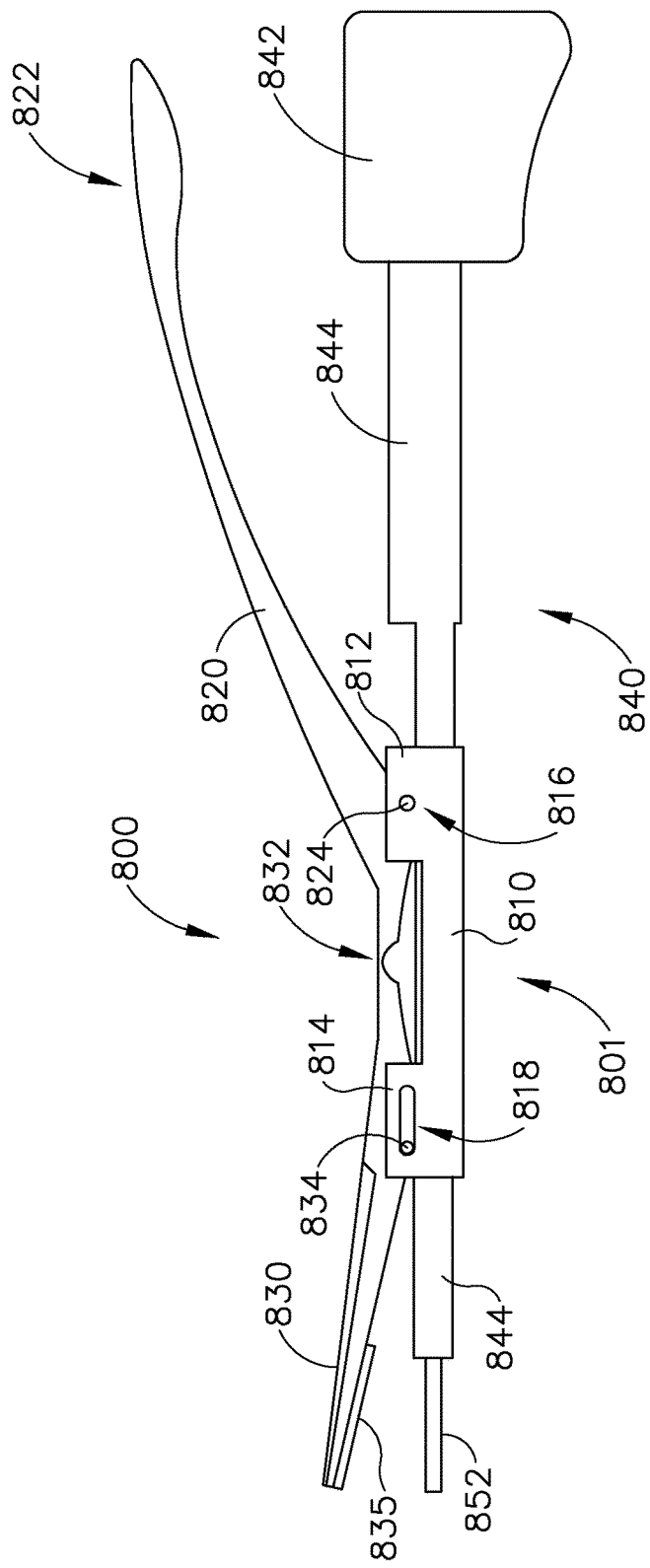
FIG. 40A depicts a side elevational view of the shaft assembly and clamp arm of FIG. 37, with the clamp arm in an open position.
Figure 40B:
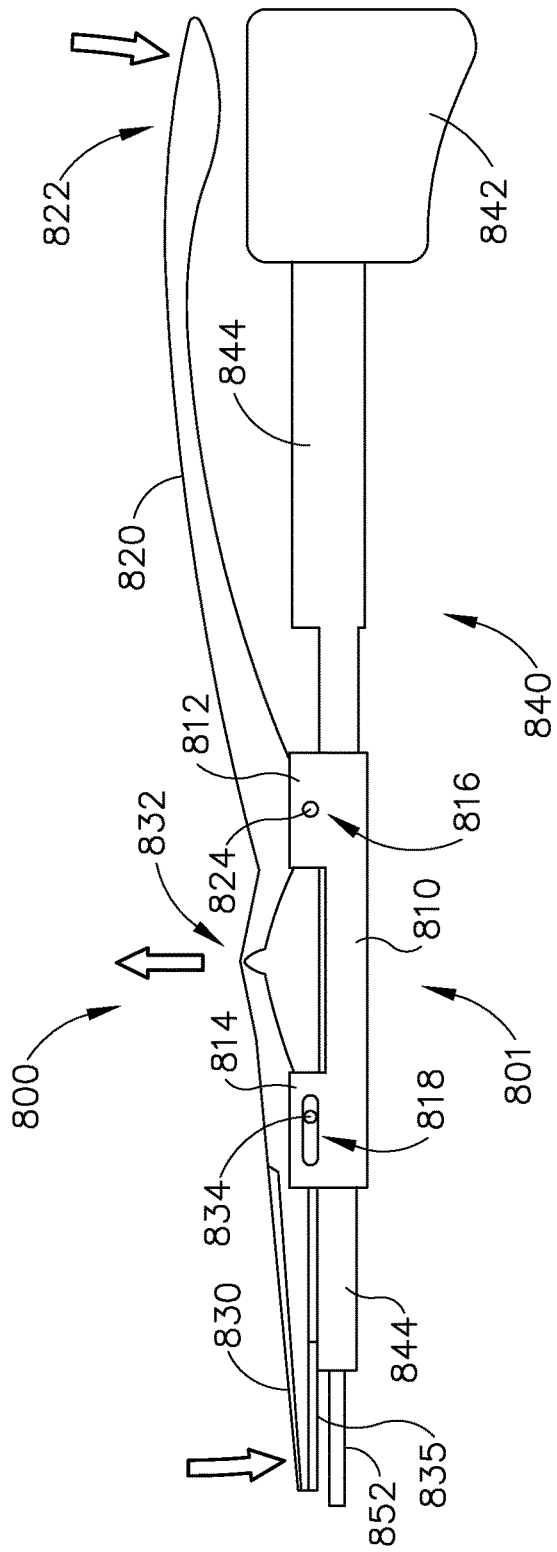
FIG. 40B depicts a side elevational view of the shaft assembly and clamp arm of FIG. 37, with the clamp arm rotated into a closed position.
Figure 41:
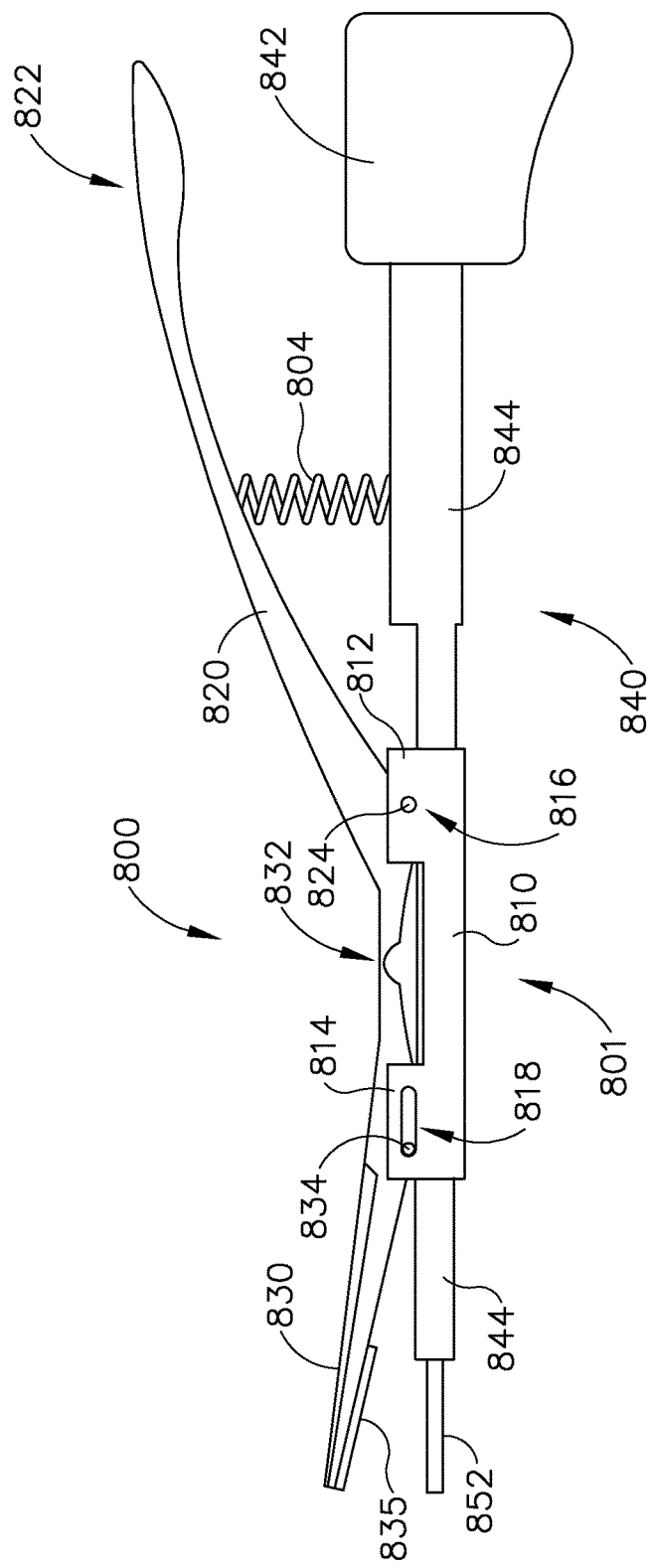
FIG. 41 depicts a side elevational view of an exemplary alternative version of the shaft assembly and clamp arm of FIG. 37.
Figure 42:
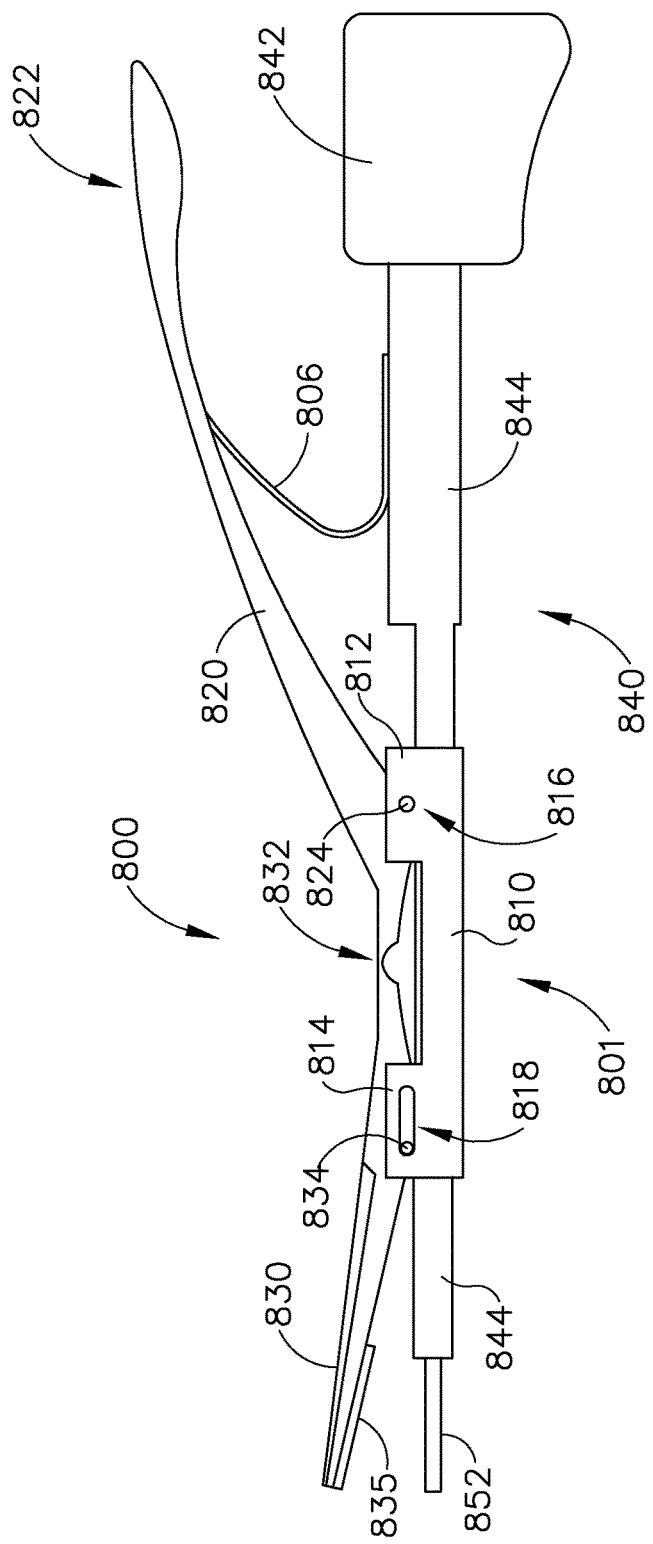
FIG. 42 depicts a side elevational view of another exemplary alternative version of the shaft assembly and clamp arm of FIG. 37.
Figure 43:
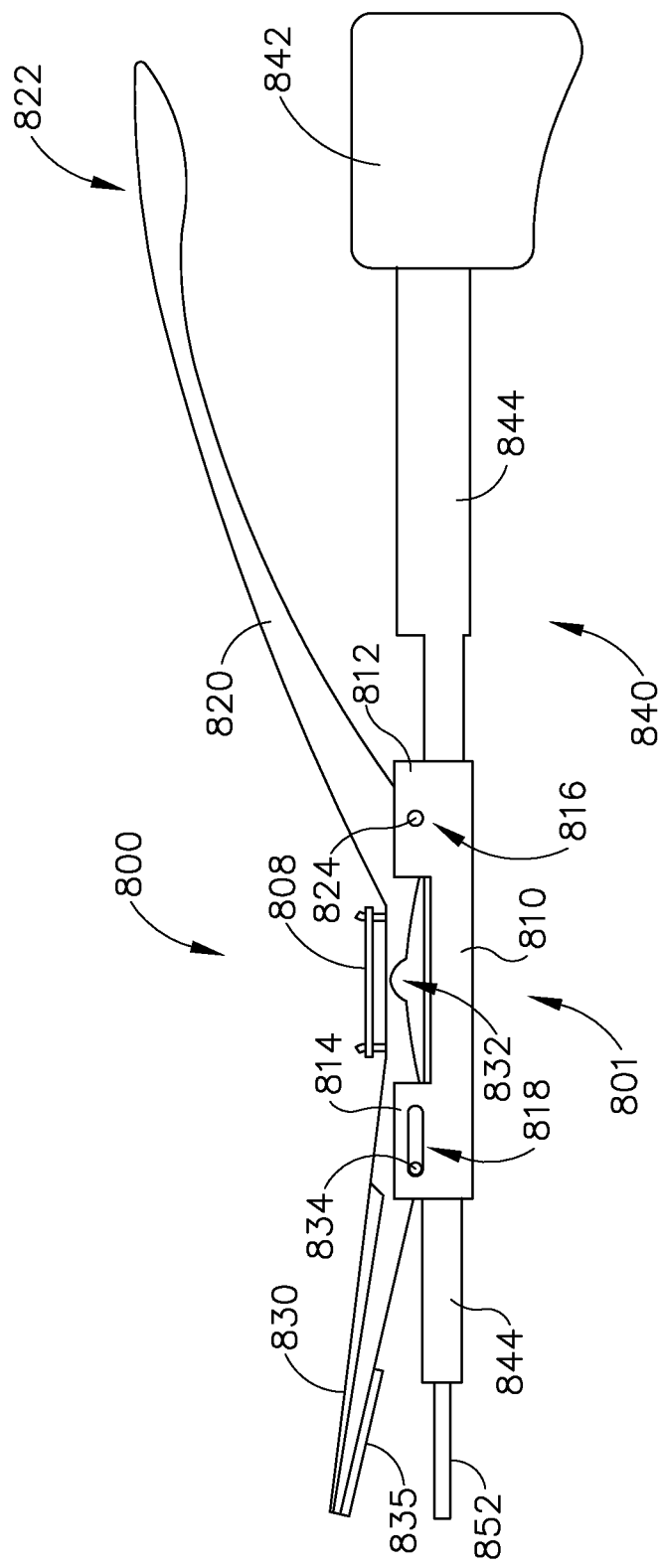
FIG. 43 depicts a side elevational view of yet another exemplary alternative version of the shaft assembly and clamp arm of FIG. 37.

With clamping mechanism (801) coupled to shaft assembly (840), the operator may use surgical instrument (800) as he or she would a pair of surgical forceps to capture and compress tissue between a clamp pad (835) of a clamp arm (830) and an ultrasonic blade (802) by pivoting clamping mechanism (801) between an open position and a closed position. FIGS. 40A and 40B show operation of clamping mechanism (801). With clamping mechanism (801) in the open position as shown in FIG. 40A, an operator forces proximal segment (821) of handle (820) downwardly toward shaft assembly (840) via thumb grip (822) so as to cause handle (820) to rotate about pins (824) disposed within slots (816), to thereby cause distal segment (823) of handle (820) to rotate upwardly away from shaft assembly (840). Rotation of distal segment (823) of handle (820) upwardly is communicated to proximal segment (831) of clamp arm (830) via living hinge (832) so as to cause proximal segment (831) of clamp arm (830) to rotate upwardly about pins (834) to thereby cause distal segment (833) of clamp arm (830) to rotate downwardly toward blade (802) into the closed position as shown in FIG. 40B. To accommodate any change in length between pins (824) and pins (834) due to rotation of handle (820) and clamp arm (830) about living hinge (832), clamp arm (830) is configured to translate longitudinally within slots (818) via pins (834). It should be understood from the foregoing that clamping mechanism (801) provides double-action leverage, with pin (824) serving as one fulcrum and pin (834) serving as another fulcrum.

Blade (852) of the present example comprises a rectangular shape having a broad top surface so as to provide a broad surface for compression of tissue between blade (852) and clamp pad (835). The side surfaces of blade (852), on the other hand, are relatively thin such that the side surfaces of blade (852) may be used for cutting tissue without the assistance of clamp pad (835). It should be understood, however, that blade (852) may have any other suitable shape, including but not limited to any other ultrasonic blade shapes shown or described herein and/or shown or described in any of the references cited herein.

By way of example only, clamping mechanism (801) may be biased toward the open position via a coil spring (804) (FIG. 41) or a leaf spring (806) (FIG. 42) disposed between proximal segment (821) of handle (820) and shaft assembly (840), or an elastic member (808) (FIG. 43) coupled between distal segment (823) of handle (820) and proximal segment (831) of clamp arm (830).

In an exemplary use, the operator may readily transition surgical instrument (800) between two modes of operation by selectively attaching and detaching clamping mechanism (801). For instance, the operator may perform at least part of a surgical procedure with clamping mechanism (801) detached, such that the operator uses ultrasonic blade (852) like a scalpel. The operator may thus grip and use instrument (800) in a manner similar to a grip and use of instrument (120) when clamping mechanism (801) is detached. Within the same surgical procedure (or in a different surgical procedure), the operator may attach clamping mechanism (801) to shaft assembly (840), then compress tissue between clamp pad (835) and ultrasonic blade (852) as described above. The operator may transition between these two modes as many times as desired within a given surgical procedure. Other suitable ways in which instrument (800) may be used will be apparent to those of ordinary skill in the art in view of the teachings herein.

Figure 44:
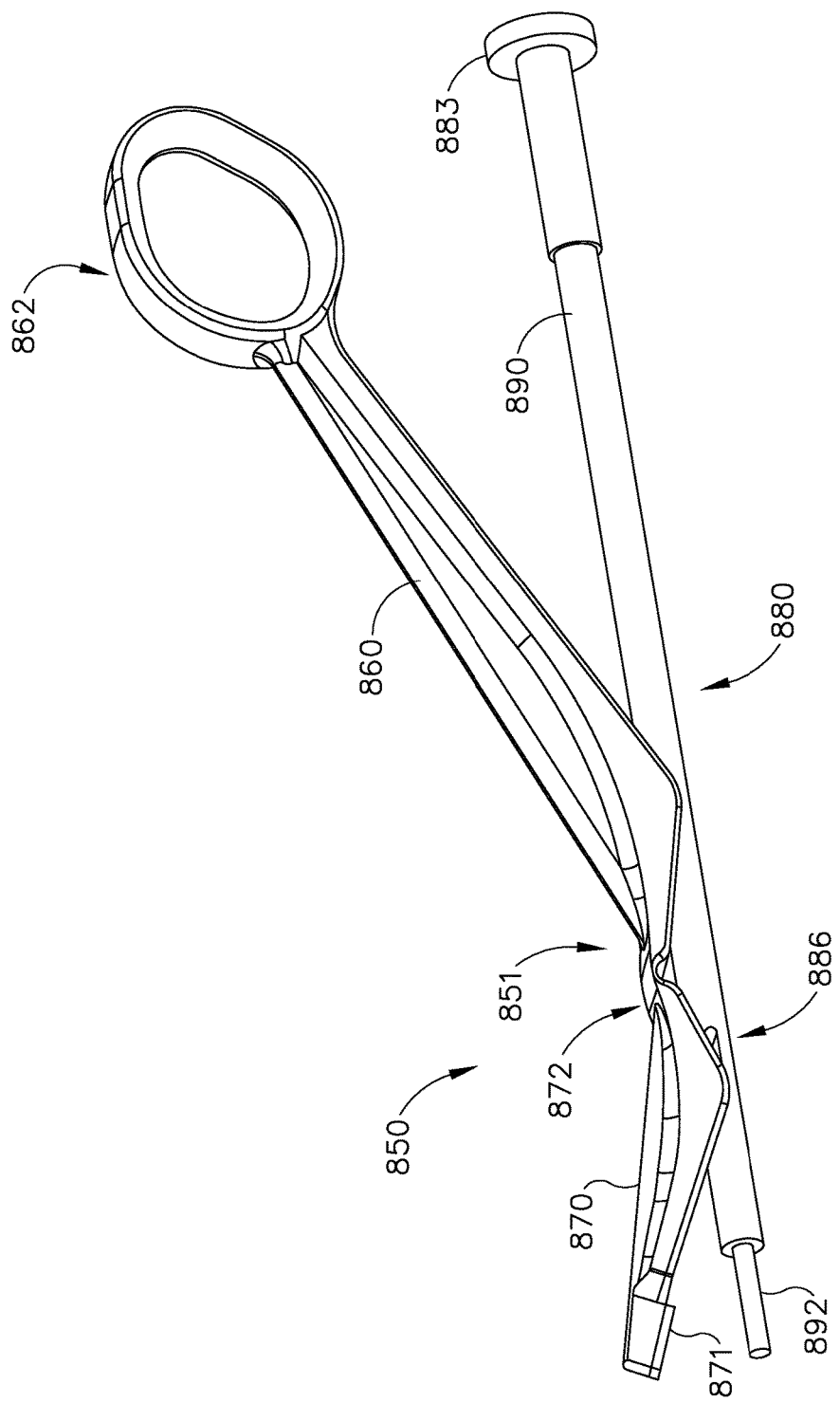
FIG. 44 depicts a perspective view of another exemplary shaft assembly and removable clamp arm.
Figure 45:
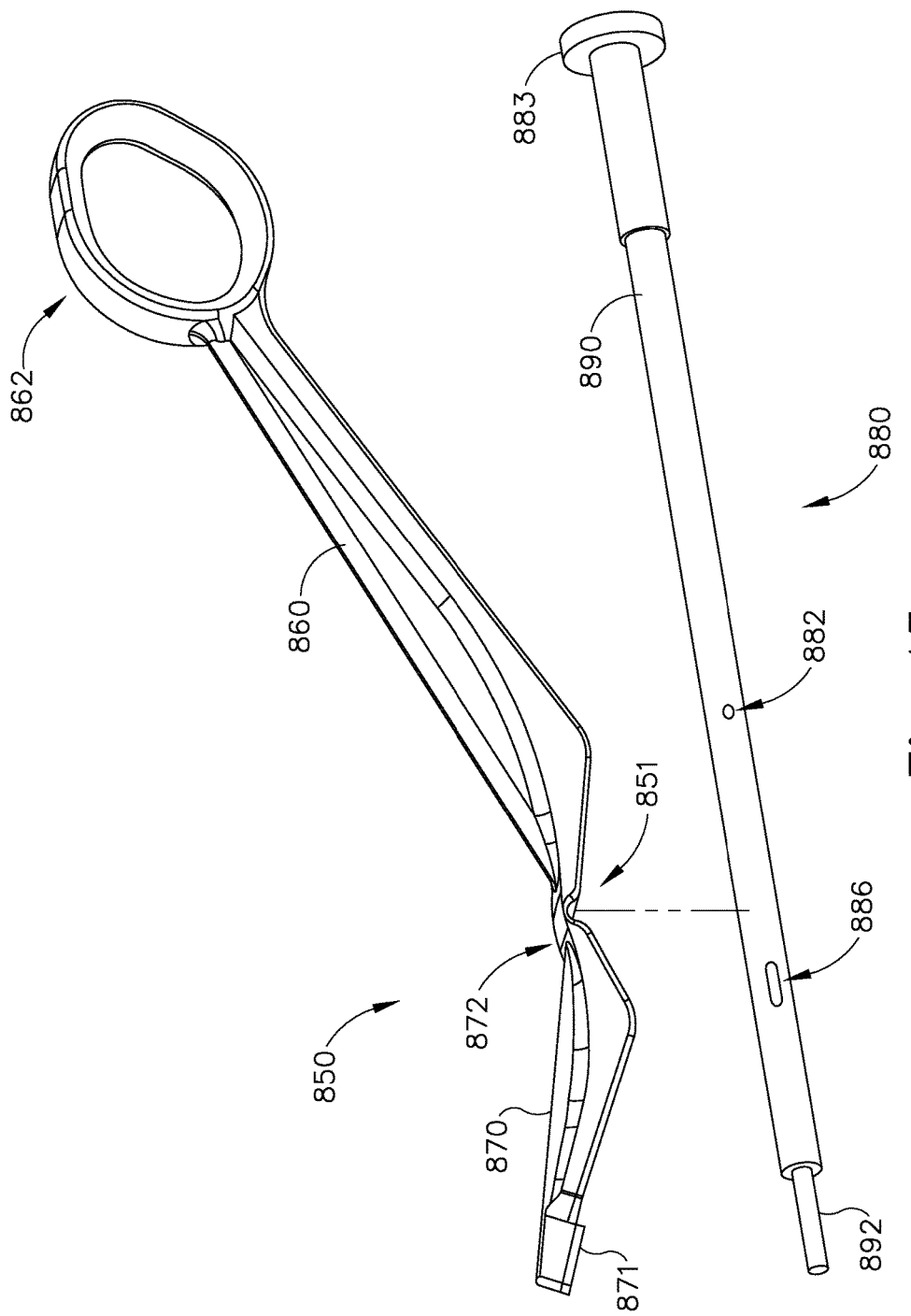
FIG. 45 depicts a partially exploded perspective view of the shaft assembly and clamp arm of FIG. 44.
Figure 46:
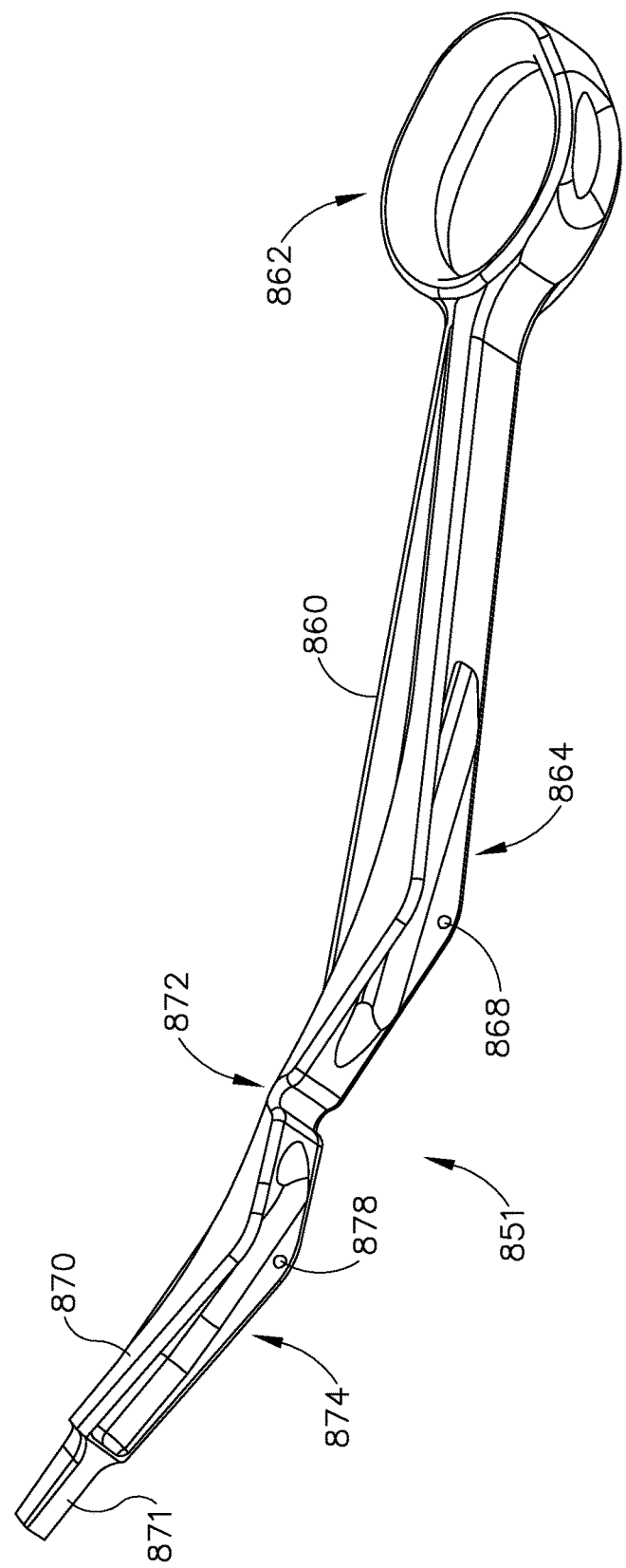
FIG. 46 depicts a perspective view of the clamp arm of FIG. 44.
Figure 47:
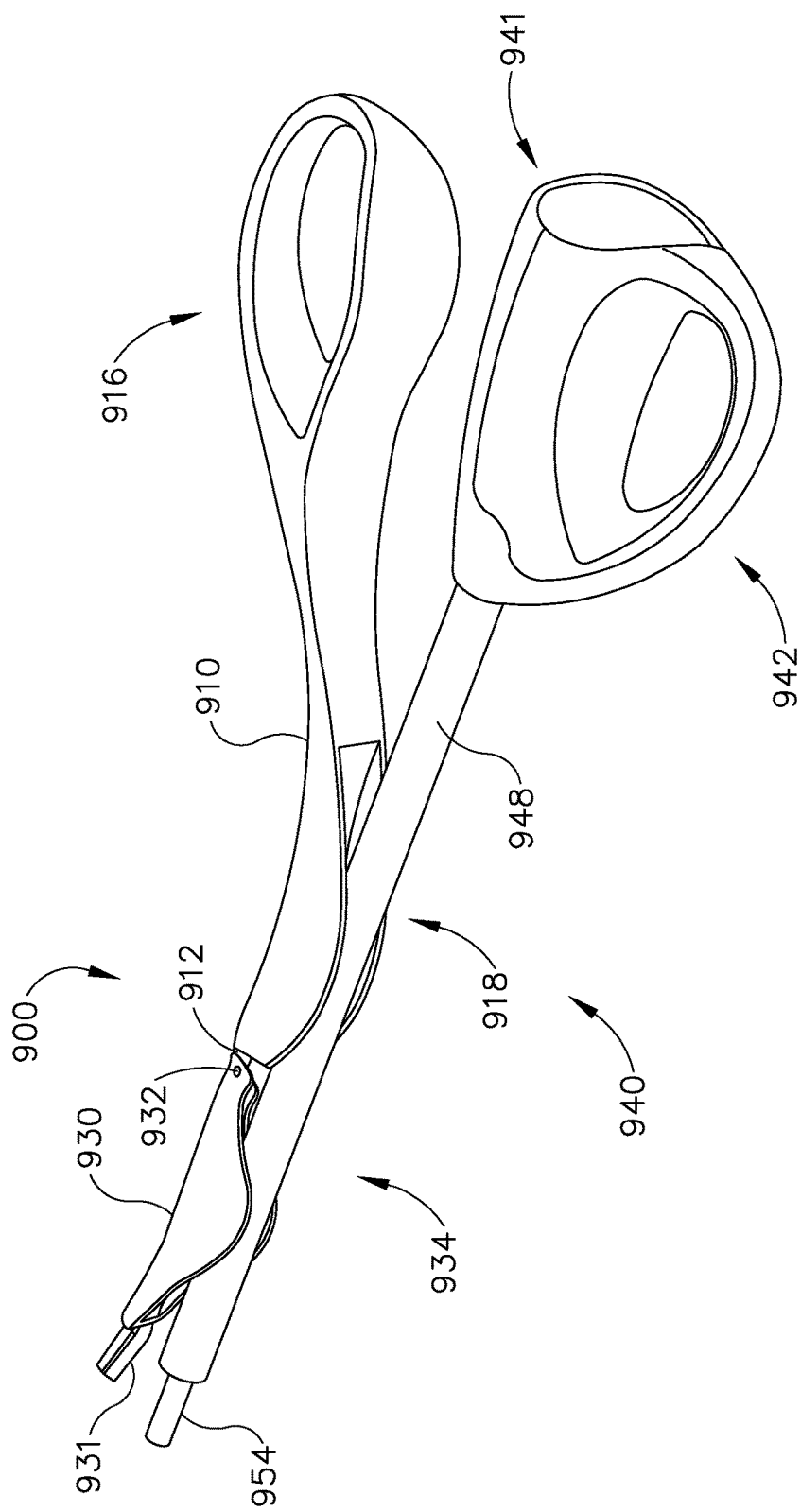
FIG. 47 depicts a perspective view of yet another exemplary shaft assembly and removable clamp arm.

FIGS. 44-46 show another exemplary surgical instrument (850). Surgical Instrument (850) comprises a clamping mechanism (851) (which includes a handle (860) and a clamp arm (870)) and a shaft assembly (880). Shaft assembly (880) comprises a coupler (883) such that a handle assembly (such as any handle assembly (130, 230, 330, 430, 530, 630, 730) described above) may be coupled with shaft assembly (880), with an acoustic waveguide (890) providing acoustic continuity to an ultrasonic blade (892). Alternatively, a transducer (such as transducer (26) described above) may be coupled directly with shaft assembly (880) via coupler (883), with waveguide (890) providing acoustic continuity to blade (892). A distal end of handle (860) is pivotably coupled with a proximal end of clamp arm (870) via a living hinge (872) such that handle (860) and clamp arm (870) are pivotable relative to each other. A proximal portion of handle (860) comprises a thumb grip (862) to facilitate pivotable movement of handle (860). As best seen in FIG. 46, handle (860) comprises a channel (864) configured to receive a shaft assembly (880); and clamp arm (870) also comprises a channel (874) configured to receive shaft assembly (880). Handle (860) comprises a pair of pins (866, 868) extending inwardly from opposing interior surfaces of channel (864); and clamp arm (870) also comprises a pair of pins (876, 878) extending inwardly from opposing surfaces of channel (874). Shaft assembly (880) comprises a pair of circular recesses (882, 884) formed in opposing sides of an exterior surface of an outer sheath (881) of shaft assembly (880); and a pair of elongate recesses (886, 888) formed in opposing sides of the exterior surface of outer sheath (881) distal of circular recesses (882, 884). Circular recesses (882, 884) are configured to rotatably receive pins (866, 868) of handle (860) and elongate recesses (886, 888) are configured to slidably and rotatably receive pins (876, 878).

With clamping mechanism (851) coupled to shaft assembly (880), the operator may use surgical instrument (850) as he or she would a pair of surgical forceps to capture and compress tissue between a clamp pad (871) of a clamp arm (870) and blade (892) by pivoting clamping mechanism (851) between an open position and a closed position. With clamping mechanism (851) in an open position, an operator may force handle (860) downwardly toward shaft assembly (880) via thumb grip (862) so as to cause handle (860) to rotate about pins (866, 868) within circular recesses (882, 884) to thereby cause the distal end of handle (860) to rotate upwardly away from shaft assembly (880). Rotation of the distal end of handle (860) upwardly is communicated to the proximal end of clamp arm (870) via living hinge (872) so as to cause the proximal end of clamp arm (870) to rotate upwardly about pins (876, 878) to thereby cause the distal end of clamp arm (870) to pivot downwardly toward blade (892) into a closed position. To accommodate any change in length between pins (866, 868) and pins (876, 878) due to rotation of handle (860) and clamp arm (870) about living hinge (872), clamp arm (870) is configured to translate longitudinally within elongate recesses (886, 888) via pins (876, 878). It should be understood from the foregoing that clamping mechanism (851) provides double-action leverage, with pin (876) serving as one fulcrum and pin (878) serving as another fulcrum.

Blade (892) of the present example has a cylindraceous shape. Blade (892) may thus provide the same performance characteristics regardless of the angular position at which tissue contacts blade (892). It should be understood, however, that blade (892) may have any other suitable shape, including but not limited to any other ultrasonic blade shapes shown or described herein and/or shown or described in any of the references cited herein.

In an exemplary use, the operator may readily transition surgical instrument (850) between two modes of operation by selectively attaching and detaching clamping mechanism (851). For instance, the operator may perform at least part of a surgical procedure with clamping mechanism (851) detached, such that the operator uses ultrasonic blade (892) like a scalpel. The operator may thus grip and use instrument (850) in a manner similar to a grip and use of instrument (120) when clamping mechanism (851) is detached. Within the same surgical procedure (or in a different surgical procedure), the operator may attach clamping mechanism (851) to shaft assembly (880), then compress tissue between clamp pad (871) and ultrasonic blade (892) as described above. The operator may transition between these two modes as many times as desired within a given surgical procedure. Other suitable ways in which instrument (850) may be used will be apparent to those of ordinary skill in the art in view of the teachings herein.

Figure 48:
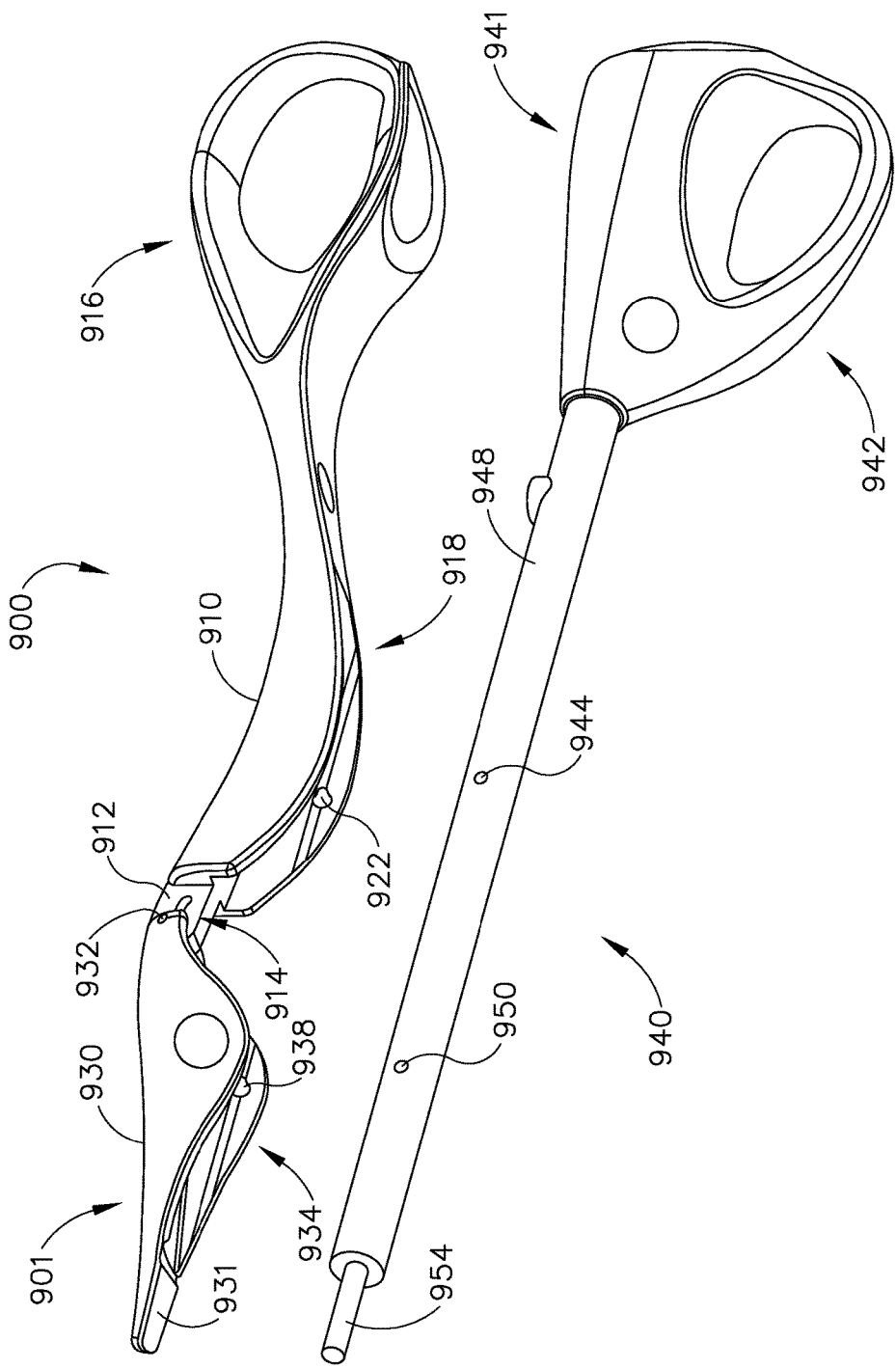
FIG. 48 depicts a partially exploded perspective view of the shaft assembly and clamp arm of FIG. 47.

FIGS. 47-54 show another exemplary surgical instrument (900). Surgical instrument (900) comprises a clamping mechanism (901) (which includes a handle (910) and a clamp arm (930)) and a shaft assembly (940). Shaft assembly (940) comprises a coupler (941) such that a handle assembly (such as any handle assembly (130, 230, 330, 430, 530, 630, 730) described above) may be coupled with shaft assembly (940), with an acoustic waveguide (positioned within with an outer sheath (948)) providing acoustic continuity to an ultrasonic blade (954). Alternatively, a transducer (such as transducer (26) described above) may be coupled directly with shaft assembly (940) via coupler (941), with the waveguide providing acoustic continuity to blade (954). A distal end of handle (910) comprises a tab (912) extending distally from the distal end of handle (910). Tab (912) comprises an elongate slot (914). The distal end of handle (910) is pivotably coupled with a proximal end of clamp arm (930) via a pin (932). Pin (932) is rotatably and slidably disposed within slot (914) of tab (912) such that handle (910) and clamp arm (930) may pivot relative to each other. A proximal portion of handle (910) comprises a thumb grip (916), and coupler (941) of shaft assembly (940) comprises a finger grip (942) to facilitate pivotable movement of handle (910). As best seen in FIG. 48, handle (910) comprises a channel (918) configured to receive shaft assembly (940); and clamp arm (930) also comprises a channel (934) configured to receive shaft assembly (940). Handle (910) comprises a pair of pins (922) extending inwardly from opposing interior surfaces of channel (918); and clamp arm (930) also comprises a pair of pins (938) extending inwardly from opposing surfaces of channel (934). Shaft assembly (940) comprises a first pair of circular recesses (944, 946) formed in opposing sides of an exterior surface of an outer sheath (948) of shaft assembly (940); and a second pair of circular recesses (950, 952) formed in opposing sides of the exterior surface of outer sheath (948) distal of circular recesses (944, 946). Circular recesses (944, 946) are configured to rotatably receive pins (922) of handle (910) and circular recesses (950, 952) are configured to rotatably receive pins (938).

Figures 49, 50:
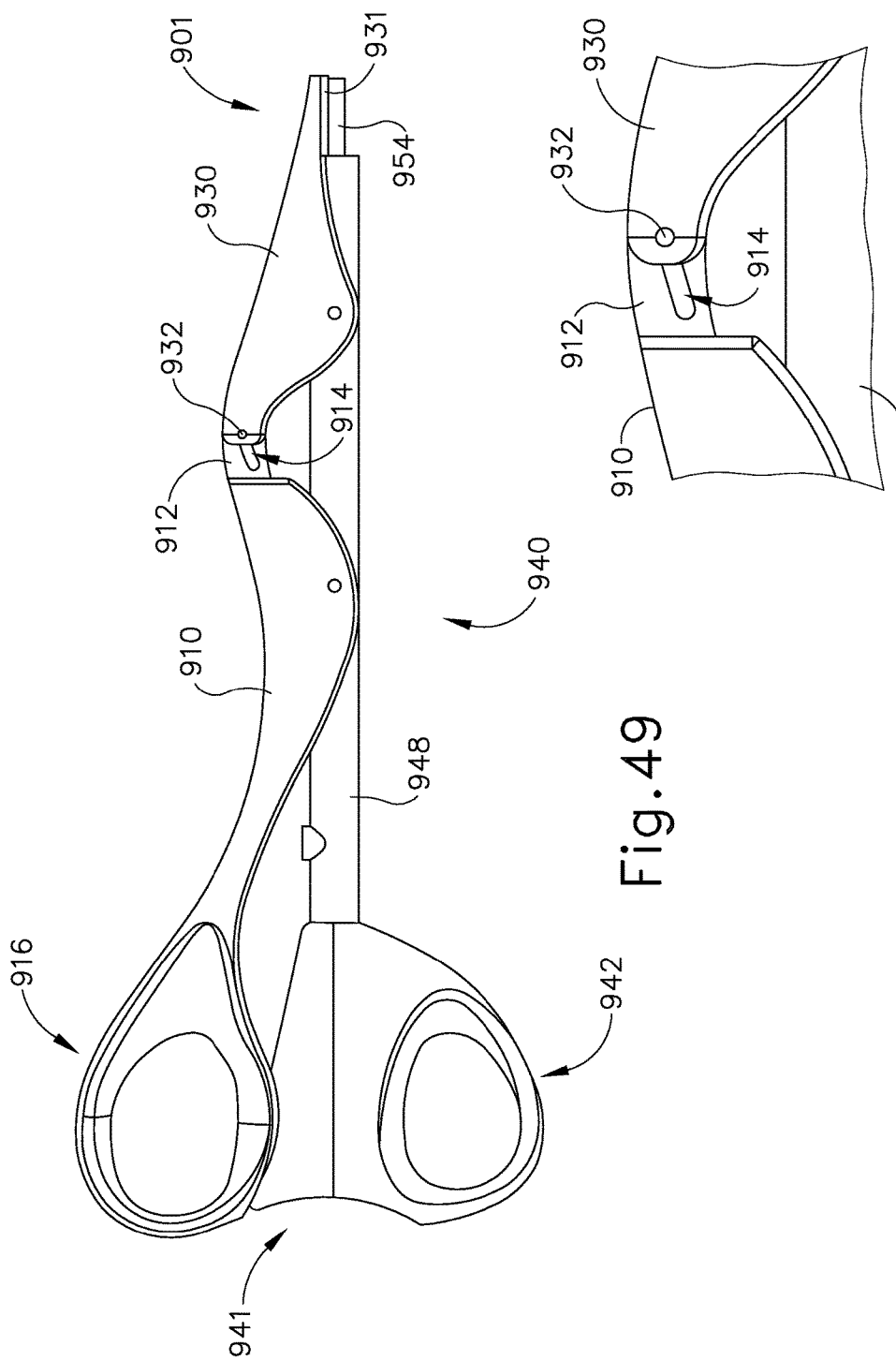
FIG. 49 depicts a side elevational view of the shaft assembly and clamp arm of FIG. 47, with the clamp arm in a closed position.
FIG. 50 depicts a detailed side elevational view of a joint of the clamp arm of FIG. 47.

With clamping mechanism (901) coupled to shaft assembly (940), the operator may use surgical instrument (900) as he or she would a pair of surgical forceps to capture and compress tissue between a clamp pad (931) of a clamp arm (930) and an ultrasonic blade (954) by pivoting clamping mechanism (901) between an open position and a closed position. With clamping mechanism (901) in an open position as shown in FIG. 51, an operator may force handle (910) downwardly toward shaft assembly (940) via thumb grip (916) so as to cause handle (910) to rotate about pins (922) within circular recesses (944, 946) to thereby cause the distal end of handle (910) to rotate upwardly away from shaft assembly (940). Rotation of the distal end of handle (910) upwardly is communicated to the proximal end of clamp arm (930) via slot (914) and pin (932) so as to cause the proximal end of clamp arm (930) to rotate upwardly about pins (938) to thereby cause the distal end of clamp arm (930) to pivot downwardly toward blade (954) into a closed position as shown in FIG. 49. To alleviate the need for any change in length between pins (922) and pins (938) due to rotation of handle (910) and clamp arm (930) about pin (932), pin (932) is configured to translate within slot (914) of tab (912). It should be understood from the foregoing that clamping mechanism (901) provides double-action leverage, with pins (922) serving as one fulcrum and pins (938) serving as another fulcrum.

As with blade (892) discussed above, blade (954) of the present example has a cylindraceous shape. Blade (954) may thus provide the same performance characteristics regardless of the angular position at which tissue contacts blade (954). It should be understood, however, that blade (954) may have any other suitable shape, including but not limited to any other ultrasonic blade shapes shown or described herein and/or shown or described in any of the references cited herein.

In an exemplary use, the operator may readily transition surgical instrument (900) between two modes of operation by selectively attaching and detaching clamping mechanism (901). For instance, the operator may perform at least part of a surgical procedure with clamping mechanism (901) detached, such that the operator uses ultrasonic blade (954) like a scalpel. The operator may thus grip and use instrument (900) in a manner similar to a grip and use of instrument (120) when clamping mechanism (901) is detached. Within the same surgical procedure (or in a different surgical procedure), the operator may attach clamping mechanism (901) to shaft assembly (880), then compress tissue between clamp pad (871) and ultrasonic blade (954) as described above. The operator may transition between these two modes as many times as desired within a given surgical procedure. Other suitable ways in which instrument (900) may be used will be apparent to those of ordinary skill in the art in view of the teachings herein.

As shown in FIG. 52, tab (912), slot (914), and pin (932) may be replaced with a living hinge (911). In such versions, it may be necessary to provide a feature configured to accommodate for any change in length between pins (922) and pins (938) due to rotation of handle (910) and clamp arm (930) about living hinge (911). For instance, as with clamping mechanism (860) discussed above, circular recesses (950, 952) could be replaced with elongate recesses. As shown in FIGS. 53 and 54, a distal end of clamp arm (930) could be shaped to accommodate different shaped blades (954). For instance, the distal end of clamp arm (930) could be curved.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument comprising:
   (a) a body, wherein the body is configured to receive an ultrasonic transducer;
   (b) a shaft assembly, wherein the shaft assembly defines a longitudinal axis, wherein the shaft assembly comprises an acoustic waveguide;
   (c) an ultrasonic blade, wherein the ultrasonic blade is in acoustic communication with the acoustic waveguide; and
   (d) a clamp arm assembly, wherein the clamp arm assembly comprises:
      (i) a coupler, wherein the coupler is configured to selectively couple the clamp arm assembly with the body or the shaft assembly and decouple the clamp arm assembly from the body or the shaft assembly, and
      (ii) an actuation member comprising:
         (A) a body member extending from a proximal end to a distal end,
         (B) a clamp pad fixed with the body member near the distal end, and
         (C) a slide extending from the body member, wherein the slide is slidably engaged with either the body or the shaft assembly when the clamp arm assembly is selectively coupled with the body or the shaft assembly, wherein a portion of the body member is configured to be moved toward the body along a path transverse to the longitudinal axis to thereby cause the slide to actuate along the body or the shaft assembly, which is configured to cause movement of the clamp pad toward the ultrasonic blade.

2. The ultrasonic instrument of claim 1, wherein the coupler is configured to selectively engage directly with the body of the ultrasonic instrument.

3. The ultrasonic instrument of claim 1, wherein the coupler is configured to selectively engage directly with the shaft assembly of the ultrasonic instrument.

4. The ultrasonic instrument of claim 1, wherein the coupler is configured to have an interference fit with the shaft assembly.

5. The ultrasonic instrument of claim 1, wherein the coupler comprises a hook shape configured to receive the shaft assembly.

6. The ultrasonic instrument of claim 1, wherein the coupler is positioned between the clamp pad and the actuation member.

7. The ultrasonic instrument of claim 1, wherein the shaft assembly is keyed into the coupler to thereby prevent rotation of the clamp arm assembly about the longitudinal axis defined by the shaft assembly.

8. The ultrasonic instrument of claim 1, wherein the actuation member comprises at least one of a finger pad, a handle, a thumb grip, or a finger grip.

9. The ultrasonic instrument of claim 1, wherein the clamp arm assembly is flexible.

10. An ultrasonic instrument comprising:
(a) a body, wherein the body is configured to receive an ultrasonic transducer;
(b) a shaft assembly, wherein the shaft assembly defines a longitudinal axis, wherein the shaft assembly comprises an acoustic waveguide;
(c) an ultrasonic blade, wherein the ultrasonic blade is in acoustic communication with the acoustic waveguide; and
(d) a clamp arm assembly comprising:
  (i) a clamp pad,
  (ii) a coupling member configured to slidably couple with the body or the shaft assembly and decouple the clamp arm assembly from the body or the shaft assembly, and
  (iii) an actuation assembly configured to actuate the clamp pad relative to the ultrasonic blade, wherein the actuation assembly comprises:
    (A) a rigid arm configured to slidably engage either the body or the shaft assembly when the coupling member is slidably coupled with the body or the shaft assembly, and
    (B) a resilient arm configured to actuate toward and away from the body such that the coupling member acts as a first fulcrum, wherein the rigid arm is configured to slide relative to the shaft assembly and coupling member in response to actuation of the resilient arm such that the rigid arm acts as a second fulcrum, wherein the clamp pad is configured to actuate relative to the ultrasonic blade in response to actuation of both the first fulcrum and the second fulcrum.

11. The ultrasonic instrument of claim 10, wherein the coupling member is configured to couple with either the body or the shaft assembly via an interference fit.

12. The ultrasonic instrument of claim 10, wherein the coupling member is configured to slidably couple with either the body or the shaft assembly via a magnet.

13. The ultrasonic instrument of claim 12, wherein the magnet is located within either the body or the shaft assembly.

14. An ultrasonic instrument comprising:
(a) a body, wherein the body is configured to receive an ultrasonic transducer;
(b) a shaft assembly, wherein the shaft assembly defines a longitudinal axis, wherein the shaft assembly comprises an acoustic waveguide;
(c) an ultrasonic blade, wherein the ultrasonic blade is in acoustic communication with the acoustic waveguide; and
(d) a removable clamp arm assembly comprising:
  (i) a clamp pad configured to actuate toward and away from the ultrasonic blade,
  (ii) an engagement assembly comprising a fixing member and a sliding member, wherein the fixing member is configured to selectively couple the removable clamp arm assembly with either the body or the shaft assembly, wherein the sliding member is configured to slide longitudinally along either the body or the shaft assembly in order to drive the clamp pad toward the ultrasonic blade, and
  (iii) a lever extending proximally from the engagement assembly, wherein the lever is configured to travel along a path that is transverse relative to the longitudinal axis in order to drive the sliding member longitudinally along either the body or the shaft assembly in order to drive the clamp pad toward the ultrasonic blade.

* * * * *